US012702449B2

(12) United States Patent
Charest et al.

(10) Patent No.: US 12,702,449 B2
(45) Date of Patent: Aug. 11, 2026

(54) GROWING ROD FOR TREATING SPINAL DEFORMITIES AND METHOD FOR USING SAME

(71) Applicant: GLOBUS MEDICAL, INC., Audubon, PA (US)

(72) Inventors: Joshua Charest, Philadelphia, PA (US); Michael Meccariello, Phoenixville, PA (US); Francis Torrente, King of Prussia, PA (US); Derrick Bingaman, Collegeville, PA (US); Jeffrey David Gordon, Phoenixville, PA (US); Jeff Nichols, Medford, NJ (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/645,586

(22) Filed: Apr. 25, 2024

(65) Prior Publication Data

US 2024/0277377 A1 Aug. 22, 2024

Related U.S. Application Data

(63) Continuation of application No. 17/569,588, filed on Jan. 6, 2022, now Pat. No. 11,986,219, which is a continuation of application No. 16/590,421, filed on Oct. 2, 2019, now Pat. No. 11,259,844, which is a continuation-in-part of application No. 16/238,864, filed on Jan. 3, 2019, now Pat. No. 11,071,568, which is a continuation-in-part of application No. 15/243,218, filed on Aug. 22, 2016, now Pat. No. 10,226,281, which is a continuation-in-part of application No. 14/874,771, filed on Oct. 5, 2015, now Pat. No. 9,949,759.

(51) Int. Cl.
*A61B 17/70* (2006.01)
*A61B 17/00* (2006.01)

(52) U.S. Cl.
CPC .................... *A61B 17/7025* (2013.01); *A61B 2017/00367* (2013.01)

(58) Field of Classification Search
CPC ............................................ A61B 17/70–7046
See application file for complete search history.

(56) References Cited

U.S. PATENT DOCUMENTS

| | | | |
|---|---|---|---|
| 458,984 | A | 9/1891 | Smith |
| 1,245,921 | A | 11/1917 | Holdren |
| 1,404,816 | A | 1/1922 | Wegstein |
| 1,698,618 | A | 1/1929 | Bigelow |

(Continued)

FOREIGN PATENT DOCUMENTS

| | | | |
|---|---|---|---|
| JP | 2009511101 | A | 3/2009 |
| JP | 2015519972 | A | 7/2015 |
| WO | 2014145470 | A2 | 9/2014 |

*Primary Examiner* — Eduardo C Robert
*Assistant Examiner* — Steven J Cotroneo

(57) ABSTRACT

An implantable growing rod assembly adapted to be secured along a length of a spine for treating deformities of the spine. The assembly includes a housing, a fixed rod extending along a longitudinal axis away from the housing, and an expansion rod extendible from the housing along the longitudinal axis. A driver assembly is fixed to the housing and adapted to translate the expansion rod along the longitudinal axis.

17 Claims, 41 Drawing Sheets

(56) References Cited

U.S. PATENT DOCUMENTS 1,852,776 A 4/1932 Hodeaux
2,231,427 A 2/1941 Larsh et al.
2,441,846 A 5/1948 Schaaff et al.
2,578,279 A 12/1951 Bardwell
3,430,510 A 3/1969 Hendrickson
3,461,738 A 8/1969 Pandjiris et al.
3,535,948 A 10/1970 Winzeler et al.
3,710,640 A 1/1973 Stranger et al.
4,077,274 A 3/1978 Johnson
4,215,599 A 8/1980 Batchelder et al.
4,931,055 A * 6/1990 Bumpus ............. A61B 17/7014 606/907
5,345,845 A 9/1994 Myers
5,630,343 A 5/1997 Begin
5,700,263 A 12/1997 Schendel
5,934,144 A 8/1999 Marinkovic
7,029,472 B1 4/2006 Fortin
7,979,988 B2 7/2011 Shiino et al.
8,113,074 B2 2/2012 Wohrle et al.
8,591,547 B2 11/2013 Swisson, III et al.
8,641,723 B2 2/2014 Connor
9,301,788 B2 4/2016 Wolters et al.
9,561,061 B2 2/2017 Swisson, III et al.
11,259,844 B2 * 3/2022 Charest .............. A61B 17/7025
11,986,219 B2 * 5/2024 Charest .............. A61B 17/7016
2004/0059331 A1 * 3/2004 Mullaney ........... A61B 17/6458 606/59
2004/0206195 A1 10/2004 Landskron et al.
2006/0122606 A1 6/2006 Wolgen
2006/0195088 A1 8/2006 Sacher et al.
2009/0036892 A1 * 2/2009 Karidis .................. A61B 17/66 606/60
2009/0112207 A1 * 4/2009 Walker ................. A61B 17/707 600/12
2009/0275984 A1 * 11/2009 Kim ...................... A61B 17/68 606/259
2010/0004697 A1 1/2010 Fortin et al.
2010/0049204 A1 * 2/2010 Soubeiran ................. A61F 2/30 606/90
2010/0234844 A1 * 9/2010 Edelhauser ............ A61B 17/62 606/56
2012/0203282 A1 * 8/2012 Sachs ................. A61B 17/7041 606/279
2013/0110171 A1 * 5/2013 Suh .................... A61B 17/7028 606/257
2013/0338713 A1 12/2013 Kawakami et al.
2014/0236234 A1 * 8/2014 Kroll .................. A61B 17/7083 606/279
2014/0276822 A1 * 9/2014 Cresina .............. A61B 17/6416 606/57
2016/0270825 A1 * 9/2016 Wentz ................ A61B 17/7016
2016/0324550 A1 11/2016 Wolters et al.
2017/0325854 A1 11/2017 Rouge et al.
2018/0028239 A1 2/2018 Swisson, III et al.

* cited by examiner 102
502
104
412
506

302
406
508
504

220
224
226
214
216
204
258
256
243
206
242
244
230
250
246
254
208

220
221
D1
214
212
210
216
201
205
D2
202
224
204
222
256
258
243
244
242
240
252
250
206
254
208

3324
3310
3304
3352
3342
3344
3346
3348
3354
3308

3313
3301
3305
3302
3312
3306A
3306

4424
4404
4404
4447
4452
4443
4444
4448
4442
4446
4449
4454
4408

4424
4410
4401
4405
4404
4402
4412
4447
4452
4406A
4444
4448
4406
4442
4446
4449
4408

4824
4810
4804
4847
4852
4848
4888
4880
4882
4843
4844
4846
4842A
4849
4842B
4854
4808
4884

4943
4846
4849
4843
4848

4846
4849
4880
4843
4848

4824
4810
4805
4801
4804
4802
4812
4847
4852
4846
4848
4842A
4842B
4806A
4849

4824
4810
4812
4804
4805
4802
4847
4846
4848
4842A
4842B
4806A
4849

GROWING ROD FOR TREATING SPINAL DEFORMITIES AND METHOD FOR USING SAME

REFERENCE TO RELATED APPLICATIONS

The present application is a continuation application of U.S. patent application Ser. No. 17/569,588, filed on Jan. 6, 2022 (published as U.S. Pat. Pub. 2022-0125482), which is continuation application of U.S. patent application Ser. No. 16/590,421, filed on Oct. 2, 2019 (now U.S. Pat. No. 11,259,844), which is a continuation-in-part of U.S. patent application Ser. No. 16/238,864, filed Jan. 3, 2019 (now U.S. Pat. No. 11,071,568), which is a continuation-in-part of U.S. patent application Ser. No. 15/243,218, filed Aug. 22, 2016 (now U.S. Pat. No. 10,226,281), which is a continuation-in-part of U.S. patent application Ser. No. 14/874,771 (now U.S. Pat. No. 9,949,759), filed Oct. 5, 2015, both of which are hereby incorporated by reference in their entireties for all purposes.

FIELD OF THE INVENTION

The present invention relates generally to a growing rod for treating spinal deformities, and more particularly to a growing rod that can be secured to a spine of a patient and manually extended to grow with the patient's spine.

BACKGROUND OF THE INVENTION

Scoliosis is a term used to describe any abnormal, sideway curvature of the spine. The most common form of scoliosis for patients between the age of 10 and 18 years is termed adolescent idiopathic scoliosis (AIS). Although the particular cause of this type of scoliosis is still unknown, advancements in the medical field have enabled doctors to increase the likelihood of successfully treating scoliosis is children and adolescents.

Studies have shown that curvatures in the spine progress during the rapid growth period of children. Because of this, children suffering from scoliosis are generally recommended by their doctor to undergo surgical treatment to prevent curve progression and to obtain some curve correction.

One type of spinal surgery for treating scoliosis in children is the use of implantable rods that allow for continued growth of the spine. One or two rods are implanted into the child through the back of the spine. The rods are then secured to the spine above and below the curve using hooks or screws. Because the child will continue to grow after the spinal surgery, the child will be required to return every few months to have the rods lengthened to keep up with his/her growth.

There thus exists a need to provide improved growing rods.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention cures some of the deficiencies in the prior art by providing a growing rod that is less complex and that can be manually extended by a user.

The growing rod of the illustrative embodiment of the present invention is adapted to be subcutaneously implanted and secured along a length of a spine of a patient. The growing rod comprises a base rod, an extendible rod having a distal portion that is slidably coupled to the base rod and arranged with a gear rack, and a distraction unit.

The distraction unit provides one or more mechanical elements to facilitate linear movement of the extendible rod relative to the base rod. In general, the distraction unit comprises: (i) a housing attached to the base rod, (ii) a rotatable drive interface accessible by an external driver from outside of the housing, and (iii) a drive gear mechanism housed within the housing and coupled to the rotatable drive interface and the gear rack such that rotation of the rotatable drive interface causes linear movement of the extendible rod through the gear rack.

Because the patient is likely to continue to grow after implantation of the growing rod, the patient will be required to return to the doctor (e.g., two months, four months, six months, etc., after each doctor's visit) to have the growing rod extended in order to keep up with the patient's growth. This can be accomplished by making a small incision on the patient's back to access the rotatable drive interface with an external driver. The rotatable drive interface is adapted to be physically coupled to and manually rotated by the external driver employed by the doctor. As the doctor rotates the rotatable drive interface in a first direction (e.g., clockwise), it causes linear movement of the extendible rod through the gear rack. The linear movement is a result of a gear in the drive gear mechanism cooperating with the gear rack to linearly move the extendible rod relative to the base rod. A latching mechanism housed within the housing is configured to latch onto the drive gear mechanism to prevent the rotatable drive interface from being able to rotate in a second direction (e.g., counter-clockwise) for retracting the extendible rod. The latching mechanism also provides a means to prevent the drive gear mechanism from causing the extendible rod from retracting under pressure of the spine; for example, when the patient is sitting up, standing, walking, etc.

To unlatch the latching mechanism, provided is a rotatable cam interface arranged on the outside of the housing. The doctor can access the rotatable cam interface by using an external cam driver. Rotating the rotatable cam interface using the driver causes a cam housed within the housing to unlatch the latching mechanism from the drive gear mechanism, thereby allowing the doctor to rotate the rotatable drive interface in the second direction. This feature allows the doctor to fine tune the overall length of the growing rod if the extendible rod has been extended too much.

By providing a manually operated implant that is less complex, like the growing rod of the illustrative embodiment, fewer elements and moving parts can be used to extend and retract the implant without the need of a power source.

In an alternative embodiment of the present invention, different types of gears and gear configurations are employed to extend the extendible rod relative to the base rod.

In a further alternative embodiment of the present invention, the extendible rod is extended relative to the base rod by means of applying fluid pressure through a fluid intake coupled to a fluid connection body of the growing rod. The fluid pressure enters the connection body and forces a piston forwards to extend the extendible rod.

In yet another alternative embodiment, a growing rod is adapted to be extended by incrementally pushing a toggling switch on the surface of a patient's skin.

In still a further alternative embodiment, an implantable growing rod assembly is adapted to be secured along a length of a spine for treating deformities of the spine. The assembly includes a housing, a fixed rod extending along a longitudinal axis away from the housing, and an expansion rod extendible from the housing along the longitudinal axis. A driver assembly is fixed to the housing and adapted to translate the expansion rod along the longitudinal axis.

These advantages of the present invention will be apparent from the following disclosure and the appended claims.

BRIEF DESCRIPTION OF THE DRAWINGS

Other aspects, features, and advantages of the present device will become more fully apparent from the following detailed description, the appended claims, and the accompanying drawings in which like reference numerals identify similar or identical elements.

DETAILED DESCRIPTION

Figures 1, 2:
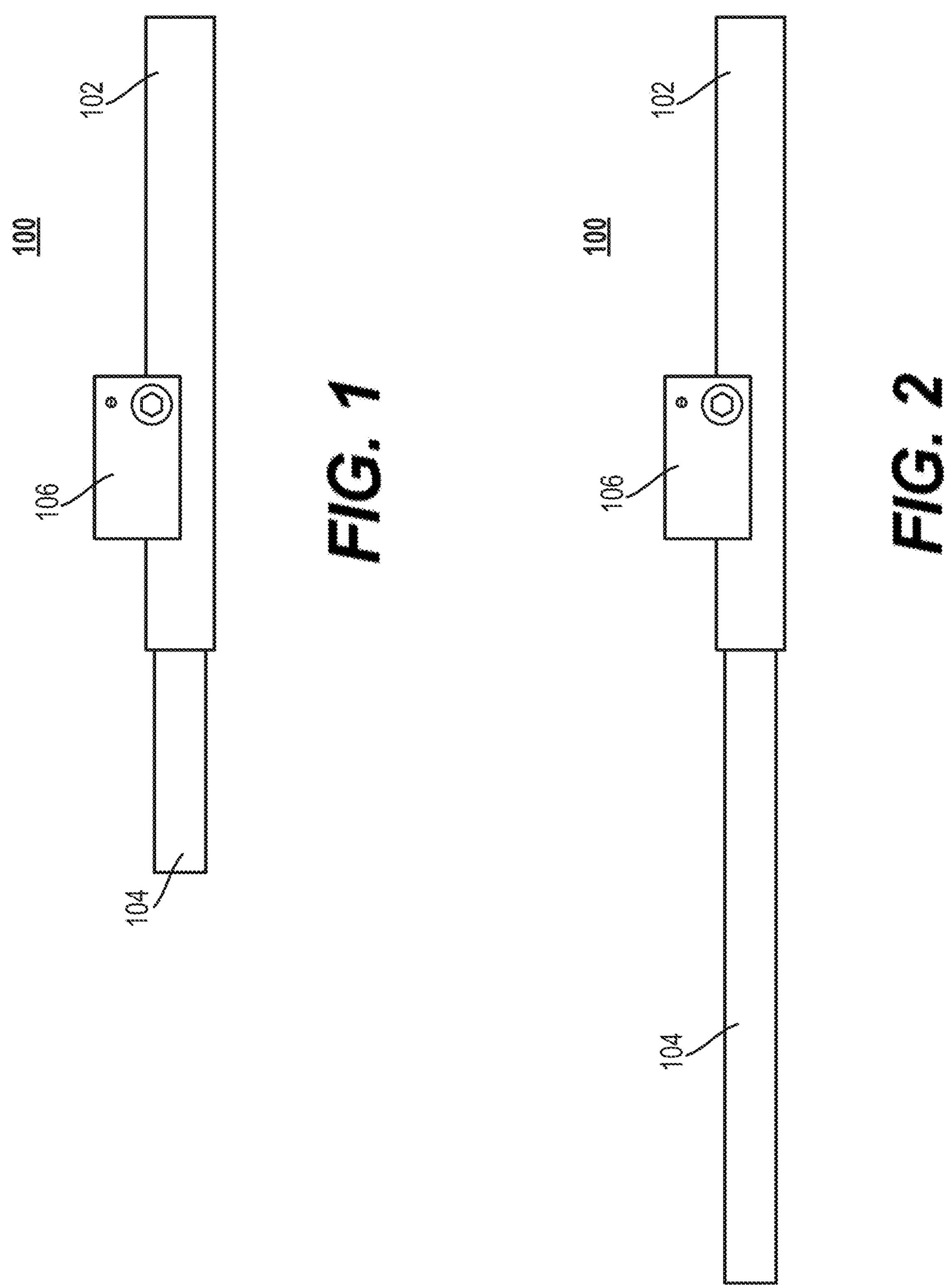
FIG. 1 is a perspective view of a growing rod in a collapsed configuration in accordance with an illustrative embodiment of the present invention.
FIG. 2 is a perspective view of the growing rod of FIG. 1 in a fully extended configuration in accordance with an illustrative embodiment of the present invention.

In the drawings, like numerals indicate like elements throughout. Certain terminology is used herein for convenience only and is not to be taken as a limitation on the present device. The terminology includes the words specifically mentioned, derivatives thereof and words of similar import.

The embodiments illustrated below are not intended to be exhaustive or to limit the device to the precise form disclosed. These embodiments are chosen and described to best explain the principle of the device and its application and practical use and to enable others skilled in the art to best utilize the device.

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present device.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required.

FIG. 1 shows a growing rod 100 in a collapsed configuration in accordance with an illustrative embodiment of the present invention. The growing rod comprises: base rod 102, extendible rod 104, and distraction unit 106. Each of these elements that form growing rod 100 can be constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of growing rod 100 is made from a durable thermoplastic polymer, such as polyether ether ketone (PEEK).

In accordance with the illustrative embodiment, extendible rod 104 has a proximal portion that is slidably coupled to base rod 102 and arranged with a gear rack. The extendible rod may be constructed to have a slightly smaller diameter than that of base rod 102 in order to allow the extendible rod to telescopically slide in and out of the base rod. It will be clear to those skilled in the art, after reading this disclosure, how to make and use alternative embodiments of the present invention in which base rod 102 can be adapted to slide in and out of extendible rod 104.

FIG. 2 shows growing rod 100 in a fully extended configuration in accordance with an illustrative embodiment of the present invention. In this figure, extendible rod 104 has been fully extended relative to base rod 102 in response to a doctor manually rotating a rotatable drive interface that is arranged on the outside of distraction unit 106. The doctor can also fine tune the length of growing rod 100 by retracting extendible rod 104 to a desired distraction length. The doctor can achieve this by manually rotating a rotatable cam interface arranged on the outside of distraction unit 106 in the opposite direction. The illustrative embodiment of extendible rod 104 is adapted to allow for a minimum of three and a half years growth before replacement or removal is required. However, it will also be clear to those skilled in the art, after reading this disclosure, how to make and use alternative embodiments in which extendible rod 104 is adapted for more or less than three and a half years growth before replacement or removal is required. These features of the present invention will be described in more detail below, with respect to FIGS. 3 and 4.

Figure 3:
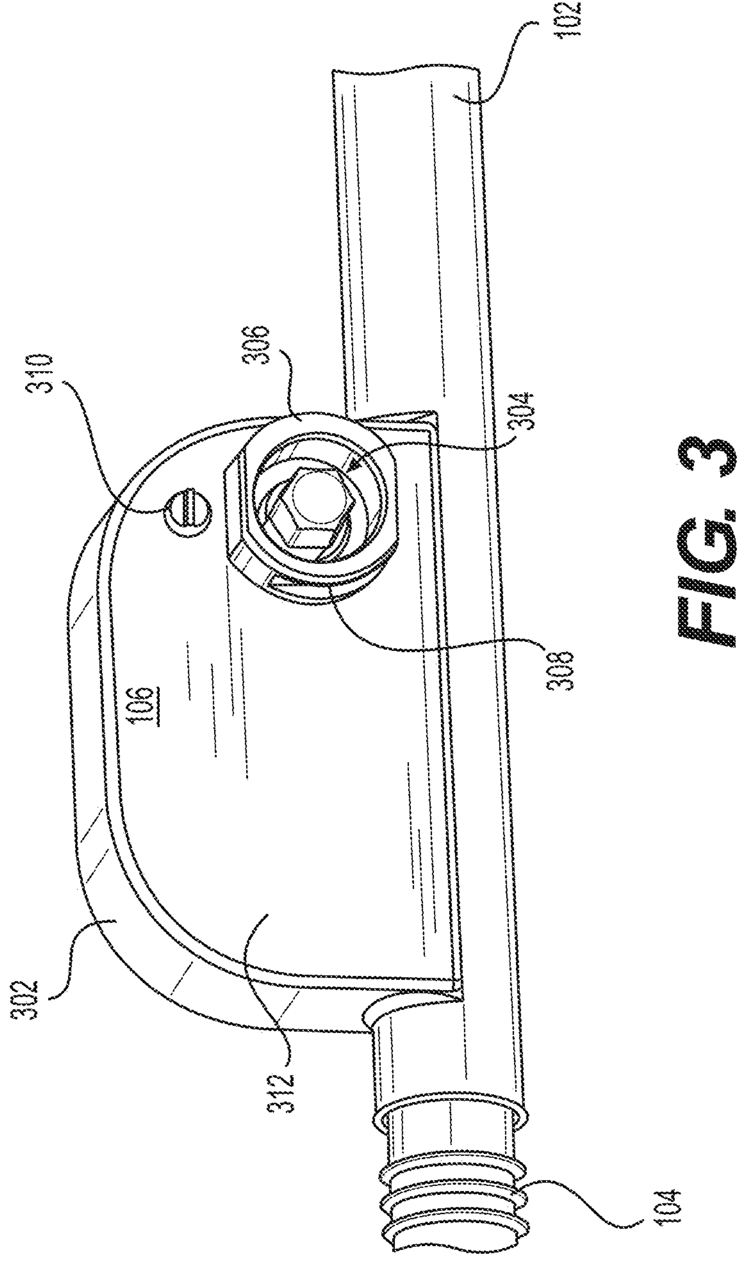
FIG. 3 depicts the outside of a housing of a distraction unit in accordance with an illustrative embodiment of the present invention.

FIG. 3 is a perspective view of the outside of distraction unit 106 in accordance with an illustrative embodiment of the present invention. The distraction unit comprises: housing 302, rotatable drive interface 304, guide wall 306, recess 308, rotatable cam interface 310, and cover plate 312. Each of these elements of distraction unit 106 can be constructed from a biocompatible plastic, metal, metal alloy, or combination thereof. The biocompatible metals and metal alloys can be, for example, and without limitation, titanium, titanium alloy, stainless steel, cobalt chrome, or any combination thereof.

As shown in the figure, rotatable drive interface 304 is arranged on the outside of housing 302 and is accessible to a doctor via an external driver. The rotatable drive interface 304 is hexagon-shaped and is adapted to be received in a correspondingly shaped recess of the external driver. The rotatable drive interface 304 can be, for example, and without limitation a 35 mm hex drive interface. Although rotatable drive interface 304 is depicted as hexagon-shaped, it will be clear to those skilled in the art, after reading this disclosure, how to make and use alternative embodiments of the present invention in which rotatable drive interface 304 can have any shape and size, so long as it can be received by the recess of the external driver.

As further shown in the figure, rotatable drive interface 304 is surrounded by guide wall 306, which has a pair of oppositely positioned recesses 308 arranged on the outer surface of the guided wall. Only one recess 308 is shown in the figure, but it will be clear to those skilled in the art, after reading this disclosure, that one half of guide wall 306 is substantially a mirror image of the other half of the guide wall. In accordance with the illustrative embodiment, each recesses 308 is adapted to receive a correspondingly shaped and sized protrusion, hook, etc., arranged on the external driver. Once received, the external driver is locked to guide wall 306 such that lateral movement of the external driver is prevented. This mechanism helps prevent the external driver from dislodging from rotatable drive interface 304 as the doctor is rotating it. The physical structure of guided wall 306 also has the added benefit of helping the doctor determine where rotatable drive interface 304 might be located underneath the skin.

Housing 302 also includes rotatable cam interface 310, which is coupled to a cam housed within housing 302. Although the figure depicts rotatable cam interface 310 as having a slotted head for receiving a corresponding shaped external cam driver, it will be clear to those skilled in the art, after reading this disclosure, that rotatable cam interface 310 can have any shape and size, so long as it can receive the external cam driver. As will be discussed in more detail below, with reference to FIG. 4, rotating interface 310 causes a cam housed within housing 302 to disengage a latch from a drive gear mechanism so that a doctor can retract extendible rod 104.

Figure 4:
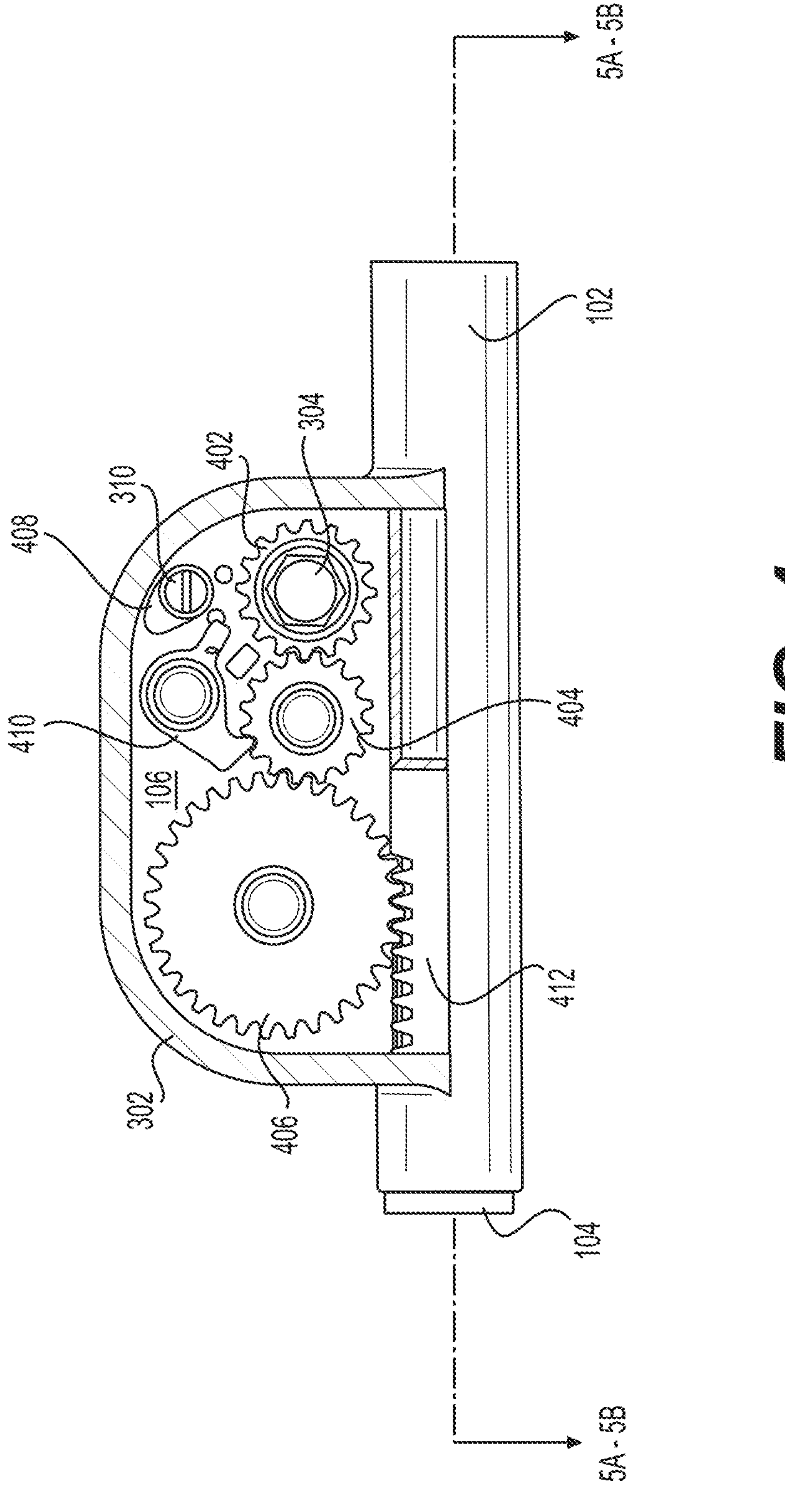
FIG. 4 depicts the inside of the housing of the distraction unit in accordance with an illustrative embodiment of the present invention.

FIG. 4 is a cross-sectional view of the interior of distraction unit 106, thus housing 302, in accordance with an illustrative embodiment of the present invention. The interior of the distraction unit comprises: drive gear 402, idler gear 404, pinion 406, cam 408, and latch 410. Like all of the elements that form growing rod 100, elements 402 to 410 can be constructed from a biocompatible plastic, metal, metal alloy, or combination thereof. The biocompatible metals and metal alloys can be, for example, and without limitation, titanium, titanium alloy, stainless steel, cobalt chrome, or any combination thereof.

Removing cover plate 312 from housing 302 reveals a drive gear mechanism that is coupled to rotatable drive interface 304 and gear rack 412. The gear rack 412 is preferably arranged on a proximal portion of extendible rod 104, but it will be clear to those skilled in the art, after reading this disclosure, how to make and use alternative embodiments of the present invention in which gear rack 412 is arranged along the length of extendible rod 104.

In accordance with the illustrative embodiment, the drive gear mechanism comprises drive gear 402, idler gear 404, and pinion 406. These gears are coupled to one another as shown in the figure to form a "simple gear train". The gear ration between drive gear 402 and pinion 406 is preferably 2-to-1 (i.e., 2:1 ratio). What this means is that pinion 404 has twice as many teeth as drive gear 402. However, those skilled in the art will appreciate after reading this disclosure that distraction unit 106 can be configured to have any number of gears and different gear ratio ranges without departing from the scope of the invention. For example, the gear ratio range can have a lower limit of 1.5 and an upper limit of 10.

Furthermore, although FIG. 4 only depicts the drive gear mechanism as having three gears, it will be clear to those skilled in the art, after reading this disclosure, how to make and use alternative embodiments of the present invention in which the drive gear mechanism has fewer or more gears than depicted. For example, and without limitation, the drive gear mechanism can have one gear, two gears, ten gears, etc., without departing from the scope of the present invention. It will also be clear to those skilled in the art that other types of gears and gear trains could be used without departing from the scope of the present invention. Other types of gears may include, for example, and without limitation, spur gears, helical gears, herringbone gear, face gears, screw gears, etc., or a combination thereof. Other types of gear trains may include, for example, and without limitation, compound gear trains, reverted gear trains, epicyclic gear train, etc., or a combination thereof. Lastly, it will be clear to those skilled in the art, after reading this disclosure, how to make and use alternative embodiments of the present invention in which distraction unit 106 can be configured to have different number of gears and different gear ratios without departing from the scope of the invention.

As briefly described above, rotatable drive interface 304 is adapted to be accessed by an external driver from outside of housing 302. The rotatable drive interface is also adapted to be physically coupled to and manually rotated by the external driver for extending and retracting the extendible rod relative to the base rod. More specifically, rotating interface 304 in a first direction (e.g., clockwise) rotates drive gear 402 in the same direction. In response to the rotational movement of drive gear 402, idler gear 404 will also begin to rotate, but in the opposite direction, while pinion 406 will rotate in the same direction as drive gear 402. Thus, gears 402, 404, and 406 are coupled to rotatable drive interface 304 in such a way that rotation of the rotatable drive interface causes each of the gears to simultaneously rotate. The rotational movement from gears 402, 404, and 406 is then translated into linear movement by coupling pinion 406 to gear rack 412.

Figures 5A, 5B:
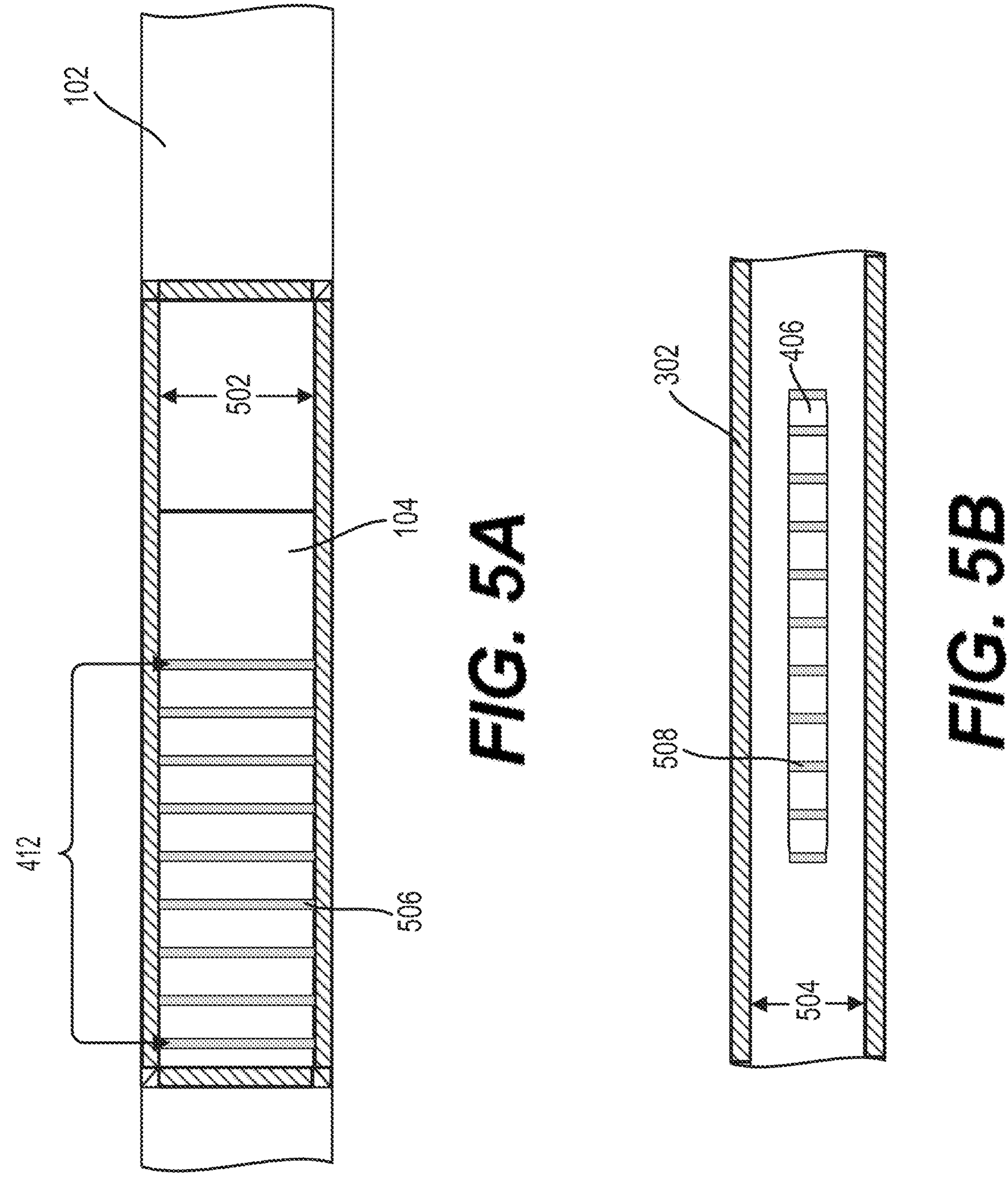
FIG. 5A depicts an opening arranged on a base rod of the growing rod in accordance with an illustrative embodiment of the present invention.
FIG. 5B depicts an opening arranged on the housing of the distraction unit in accordance with an illustrative embodiment of the present invention.

The coupling between pinion 406 and gear rack 412 is made possible by coupling housing 302 of distraction unit 106 to base rod 102 as shown in FIGS. 2 and 3. More specifically, and as shown in FIG. 5A, the outer surface of base rod 102 is machined with an opening 502. The opening 502 is arranged at a distal portion of base rod 102. The opening 502 can also be seen in FIG. 4. Similarly, housing 302 has an opening 504 arranged on one side of the housing. The opening 504 of housing 302 is shown in FIG. 5B. In accordance with the illustrative embodiment, the teeth 508 of pinion 406 extend slightly outside of opening 504 of housing 302. This allows the teeth 508 of pinion 406 to extend through opening 502 of base rod 102 to engage the teeth 506 of gear rack 412 when housing 302 is coupled to base rod 102, thereby forming a rack-and-pinion configuration. As discussed above, rotational movement of pinion 406 is translated into linear movement by gear rack 412 such that extendible rod 104 can be either extended or retracted, depending on which direction rotatable drive interface 304 is rotated.

Referring back to FIG. 4, the latching mechanism housed within housing 302 is adapted to latch onto a gear of the drive gear mechanism such that rotation of rotatable drive interface 304 is prohibited in a direction (e.g., in a counter-clockwise direction) that retracts extendible rod 104. In accordance with the illustrative embodiment, the latching mechanism comprises latch 410, which is biased to lock the drive gear mechanism. As shown in the figure, latch 410 is biased to latch onto and lock idler gear 404. Although latch 410 is biased to lock idler gear 404 in the illustrative embodiment, it will be clear to those skilled in the art, after reading this disclosure, how to make and use alternative embodiments of the present invention in which latch 410 is biased to lock drive gear 402 or pinion 406 instead.

Continuing with the illustrative embodiment, latch 410 is sized and shaped to be received between a pair of adjacent teeth of idler gear 404. Latch 410 is spring-loaded in the illustrative embodiment and is adapted to ratchet back and forth as rotatable drive interface 304 is rotated in the clockwise direction for extending rod 104. However, the size and shape of latch 410 relative to the root/pitch of idler gear 404 prevents latch 410 from being able to ratchet back and forth when rotatable drive interface 304 is rotated in the counter-clockwise direction for retracting rod 104. That is, latch 410 will not be dislodged from between the pair of adjacent teeth of idler gear 404 when rotatable drive interface 304 is rotated in a direction that retracts extendible rod 104. This feature of the present invention is advantageous in that downward pressure exerted on the spine (e.g., when the patient is sitting up, standing, etc.) after implantation of growing rod 100 will not cause gears 402, 404, 406 to unintendedly rotate and inadvertently retract rod 104.

Figure 6:
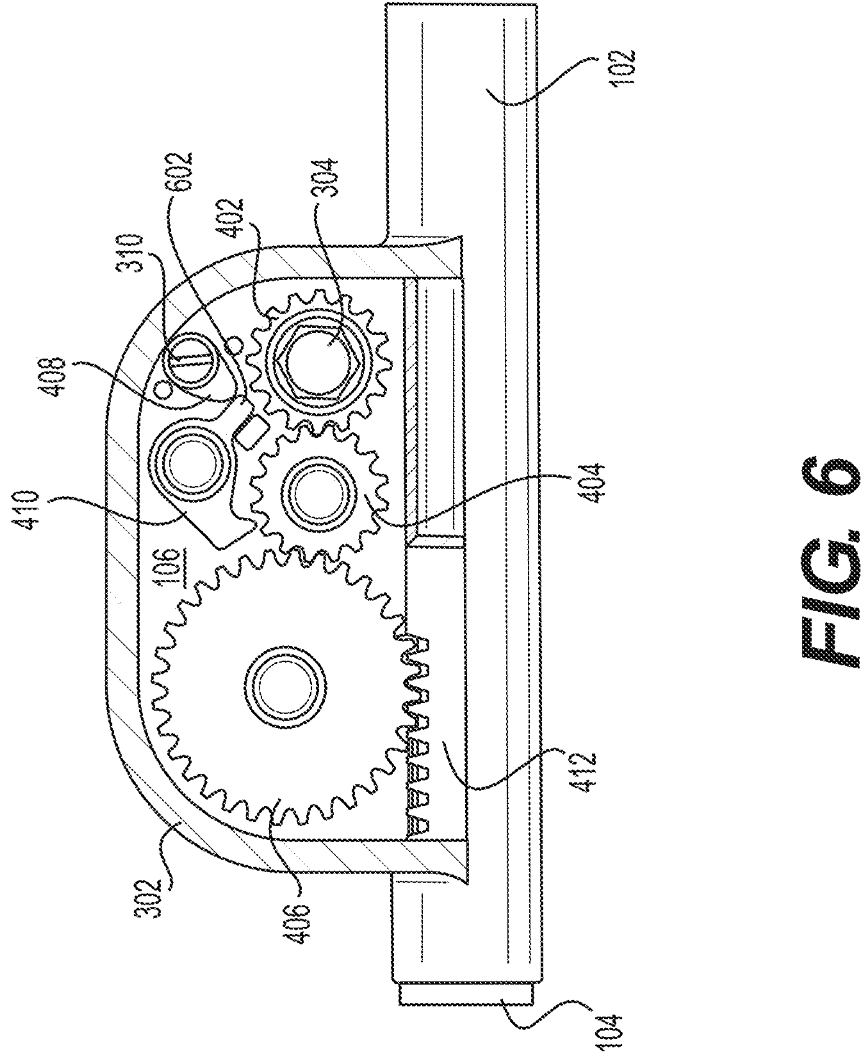
FIG. 6 depicts a cam and a latch configuration for allowing an extendible rod of the growing rod to be retracted.

FIG. 6 shows latch 410 unlatched from between the pair of adjacent teeth of idler gear 404 in accordance with the illustrative embodiment. To unlatch latch 410, rotatable cam interface 310 is provided. The rotatable cam interface is accessible by an external cam driver from outside of housing 302. The rotatable cam interface 310 is coupled to cam 408 such that rotation of the rotatable cam interface causes the latching mechanism to either prohibit or allow the drive gear mechanism to rotate in a direction that retracts or extends the extendible rod 104.

Specifically, rotatable cam interface 310 is adapted to be physically coupled to and manually rotated by external cam driver 310 such that rotation of rotatable cam interface 310 causes a tip of cam 408 to engage or be free from physical contact with latch 410. The rotatable cam interface 310 is rotatable from outside of housing 302 in a first direction (e.g., counter-clockwise) until the tip of cam 310 abuts against lever 602 of latch 410 and pins it against stopper 604. This causes latch 410 to be unlatched from between the pair of adjacent teeth of idler gear 404. This also holds latch 410 in the unlatched position so that the doctor can rotate interface 304 to retract extendible rod 104 to a desired length. After reaching the desired length, the doctor can use the external cam driver to rotate interface 310 in a second direction (e.g., clockwise) to position latch 410 between a pair of adjacent teeth of idler gear 404, thereby locking gears 402, 404, and 406 from rotating in a direction that retracts extendible rod 104.

Having described the elements of growing rod 100 in particular detail, an example of using growing rod 100 will now be described. After growing rod 100 has been implanted into a patient, the patient may be required to return to the doctor every few months to have growing rod 100 extended to keep up with his/her growth. To extend growing rod 100, the doctor uses his hands to feel for where distraction unit 106 is located; in particular, where guide wall 306 is located underneath the patient's skin. Once located, a small incision is made on the patient's back near guide wall 306. An external driver is inserted through the small incision and then physically coupled to rotatable drive interface 304 from outside of housing 302. Once coupled, the doctor may manually rotate rotatable drive interface 304 using the coupled external driver. As discussed above, with respect to FIGS. 3-6, rotating interface 304 also rotates drive gear 402, idler gear 404, and pinion 406, since each of these gears are either physically or indirectly coupled to rotatable drive interface 304. The rotational movement of these gears is then translated into linear movement through the rack-and-pinion configuration created by coupling pinion 406 to gear rack 412. The linear movement of gear rack 412 causes extendible rod 104 to linearly extend relative to base rod 102. Likewise, rotating interface 304 in the opposite direction causes extendible rod 104 to linearly retract relative to base rod 102, as discussed above, with respect to FIGS. 3-6.

It should be noted that "manual" rotation of rotatable drive interface 304 includes, for example, and without limitation, physically coupling the external driver to rotatable drive interface 304 and then having the doctor manually rotate the physically coupled external driver in a clockwise or counter-clockwise direction. In this embodiment, the external driver is similar to, for example, and without limitation, a socket wrench that is not electrically driven.

In alternative embodiments, "manual" rotation of rotatable drive interface 304 includes, for example, and without limitation, physically coupling the external driver to rotatable drive interface 304 and then actuating one or more buttons to electrically power the physically coupled external driver. In this embodiment, a power source provides electricity of the physically coupled external driver to manually rotate interface 304.

Figure 7A:
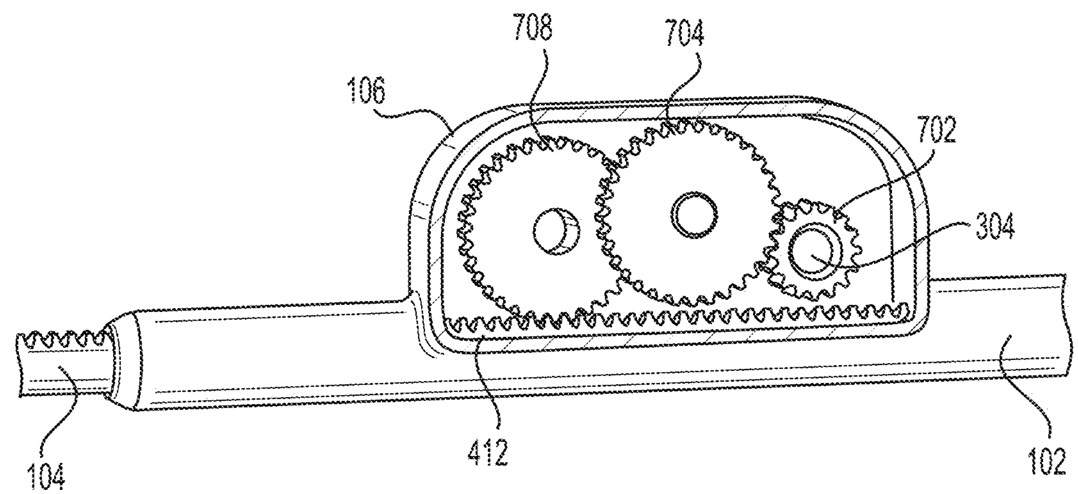
FIG. 7A depicts an extendible rod having a gear train that shows one side of a compound gear in accordance with an alternative embodiment of the present invention.
Figure 7B:
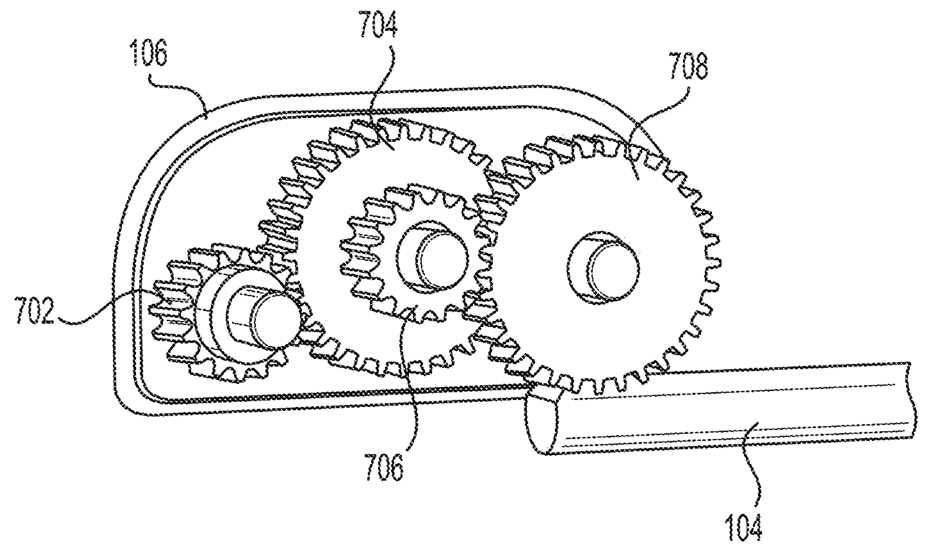
FIG. 7B depicts the other side of the gear train of FIG. 7A in accordance with an alternative embodiment of the present invention.

FIGS. 7A and 7B depict an alternative embodiment of extendible rod 104 discussed above. FIG. 7A depicts one side of housing 302 of distraction unit 106 with cover plate 312 removed. Housed within housing 302 in this alternative embodiment are four gears—namely, drive gear 702, a compound gear formed by a larger gear 704 having a smaller gear 706 coupled on one side of the larger gear, and pinion 708. The smaller gear 706 is shown in FIG. 7B.

In accordance with this alternative embodiment, drive gear 702 is coupled to larger gear 704 (as shown in FIG. 7A) and smaller gear 706 is coupled to pinion 708 (as shown in FIG. 7B). Pinion 708 in turn is coupled to gear rack 412, as discussed above, with respect to FIGS. 3-5B. The gear configuration in this alternative embodiment has, for example, and without limitation, a gear ratio of 4-to-1 (i.e., 4:1 ratio). However, those skilled in the art will appreciate after reading this disclosure that distraction unit 106 can be configured to have different number of gears and different gear ratios without departing from the scope of the invention.

To extend or retract extendible rod 104 relative to base rod 102, rotatable drive interface 304 can be respectively rotated in a clockwise or a counter-clockwise direction, as discussed above, with respect to FIGS. 3-5B. As interface 304 rotates drive gear 702, the larger gear 704 and smaller gear 706 also rotate, but in the opposite direction of drive gear 702. The coupling between smaller gear 706 and pinion 708 causes linear movement of extendible rod 104 through gear rack 412, as discussed above. Although FIGS. 7A and 7B do not depict the latching mechanism (e.g., latch 410, rotatable cam interface 310, cam 408, stopper 604, etc.) discussed above, those skilled in the art will appreciate that this alternative embodiment can be configured to include the latching mechanism. The advantage of having a gear train that includes a compound gear is the ability to more easily meet the distraction force for extending extendible rod 104.

Figure 8A:
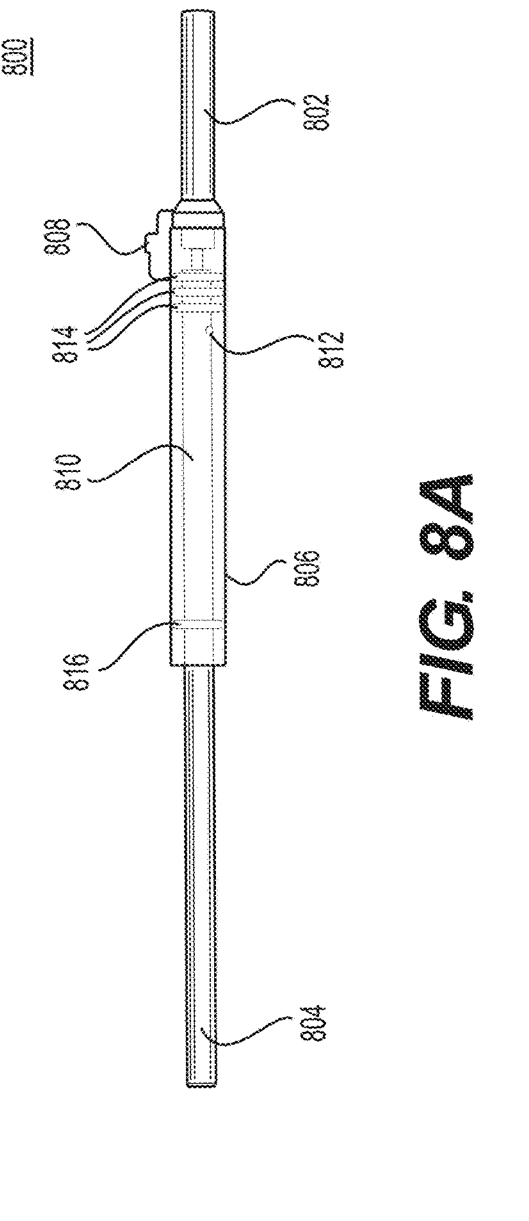
FIG. 8A is a perspective view of a hydraulic growing rod in a collapsed configuration in accordance with an alternative embodiment of the present invention.

FIG. 8A shows a growing rod 800 in a collapsed configuration in accordance with an alternative embodiment of the present invention. The growing rod comprises: base rod 802, extendible rod 804, fluid connector body 806, fluid intake 808, piston 810, spring-loaded ball 812, fluid seals 814, end seal 816, input tube 818, and port 820.

Figure 8B:
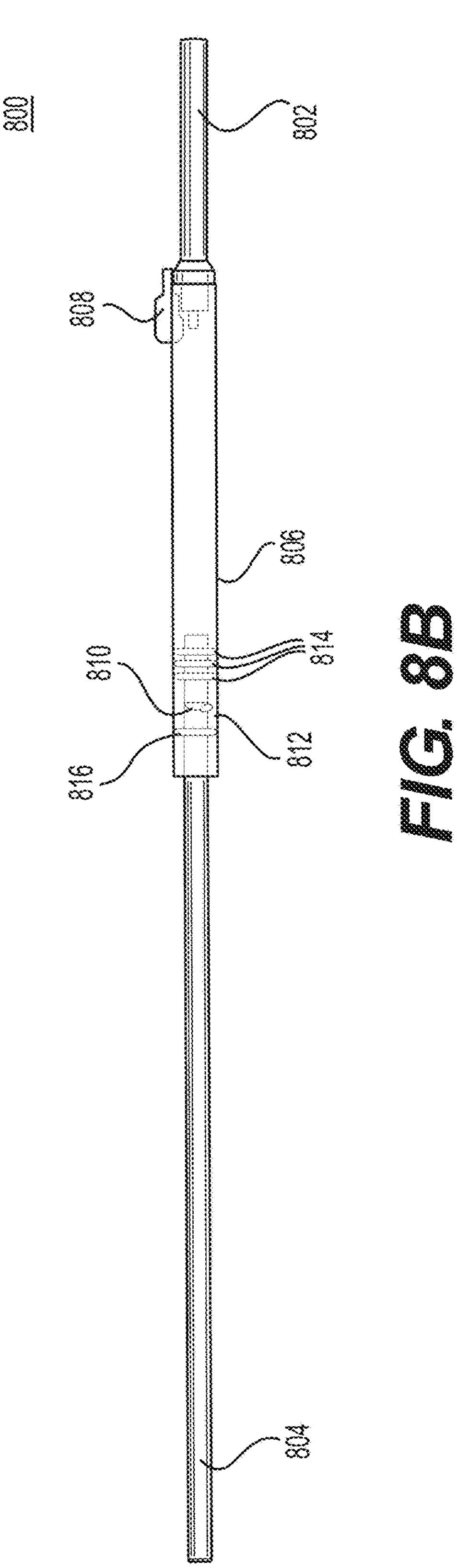
FIG. 8B is a perspective view of the g hydraulic rowing rod of FIG. 8A in a fully extended configuration in accordance with an alternative embodiment of the present invention.

FIG. 8B shows growing rod 800 in a fully extended configuration in accordance with an alternative embodiment of the present invention. As will be discussed in more detail below, with respect to FIG. 9, extendible rod 804 has been fully extended relative to base rod 802 in response to fluid pressure being applied through fluid intake 808 to force piston 812 forwards.

Figure 9:
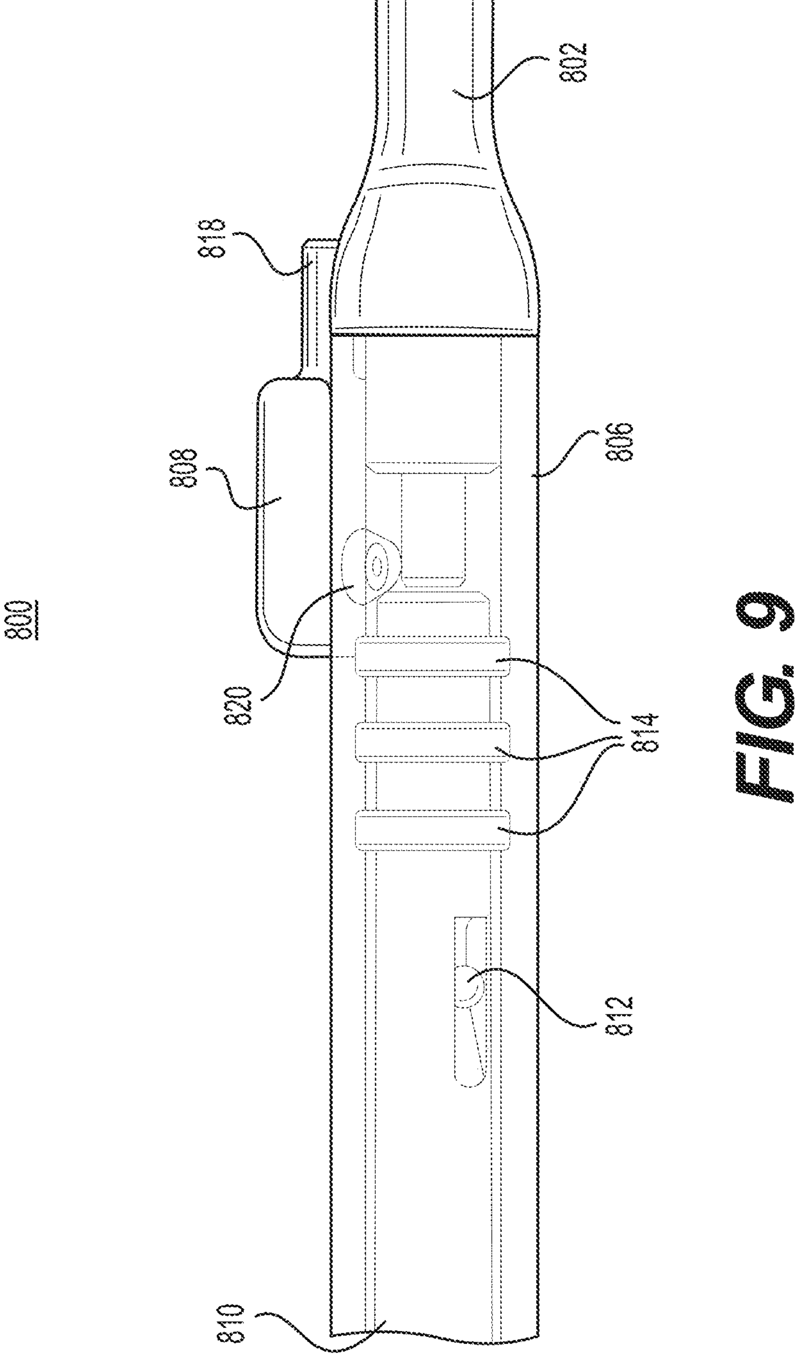
FIG. 9 is an exploded view of the fluid connection body, fluid intake, and piston for extending an extendible rod through fluid pressure in accordance with an alternative embodiment of the present invention.

Turning now to FIG. 9, and in accordance with this alternative embodiment, growing rod 800 is implanted along a spine of a patient and can be expanded after implantation to keep up with the growth of the patient. More specifically, growing rod 800 can be expanded by making a small incision on the patient's back to access an input tube 818 arranged on fluid intake 808, which fluid intake is coupled to connector body 806 of growing rod 800. Once accessible, a fluid hose coupled to a fluid delivery device is connected to input tube 818 of fluid intake 808. The fluid delivery device is then operated to apply fluid pressure (e.g., saline fluid, etc.) through fluid intake 808. The fluid pressure exits port 820 and forces piston 812 forwards, thereby extending rod 804 relative to base rod 802. Although three fluid seals are shown in the figures, it will be clear to those skilled in the art, after reading this disclosure, how to make and use alternative embodiments of the present invention in which piston 810 has more or less fluid seals than depicted. It should also be noted that growing rod 800 has an end seal 816 that prevents extendible rod 804 from being able to extend too far and decoupling from connector body 806.

Once extendible rod 804 has reached a desired distraction length, extendible rod 804 will be under load pressure. This load pressure will force extendible rod 804 to retract backwards on itself. At this time, spring-loaded ball 812 is forced up a ramp arranged within a recess of on piston 810. This causes ball 812 to press up against the side of fluid connector body 806, thereby stopping any further retraction of extendible rod 804. Once extendible rod 804 has been stopped from retracting on itself, the fluid pressure can be relieved from an access port to empty fluid connector body 806 of the fluid pressure.

The design of growing rod 800 is advantageous because it has a small diameter and is of minimal design complication. Growing rod 800 is also advantageous because the fluid pressure will not be in effect during implantation—that is, fluids and pressure will only be introduced when extendible rod 804 is being extended relative to base rod 802. From this design, growing rod 800 is able to be a passive growth mechanism. As the spine grows, growing rod 800 can be advanced within the patient without the aid of external manipulation. The fact that growing rod 800 can be both passive and manipulative (if required) reduces the need of additional surgeries for the patient.

Figure 10:
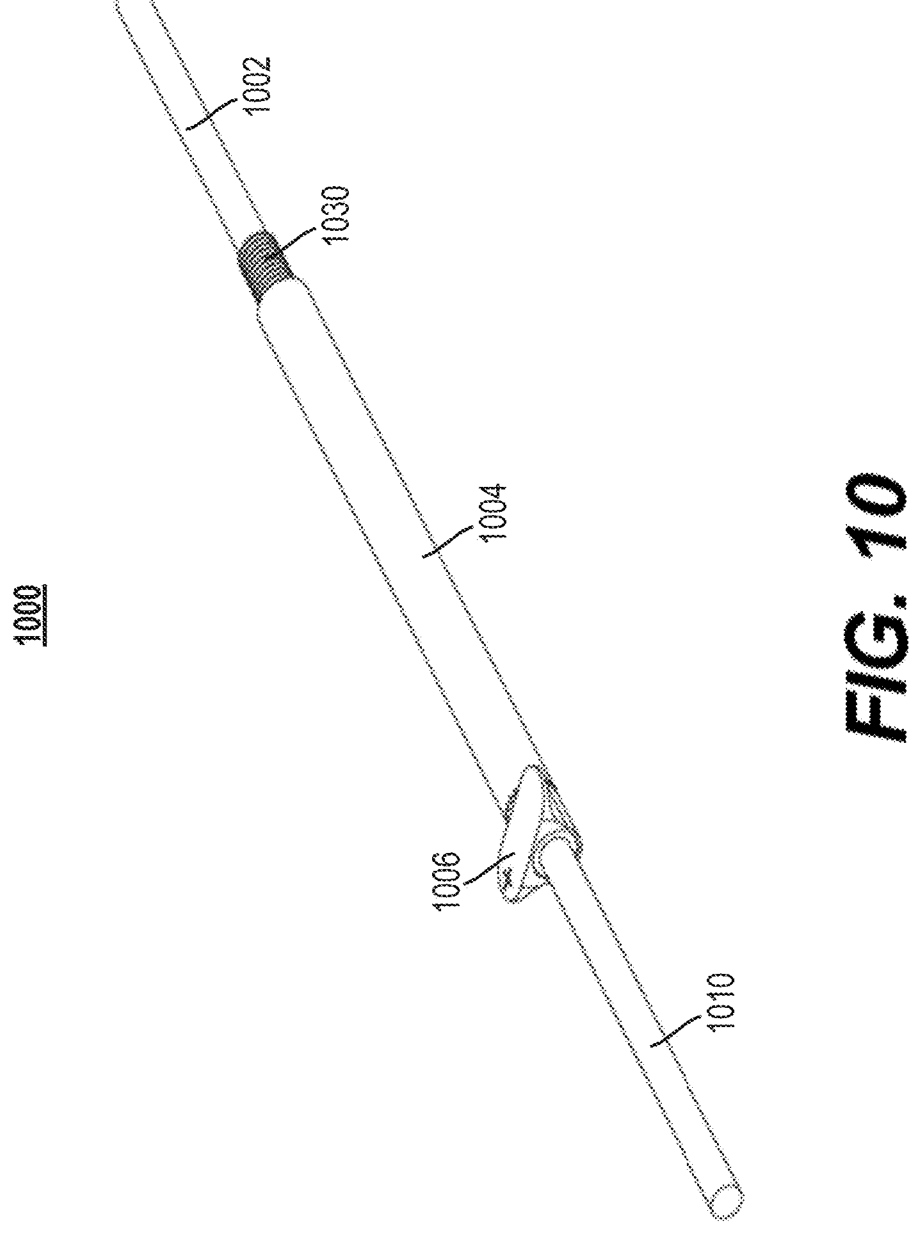
FIG. 10 is a perspective view of a growing rod in accordance with yet another alternative embodiment of the present invention.

FIG. 10 depicts a further alternative embodiment of the present invention. Growing rod 1000 comprises: extendible rod 1002, coupling 1004, toggling switch 1006, spring 1008, and base rod 1010. Each of these elements that form growing rod 1000 can be constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of growing rod 1000 can be made from a durable thermoplastic polymer, such as polyether ether ketone (PEEK).

In accordance with this alternative embodiment, the outer surface of extendible rod 1002 is arranged with threads 1030. Preferably, only a portion of the outer surface of extendible rod 1002 is threaded with threads 1030. However, in other embodiments, the entire length of extendible rod is arranged with threads 1030. The proximal portion of extendible rod 1002 is adapted to be received within and threaded into the distal portion of coupling 1004.

Figure 12:
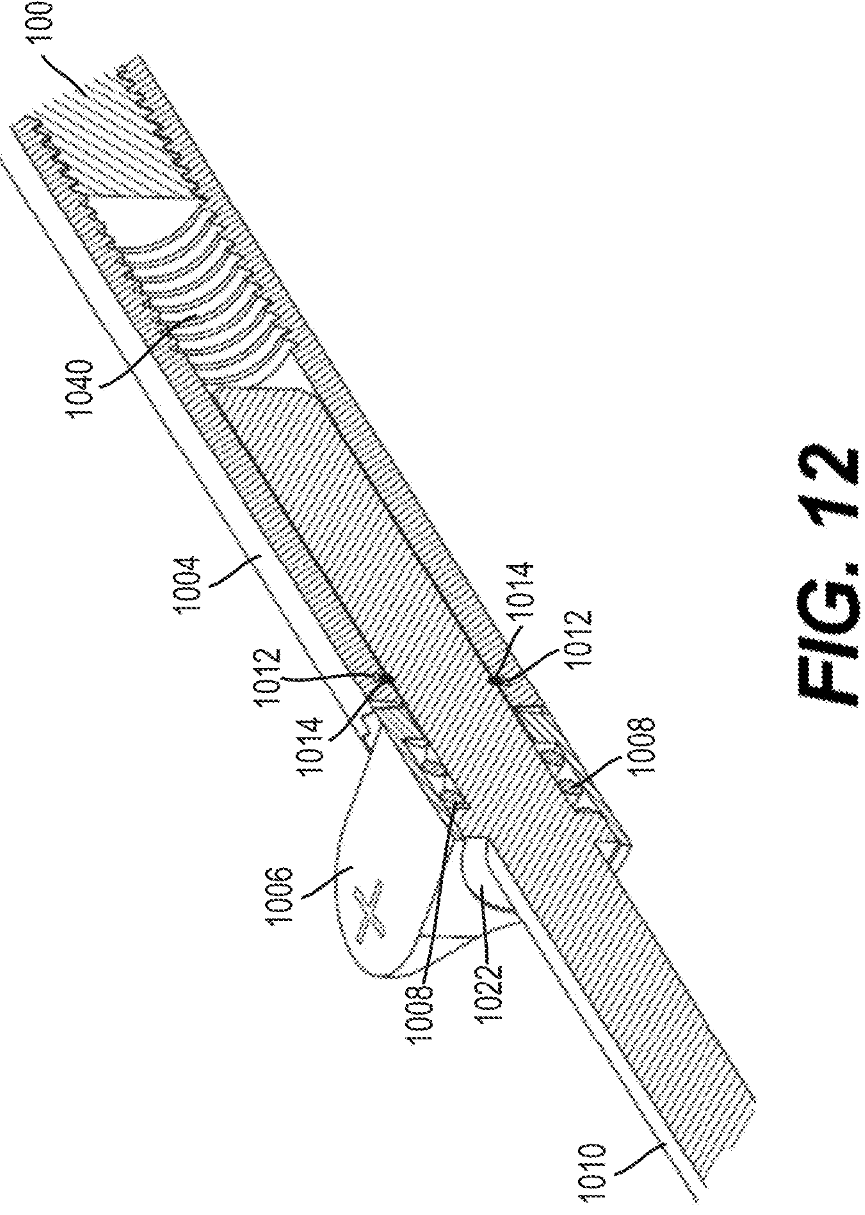
FIG. 12 is a cross-sectional view of the growing rod of FIG. 10.

Coupling 1004 has a through-hole for receiving extendible rod 1002 and base rod 1010. As shown in FIG. 12, the inner surface of the distal portion of coupling 1004 is arranged with threads 1040. These threads of coupling 1004 allow extendible rod 1002 to be received within and threaded into the distal portion of coupling 1004. The inner surface of the proximal portion or intermediate portion of coupling 1004 is arranged with a groove 1012. The groove is adapted to receive a retaining ring 1014 coupled to base rod 1010 for preventing the base rod from being able to slide in and out of the through-hole of coupling 1004.

Figure 11:
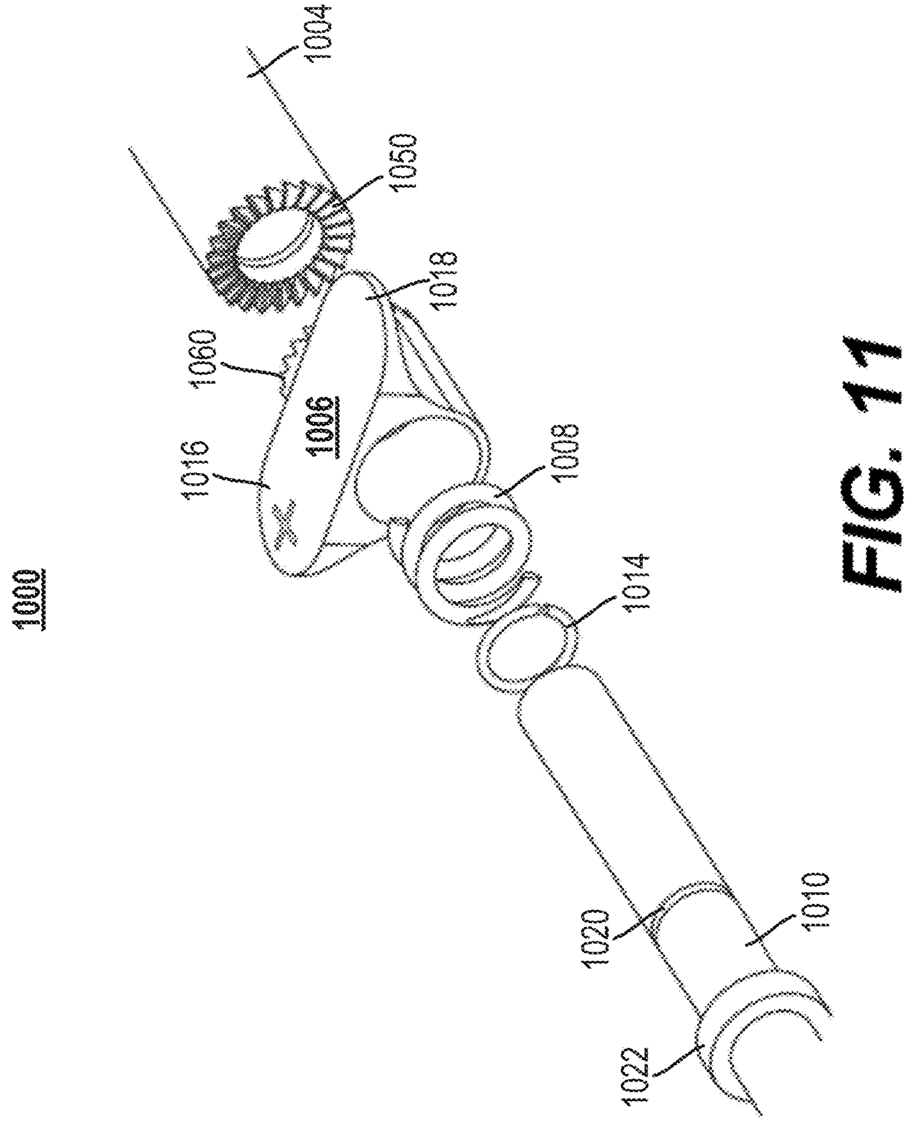
FIG. 11 depicts the elements that form the growing rod of FIG. 10.
Figure 13:
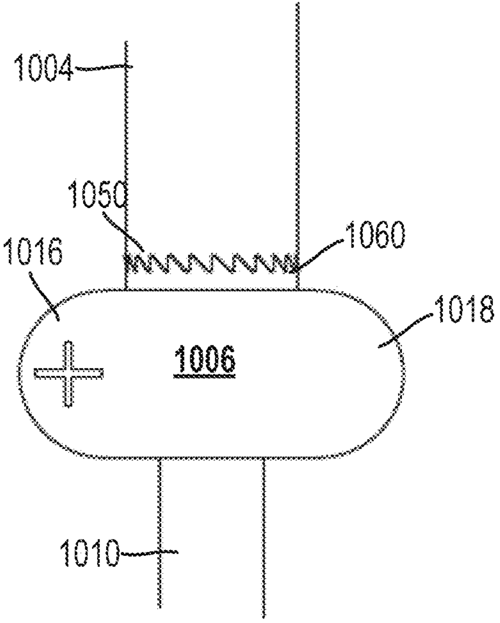
FIG. 13 depicts the one-way, sliding, sawtooth clutch for extending the growing rod of FIG. 10.

As further shown in FIGS. 11 and 13, the proximal portion of coupling 1004 is arranged with teeth 1050 that are adapted to mesh with the teeth 1060 of toggling switch 1006 to form a one-way, sliding, sawtooth clutch. The teeth of coupling 1004 and toggling switch 1006 are chamfers having a symmetrical sloping edge, as shown in the figures. The sloping edge allows teeth 1050 of coupling 1004 to slide along the sloping edge of the teeth 1060 arranged on toggling switch 1006. The angle of the sloping edge of the teeth of elements 1004 and 1006 can be, for example, and without limitation, 10°, 45°, 65°, etc. As will be discussed in more detail below, the one-way, sliding, sawtooth clutch allows coupling 1004 to rotate and cause linear movement of extendible rod 1002.

Toggling switch 1006 is arranged with a through-hole for receiving base rod 1010. The inner surface of the through-hole of toggling switch 1006 has a cutout that is adapted to receive spring 1008. Toggling switch 1006 is also arranged with a first toggle 1016 and a second toggle 1018 that can be operated by a user (e.g., a doctor, nurse, etc.) to cause linear movement of extendible rod 1002 relative to coupling 1004.

The distal portion of base rod 1010 is arranged with a groove 1020 for receiving retaining ring 1014. As discussed above, retaining ring 1014 is adapted to prevent base rod 1010 from being able to slide in and out of the through-hole of coupling 1004 when seated within groove 1012. The proximal portion of base rod 1010 is arranged with a circular protrusion having an underside that is adapted to abut against spring 1008.

The method of using growing rod 1000 will now be described. After growing rod 1000 has been implanted along the spine of a patient, the growing rod will need to be periodically extended to keep up with the patient's growth. Unlike the other embodiments described in this disclosure, this alternative embodiment does not require making any incisions on the patient's back access a mechanism for extending the length of growing rod 1000. Instead, the doctor can simply use his hands and feel where toggling switch 1006 is located underneath the patient's skin on his/her back. Once the doctor has located toggling switch 1006, the first toggle 1016 or the second toggle 1018 can be operated by the doctor to lengthen growing rod 1000. For the purpose of this discussion, and without limitation, the first toggle 1016 will be used to lengthen growing rod 1000.

More specifically, the doctor can press on the first toggle 1016 one or more times on the surface of the patient's skin. This pressing action causes toggling switch 1006 to incrementally rotate in the same direction in which the first toggle 1016 is pressed; for example, in a clockwise direction. As toggling switch 1006 incrementally rotates in a clockwise direction, the teeth 1060 of toggling switch 1006 will abut against the teeth 1050 of coupling 1004, thereby driving the coupling to rotate as well. Because coupling 1004 is threaded to base rod 1002, rotating coupling 1004 in this way causes extendible rod 1002 to back out of the through-hole of the coupling, thus extending the length of growing rod 1000.

However, it should be noted that pressing on the second toggle 1018 will not cause coupling 1004 to rotate in the opposite direction; in other words, a counter-clockwise direction. This is because the teeth 1050 of coupling 1004 and the teeth 1060 of toggling switch 1006 cooperatively form a one-way, sliding, sawtooth clutch. More specifically, as the second toggle 1018 is pressed by the doctor, the sloping edge of the teeth 1060 of toggling switch 1006 slide along the sloping edge of the teeth 1050 of coupling 1004. This causes toggling switch 1006 to be pushed away from coupling 1004 and compress against spring 1008. Spring 1008 is then compressed against the underside of circular protrusion 1022 until the teeth 1060 of toggling switch 1006 is once again meshed with the teeth 1050 of coupling 1004.

As noted above, this alternative embodiment is advantageous in that no incisions are required to extend the growing rod.

Figure 14:
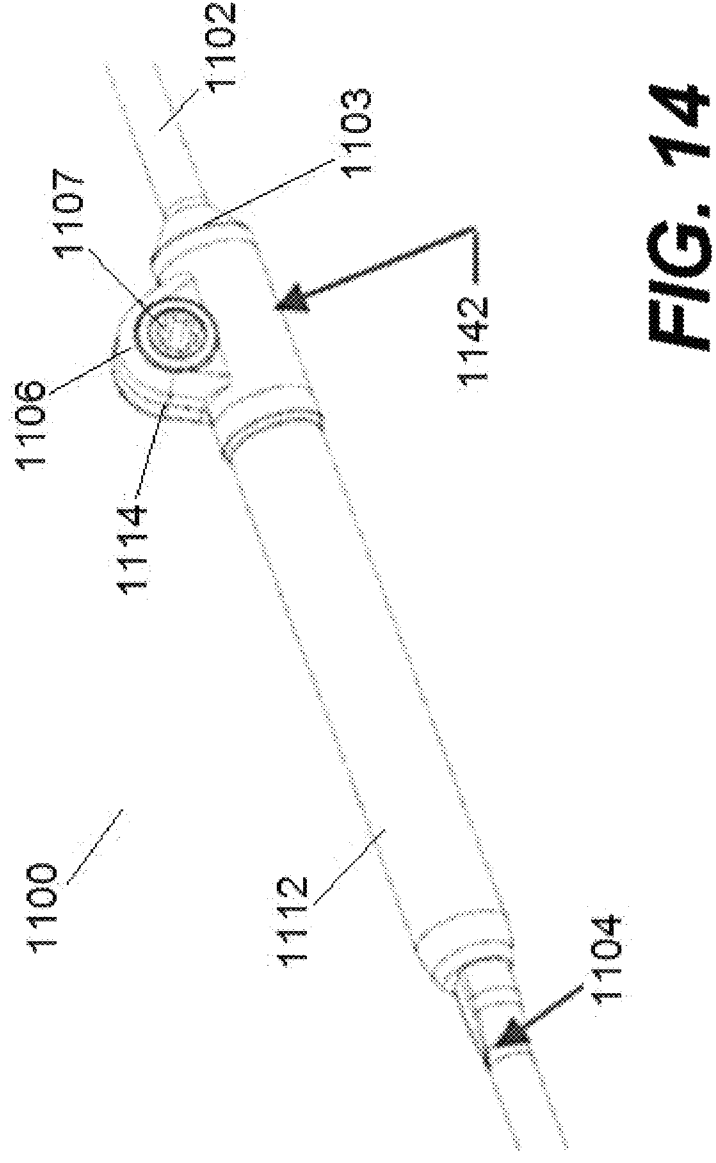
FIG. 14 is a top perspective view of an alternative growing rod in accordance with some embodiments.

FIG. 14 is a top perspective view of an alternative growing rod in accordance with some embodiments. The growing rod 1100 is a manually driven growing rod that advantageously uses a worm gear to extend the length of the growing rod. The advantageous of using such a worm gear is that it prevents inadvertent rotation of any particular gears, thereby reducing the risk of undesired movement of the growing rod.

The growing rod 1100 comprises a fixed rod 1102 and an expansion or extendible rod 1104, wherein the extendible rod 1104 is capable of extending in length away from the fixed rod 1102. The growing rod 1100 further comprises a housing 1112 operably connected to a cover plate 1142 for receiving the fixed rod 1102 and/or extendible rod 1104 therein. The cover plate 1142 is further designed to house one or more gears as part of a gear set 1106 for causing extension and/or retraction of the extendible rod 1104.

As shown in FIG. 14, the growing rod 1100 comprises a fixed rod 1102 and an extendible rod 1104. In some embodiments, the fixed rod 1102 comprises a shaft that is configured to have a fixed length relative to the housing 1112 and/or cover plate 1142. The fixed rod 1102 comprises an end cap 1103 that is operably attached to the cover plate 1142. In contrast, the extendible rod 1104 is configured to have an adjustable length relative to the housing 1112 and/or cover plate 1142. The extendible rod 1104 is capable of expansion via rotation of a rotatable drive interface 1107 in a first direction, and retraction via rotation of the rotatable drive interface 1107 in a second direction opposite the first direction. In some embodiments, the extendible rod 1104 comprises an outer threaded portion (shown as reference numeral 1321 in FIG. 21) that is configured to engage an inner threaded portion of an inner threaded sleeve 1132. This engagement between the threaded portions accommodates lateral movement of the extendible rod 1104 upon rotation of the inner threaded sleeve 1132.

The extendible rod 1104 is received in the hollow shaft of an inner threaded sleeve 1132 (shown in FIG. 15), which itself is received in the hollow shaft of housing 1112. The housing 1112 comprises a hollow body which advantageously encloses a portion of the extendible rod 1104, thereby protecting it from interference with tissue and other objects in the body. On a first end of the housing 1112, an extendible rod 1104 extends there through. On a second end of the housing 1112, a cover plate 1142 is operably attached to the housing 1112. The cover plate 1142 is designed to house and protect a gear set 1106.

In the present embodiment, the gear set 1106 comprises a worm gear set. The worm gear set 1106 comprises a worm in the form of a rotatable drive interface 1107 that is engaged to worm gear 1108 (shown in FIG. 15). Advantageously, a worm gear helps to hold the position of the growing rod 1100 so that it does not inadvertently retract. Rotation of the rotatable drive interface 1107 in a first direction causes rotation of the worm gear 1108 to rotate around a longitudinal axis of the growing rod 1100. The rotatable drive interface 1107 is visible through an eyelid 1114 that is formed in the cover plate 1142 of the growing rod 1100. In some embodiments, the worm gear 1108 is attached to the inner threaded sleeve 1132. In some embodiments, the worm gear 1108 is welded to the inner threaded sleeve 1132. Accordingly, rotation of the rotatable drive interface 1107 in a first direction causes the worm gear 1108 to rotate, which in turn causes rotation of the inner threaded sleeve 1132. As the inner threaded sleeve 1132 is engaged with the extendible rod 1104 via threading, this causes the extendible rod 1104 to translate linearly (e.g., extend or expand). Rotation of the rotatable drive interface 1107 in a second direction causes the worm gear 1108 to rotate in the opposite direction, which in turn causes linear translation of the extendible rod 1104 in an opposite, retracted direction.

Figure 15:
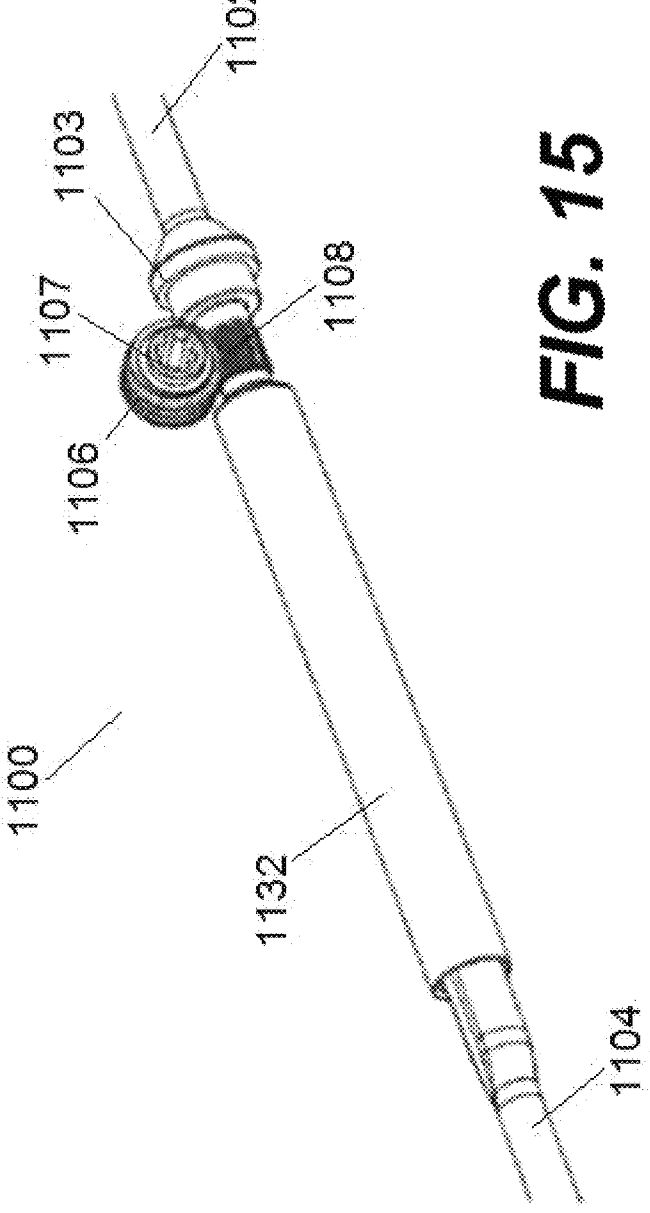
FIG. 15 is a top perspective view of the alternative growing rod of FIG. 14 with portions of the housing removed.

FIG. 15 is a top perspective view of the alternative growing rod of FIG. 14 with portions of the housing removed. In addition to the housing 1112, the cover plate 1142 has also been removed, thereby exposing the gear set 1106. From this view, one can see the inner threaded sleeve 1132 which threadingly engages the threaded portion of the extendible rod 1104. From this view, one can also see how rotation of the rotatable drive interface 1106 causes rotation of the worm gear 1108, which in turn causes rotation of the inner threaded sleeve 1132 and translation of the extendible rod 1104.

Figure 16:
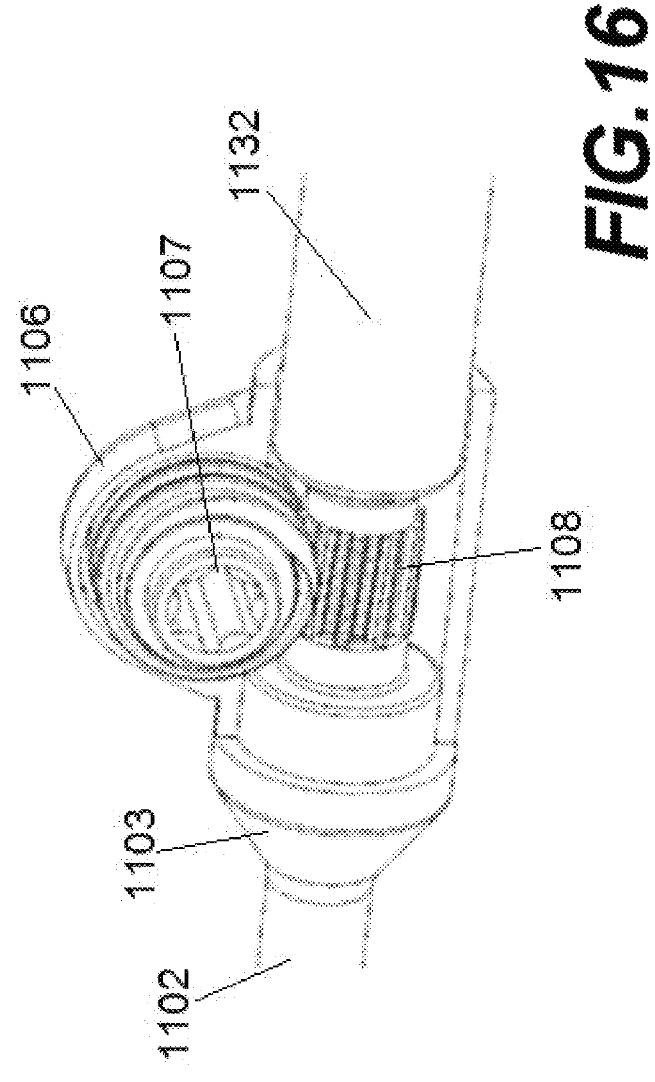
FIG. 16 is a close up view of the gear set of the alternative growing rod of FIG. 14.

FIG. 16 is a close up view of the gear set of the alternative growing rod of FIG. 14. The gear set 1106 comprises a worm gear set including a worm in the form of a rotatable drive interface 1106 and a worm gear 1108. As shown in this figure, the worm gear 1108 is attached to the inner threaded sleeve 1132 (e.g., via welding). As such, rotation of the worm gear 1108 causes rotation of the inner threaded sleeve 1132, which thereby causes linear translation of an extendible rod 1104 therein.

In some embodiments, the growing rod 1100 can incorporate a pre-lordosed housing 1112 and extendible rod 1104. Such a design can also incorporate a flexible inner threaded sleeve 1132. Advantageously, by providing a pre-lordosed growing rod 1100, this removes the flexural forces that can incur between the housing 1112 and extendible rod 1104, and can further allow for more beneficial contouring of the growing rod 1100 to a patient's anatomy.

In some embodiments, the growing rod 1100 can be affixed to a spine via one or more bone screws. The growing rod 1100 can be implanted in either up or down position and can be used singularly or in pairs. In some embodiments, the growing rod 1100 can be engaged through a small incision with a hexalobular drive interface. In some embodiments, the worm gear set 1106 provides a reduction ration of 6:1, 8:1, 10:1 or more. In some embodiments, the worm gear set 1106 provides a reduction ratio of 10:1 such that the rotatable drive interface 1107 is rotated 6 complete revolutions to achieve 1 mm of growing rod 1100 expansion or contraction, with the amount of growth based upon a goal measure of 1.8 cm to 2.4 cm per year. Advantageously, a surgeon can fine tune the amount of expansion by either increasing or decreasing the amount of rotations. If a surgeon feels too much distraction has been incorporated, the growing rod 1100 can be reduced by simply reversing the direction of the driver.

Advantageously, the growing rod 1100 and previous designs can be implanted via use of existing pedicle screws. In some embodiments, the growing rod 1100 will have the strength of a conventional rod, and can be adjusted via minimal incision. Per the worm gear set 1106, a controlled adjustment can be accomplished and distraction forces can be easily met. In some embodiments, the growing rod 1100 can be manufactured using a metal, such as steel, cobalt chrome, or titanium.

Figure 17:
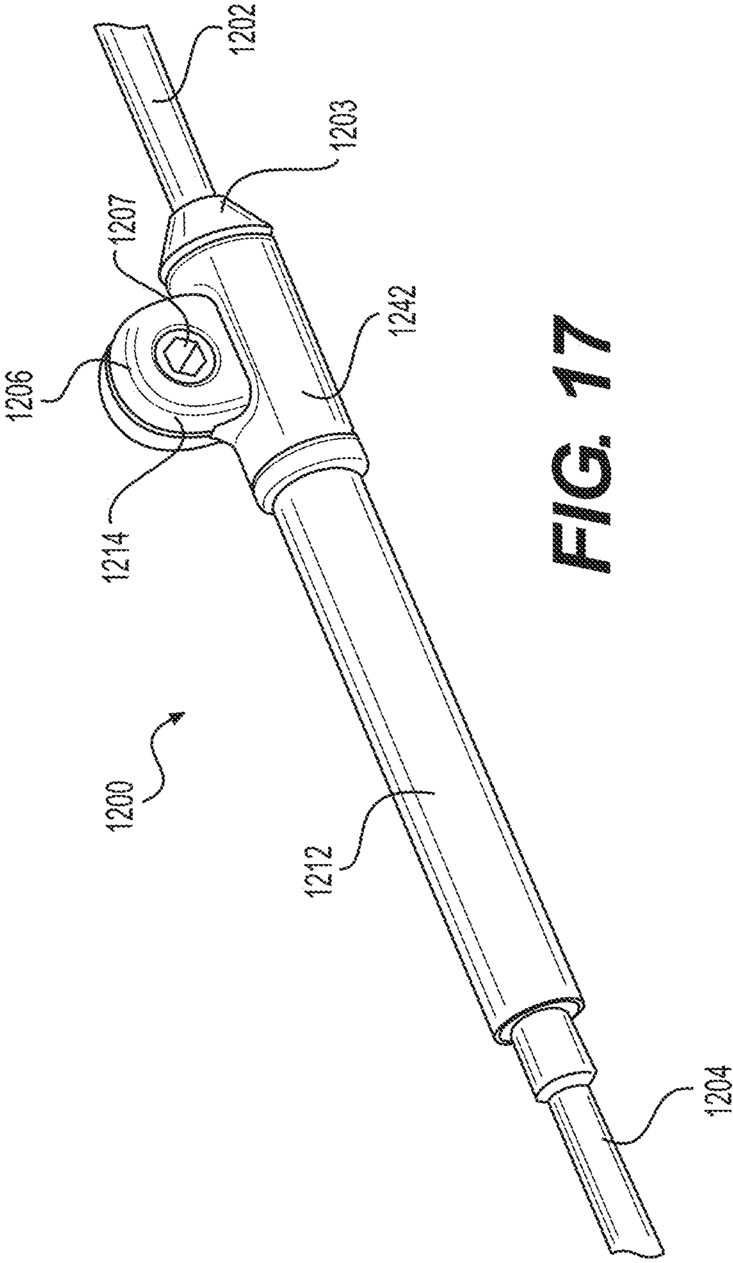
FIG. 17 is a top perspective view of another alternative growing rod in accordance with some embodiments.

FIG. 17 is a top perspective view of another alternative growing rod in accordance with some embodiments. The present growing rod 1200 includes a number of similar features to the growing rod 1100 in FIG. 14, including a fixed rod 1202, an extendible rod 1204, a housing 1212, a cover plate 1242, and a worm gear set 1206. In addition to these features, the growing rod 1200 includes an O-ring cover seal 1219 and a snubber, which will be discussed in more detail below.

The growing rod 1200 comprises a fixed rod 1202 and an extendible rod 1204. In some embodiments, the fixed rod 1202 is fixed relative to the housing 1212 and cover plate 1242, while the extendible rod 1204 is changeable in length relative to the housing 1212 and cover plate 1242. In some embodiments, the fixed rod 1202 comprises an end cap 1203 that is operably connected to the cover plate 1242.

Like the growing rod 1100, the cover plate 1242 of the growing rod 1200 covers a worm gear set 1206. The worm gear set 1206 comprises a rotatable drive interface 1207 that is accessible via a driver through an eyelid 1214 of the cover plate 1242. Rotation of the rotatable drive interface 1207 causes rotation of a worm 1209 (shown in FIG. 18). As the worm 1209 is attached to an inner threaded sleeve 1232 (shown in FIG. 18), it causes the inner threaded sleeve 1232 to rotate. As the extendible rod 1204 is attached to the inner threaded sleeve 1232 by a threaded engagement, it translates laterally, thereby causing expansion or contraction of the extendible rod 1204.

Figure 18:
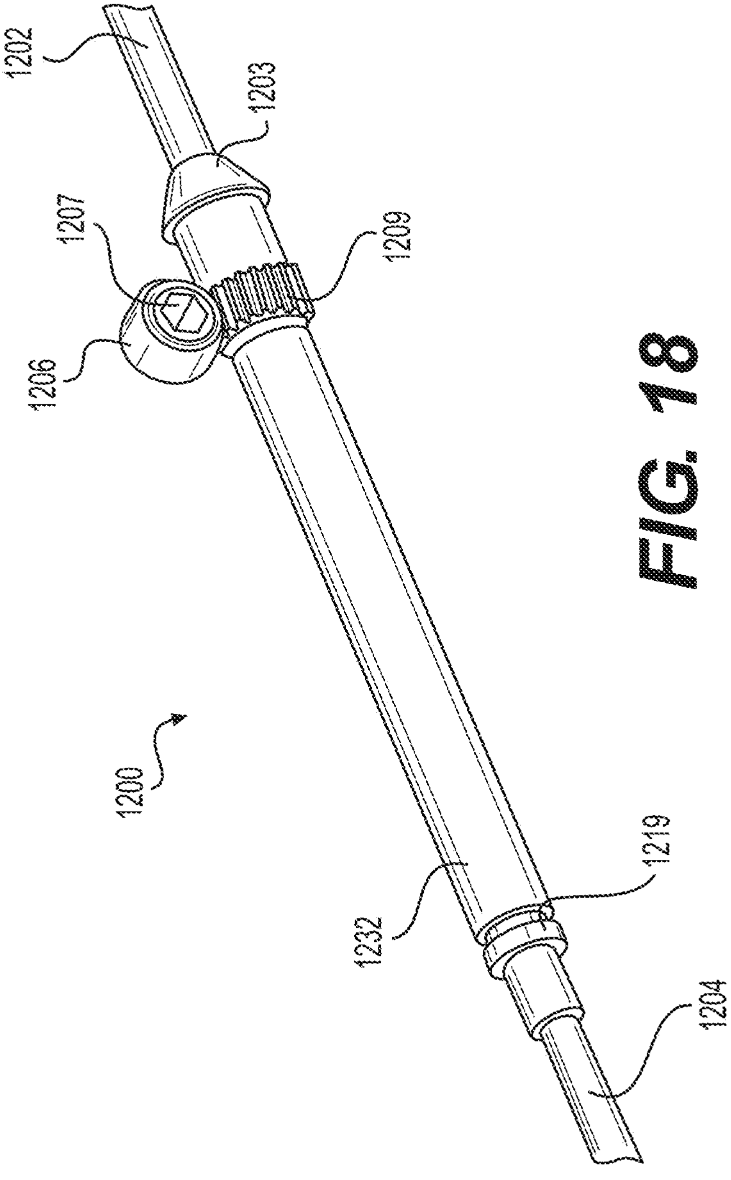
FIG. 18 is a top perspective view of the alternative growing rod of FIG. 17 with portions of the housing removed.

FIG. 18 is a top perspective view of the alternative growing rod of FIG. 17 with portions of the housing removed. From this view, one can see the O-ring cover seal 1219, which extends around the extendible rod 1204. The O-ring cover seal 1219 advantageously helps to seal the housing 1212 from the migration of blood or bodily fluids. In addition, the growing rod 1100 can include an optional snubber that helps to control any backlash from the gear set 1206.

Figure 19:
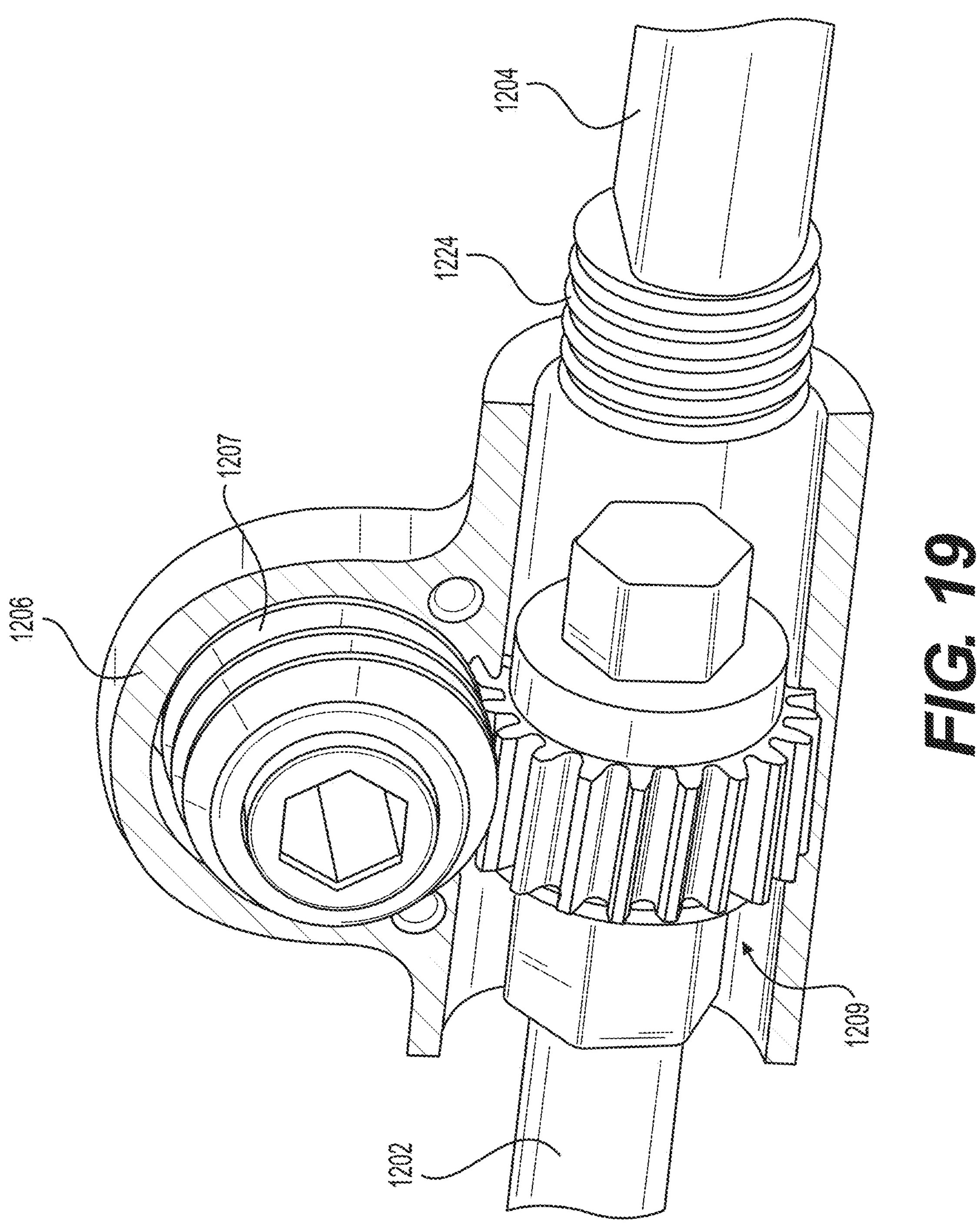
FIG. 19 is a close up view of the gear set of the alternative growing rod of FIG. 17.

FIG. 19 is a close up view of the gear set of the alternative growing rod of FIG. 17. From this view, one can see the worm gear set 1206 which includes the worm in the form of a rotatable drive interface 1207 and the worm gear 1209. In some embodiments, the worm gear 1209 can include a hex portion that is welded to the inner threaded sleeve 1232, which is not visible in FIG. 19. As the worm gear 1209 is attached to the inner threaded sleeve 1232, rotation of the worm gear 1209 causes the inner threaded sleeve 1232 to rotate, thereby causing translation of the extendible rod 1204.

In some embodiments, the growing rod 1200 can incorporate a pre-lordosed housing 1212 and extendible rod 1204. Such a design can also incorporate a flexible inner threaded sleeve 1232. Advantageously, by providing a pre-lordosed growing rod 1200, this removes the flexural forces that can incur between the housing 1212 and extendible rod 1204, and can further allow for more beneficial contouring of the growing rod 1200 to a patient's anatomy.

In some embodiments, the growing rod 1200 can be affixed to a spine via one or more bone screws. The growing rod 1200 can be implanted in either up or down position and can be used singularly or in pairs. In some embodiments, the growing rod 1200 can be engaged through a small incision with a hexalobular, or hex, drive interface. In some embodiments, the worm gear set 1206 provides a reduction ration of 6:1, 8:1, 10:1 or more. In some embodiments, the worm gear set 1206 provides a reduction ratio of 10:1 such that the rotatable drive interface 1207 is rotated 6 complete revolutions to achieve 1 mm of growing rod 1200 expansion or contraction, with the amount of growth based upon a goal measure of 1.8 cm to 2.4 cm per year. Advantageously, a surgeon can fine tune the amount of expansion by either increasing or decreasing the amount of rotations. If a surgeon feels too much distraction has been incorporated, the growing rod 1200 can be reduced by simply reversing the direction of the driver.

Figure 20:
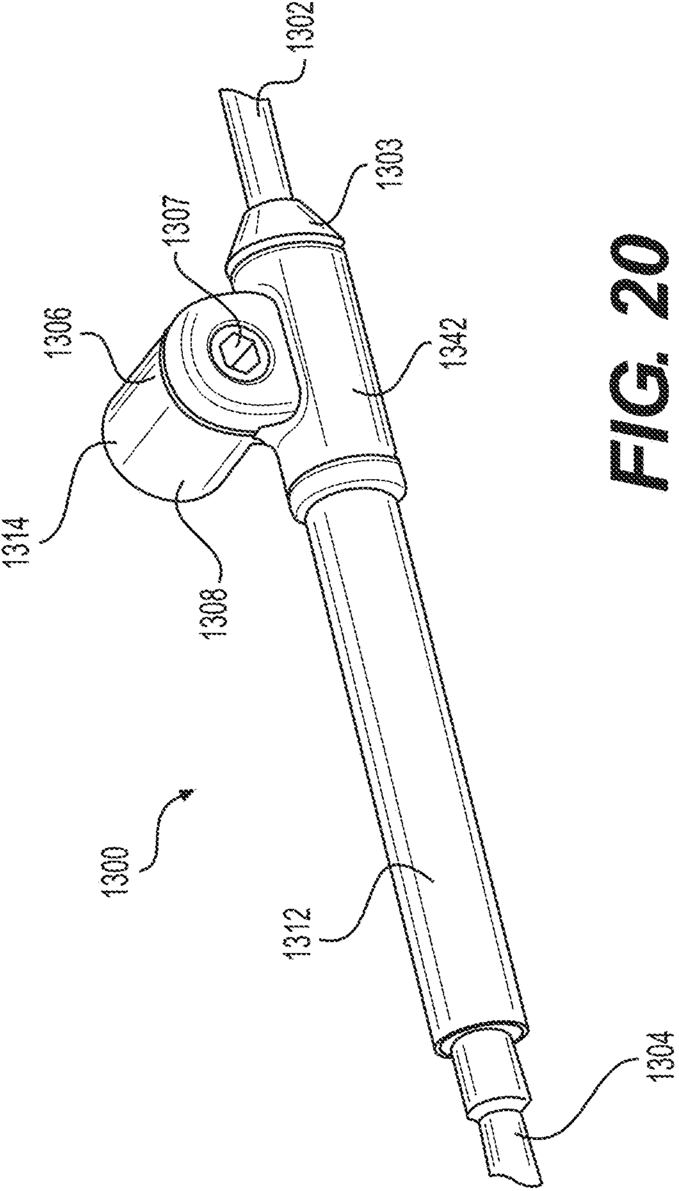
FIG. 20 is a top perspective view of a growing rod including a magnet in accordance with some embodiments.

FIG. 20 is a top perspective view of a growing rod including a magnet in accordance with some embodiments. The growing rod 1300 advantageously comprises a combined magnet and worm gear set 1306 that can extend the length of the growing rod either by an external magnet or via a small incision with a manual driver. The surgeon thus has the option to extend the growing rod via the magnet, manual driver or both options, depending on the needs of a particular patient. In addition to this advantage, the worm gear itself helps to prevent inadvertent rotation (e.g., reverse rotation) of the gear set, thereby providing a stable growing rod 1300. In some embodiments, the growing rod 1300 further includes a planetary reduction gear 1319. The advantage of providing the planetary reduction gear 1319 (shown close up in FIG. 23) is that it provides greater gear reduction per rotation.

The growing rod 1300 comprises a housing 1312 attached to a cover plate 1342. The growing rod 1300 further comprises an extendible rod 1304 extendible through the housing 1312 and a fixed rod 1302. The extendible rod 1304 is capable of extending relative to the housing 1312 and cover plate 1342, while the fixed rod 1302 is fixed relative to these two components. The cover plate 1342 encases the gear set 1306, which in the present case advantageously includes both a magnet 1308 and a worm gear with a rotatable drive interface 1307, as will be discussed in more detail below.

Figure 21:
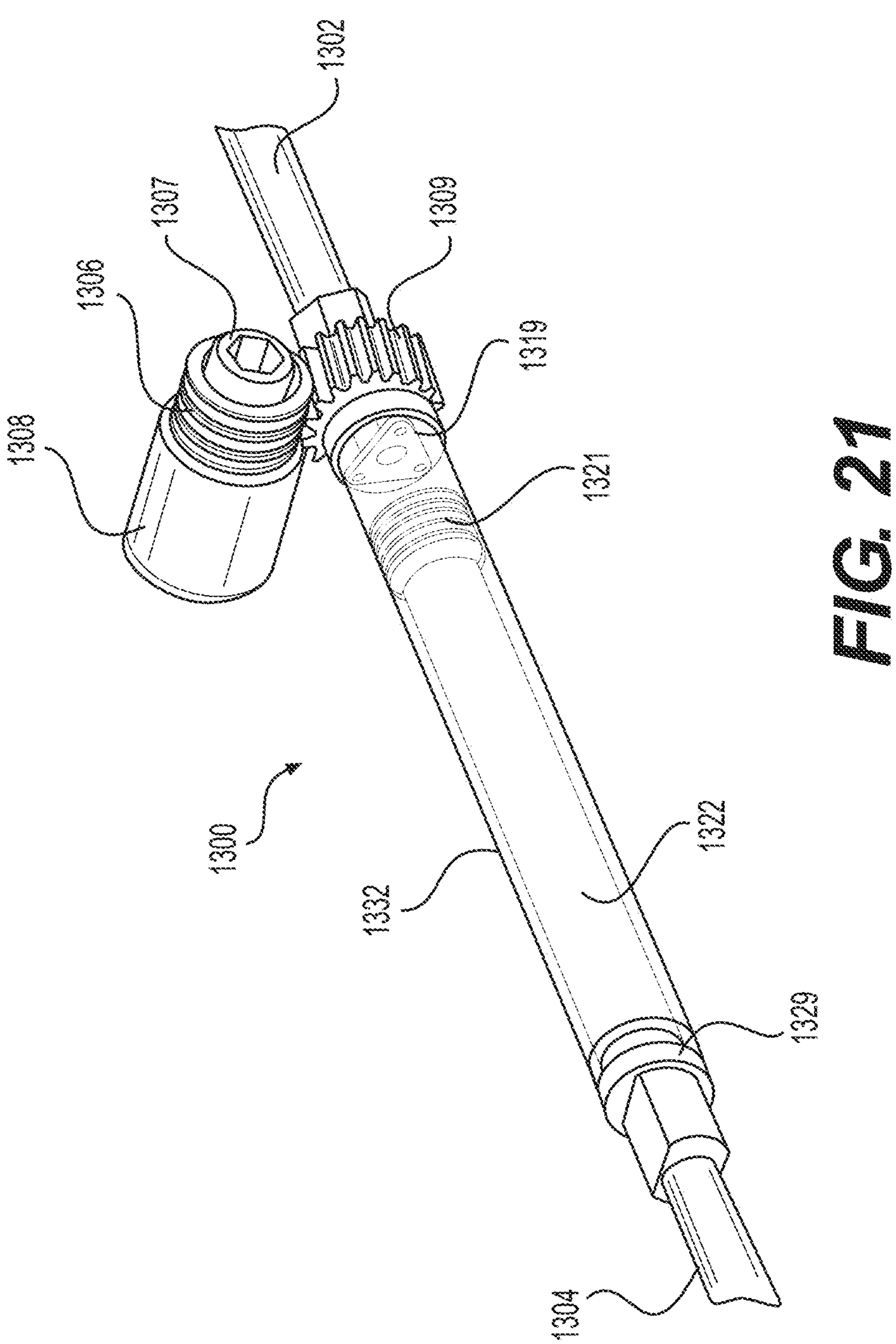
FIG. 21 is a top perspective of the growing rod of FIG. 20 with portions of the housing removed.

FIG. 21 is a top perspective of the growing rod of FIG. 20 with portions of the housing removed. From this view, one can see the inner threaded sleeve 1332 that is received in the housing 1312. In some embodiments, the inner threaded sleeve 1332 has a first end and a second end, wherein the first end is operably attached to the worm gear 1309. In some embodiments, the inner threaded sleeve 1332 is welded to the worm gear 1309. In addition, the inner threaded sleeve 1332 includes inner threads that engage with a threaded portion 1321 formed on the body 1322 of the extendible rod 1304. Advantageously, the worm gear 1307 can be rotated either magnetically or manually via a driver. Rotation of the worm gear 1307 causes the inner threaded sleeve 1332 (to which it is attached) to be rotated. As the extendible rod 1304 is threadingly engaged with the inner threaded sleeve 1332, the extendible rod 1304 will thus rotate and linearly translate, thus allowing the growing rod 1300 to extend in length. Rotation of the worm gear 1307 in an opposite direction causes the extendible rod 1304 to retract.

The gear set 1306 comprises a number of components including a magnet 1308, a worm including a rotatable drive interface 1307, a worm gear 1309 and a planetary gear 1319. The magnet 1308 is designed to extend radially from a longitudinal axis of the growing rod 1300. The magnet 1308 can be engaged via an external magnet that causes rotation of the magnet 1308 and worm 1307. By providing such a magnet, this advantageously provides a means for non-invasive growth of the growing rod 1300. The worm including the rotatable drive interface 1307 comprises an interface that can be engaged by an external driver (e.g., a hex driver). By providing such a rotatable drive interface 1307, this advantageously provides a means for minimally invasive growth of the growing rod 1300. As shown in FIG. 21, the magnet 1308 and the rotatable drive interface 1307 will rotate together, whether via magnet or manual driver. As these components rotate, the worm gear 1309 will also be rotated around the longitudinal axis of the growing rod 1300. As shown in FIG. 21, the worm gear 1309 can be operably attached to the planetary gear 1319. The planetary gear 1319 advantageously allows for greater expansion of the growing rod 1300 with less rotations of the worm gear 1309, thereby allowing the surgeon to expend less work during the procedure. In some embodiments, as shown in FIG. 21, a seal 1329 (e.g., an O-ring seal) can be received over the extendible rod 1304 to seal the housing 1312 from any migration of blood or bodily fluids.

Figure 22:
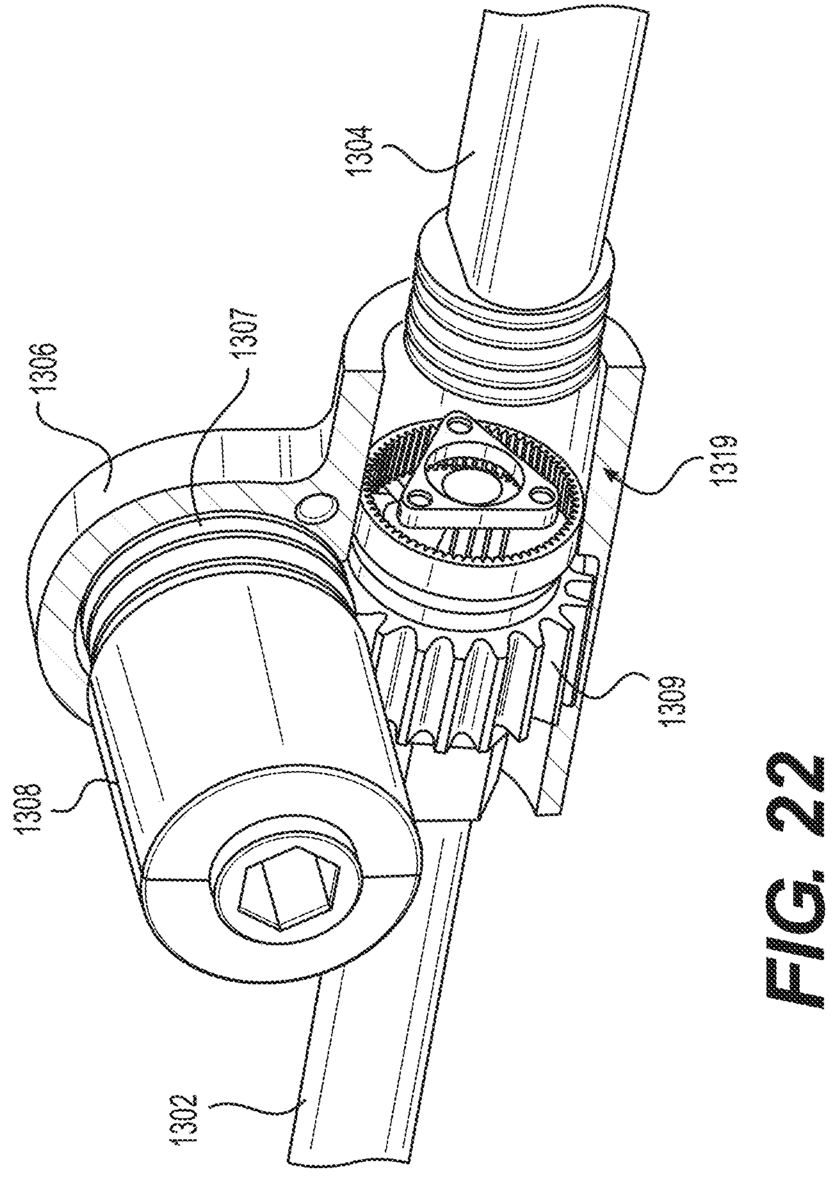
FIG. 22 is a close up view of the gear set of the growing rod of FIG. 19.

FIG. 22 is a close up view of the gear set of the growing rod of FIG. 19. From this view, one can see the magnet 1308, the cover plate eyelid 1306 housing the worm including the rotatable drive interface 1307, the worm gear 1309 and the planetary gear 1319. The worm gear 1309 and/or planetary gear 1319 can be attached to the inner threaded sleeve 1332 (not shown in FIG. 22), which is threadingly engaged with the extendible rod 1304.

Figure 23:
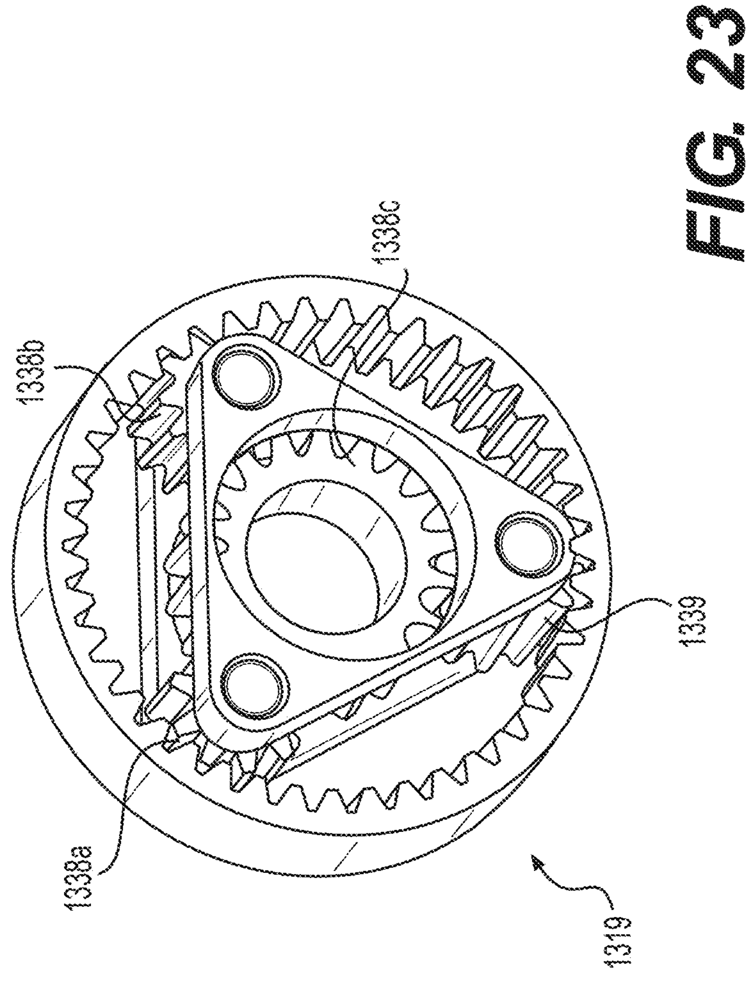
FIG. 23 is a close up view of a planetary gear of the growing rod of FIG. 19.
Figures 24, 25:
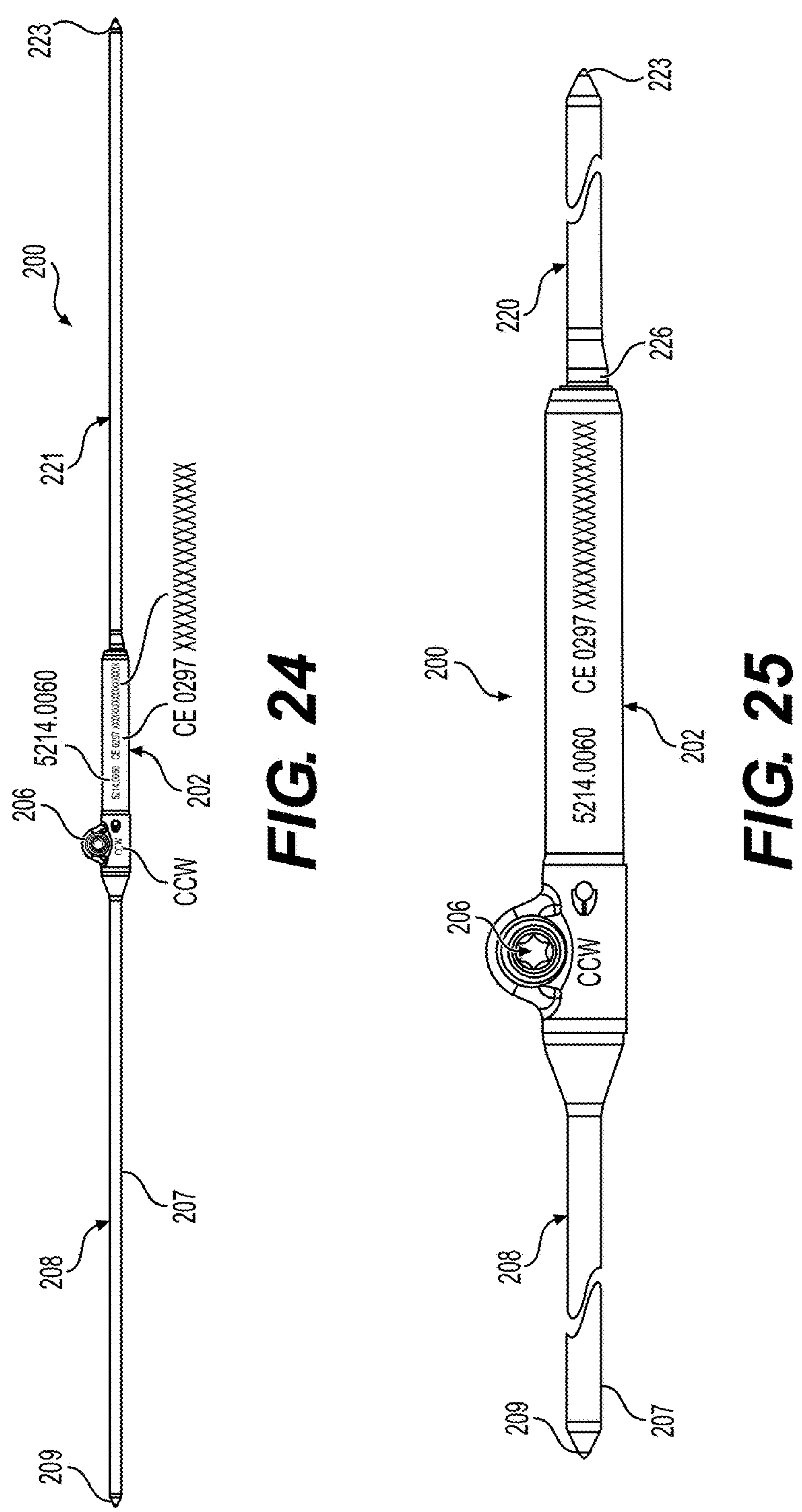
FIG. 24 is a side elevational view of an implantable rod assembly according to an alternative embodiment.
FIG. 25 is an enlarged broken side elevational view of the rod assembly of FIG. 24.

FIG. 23 is a close up view of a planetary gear of the growing rod of FIG. 19. The planetary gear 1319 comprises a gear hub 1339 engaged to a series of miniature gears 1338*a*, 1338*b*, 1338*c*. Rotation of the gear hub 1339 causes the miniature gears 1338*a*, 1338*b*, 1338*c* to rotate, thus causing the overall planetary gear 1319 to rotate.

In some embodiments, the growing rod 1300 can be implanted in either an up or down position and can be used singularly or in pairs. In some embodiments, the magnet 1308 and worm 1306 can be rotated 12, 14, 16, or 18 revolutions to achieve 1 mm of rod expansion or contraction, with the amount based upon a goal measure of 1.8 cm to 2.4 cm per year. The advantage of the growing rod 1300 is that it is designed to be implanted via use of bone screws (e.g., pedicle screws) as would a standard rod. The growing rod 1300 can be adjusted non-invasively with the magnet or via minimal incision. By providing a worm gear 1309 in conjunction with a planetary gear 1319, a controlled adjustment can be accomplished and distraction forces more easily met. In some embodiments, the growing rod 1300 can be made of a metal such as stainless steel, cobalt chrome, or titanium.

Referring now to FIGS. 24-32, a growing rod assembly 200 ("assembly 200") and its implantation into a spinal assembly will now be discussed. The assembly 200 provides a means for spinal lengthening for pediatric patients with early-onset idiopathic & neuromuscular scoliosis. The assembly 200 can provide precise distraction or contraction of the rod for multiple procedures over an extended period of years and can provide greater overall lengthening of rod than other systems. The assembly 200 can accommodate increments and forces to match the growth pattern in scoliosis patients, as well as provide a means of growth through either minimally invasive or external manipulation.

As used with assembly 200, the term "proximal" is defined as a direction toward the free end of the fixed rod 208 and the term "distal" is defined as a direction toward the free end of the expandable rod 220.

Referring to FIGS. 24-26 and 28, the assembly 200 includes a housing 202 in the form of a hollow sleeve. An expansion tube 204 with internal threads 205 is mounted in the housing 202 and extends the length thereof. In an exemplary embodiment, the threaded expansion tube 204 is constructed from a biocompatible titanium alloy.

A housing cap 206 is attached to and is part of the housing 202. A fixed rod 208 extends along a longitudinal axis 201 (shown in FIG. 28) proximally away from the housing 202, such that the housing cap 206 is located between the housing 202 and the fixed rod 208.

In an exemplary embodiment, the fixed rod 208 is constructed from a biocompatible titanium alloy or any other suitable biocompatible material. The fixed rod 208 has a distal end 254 (e.g., a conical distal end 254) that is fixedly connected to the housing cap 206, an elongate body 207 (e.g., a long 4.75 mm diameter cylindrical body 207), and a proximal end 209 (e.g., a pointed proximal tip 209). In an exemplary embodiment, the fixed rod 208 can be laser welded to the housing cap 206 or may be otherwise suitably connected or attached. The body 207 locks into any standard pedicle screw 60. For example, the body 207 may be combined with a pedicle screw 60 that accepts 4.75 mm diameter rods (see FIG. 32). The pointed proximal tip 209 allows the fixed rod 208 to tunnel through tissue when the rod 208 is being passed through the patient during implantation.

Figure 26:
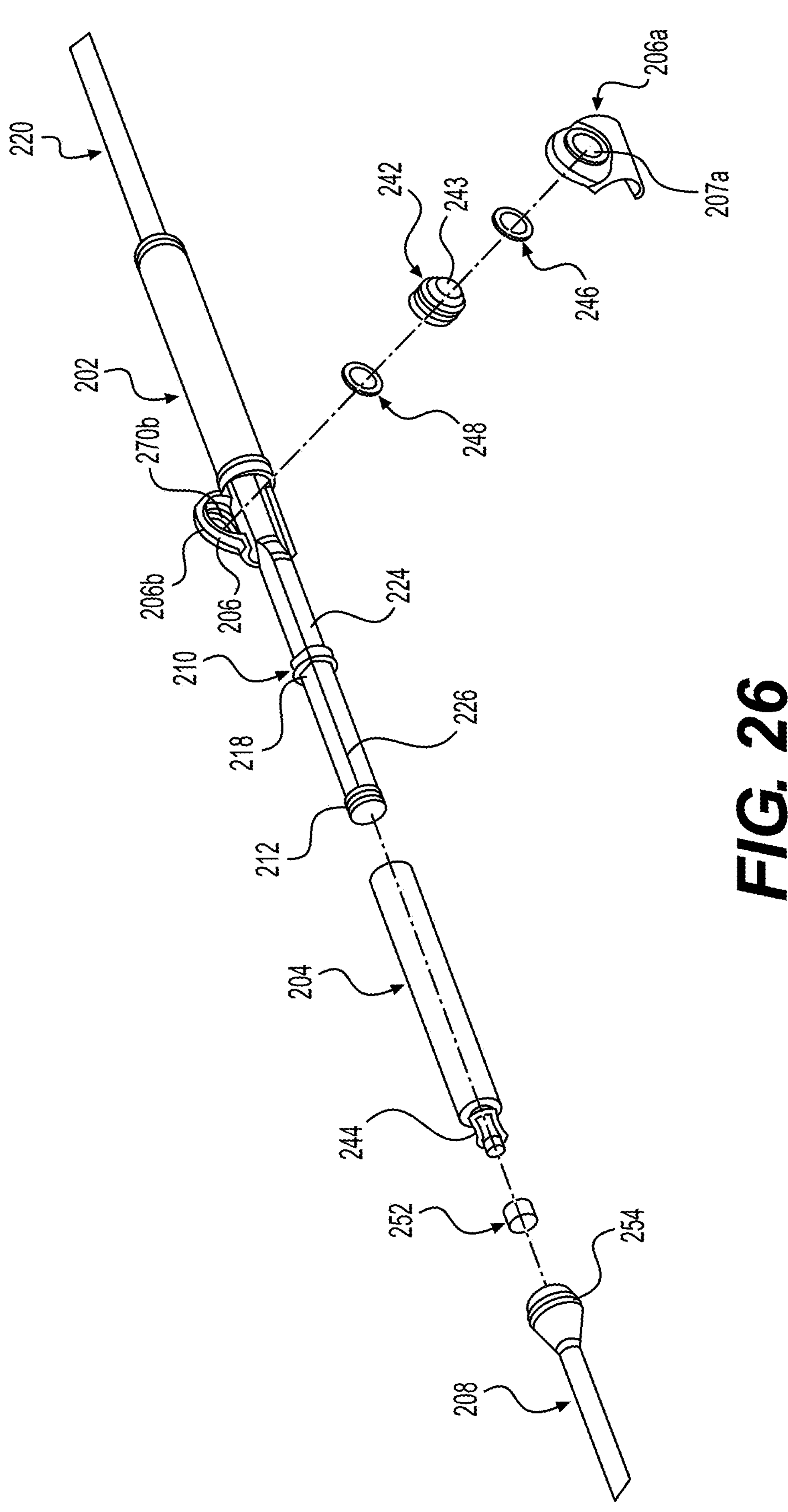
FIG. 26 is an exploded perspective view of the rod assembly of FIG. 24.

As shown in FIG. 26, the housing cap 206 includes first and second portions 206*a*, 206*b* that fit together with a worm drive 242 rotatably mounted between the portions 206*a*, 206*b*. In an exemplary embodiment, the housing 202 and the housing cap 206 are both made of biocompatible titanium alloy that are laser welded together to align and protect the internal components. It is contemplated, however, that suitable materials and modes of connection or attachment may be used. Each of the housing cap portions 206*a*, 206*b* has a through opening 207*a*, 207*b*, respectively, formed therein to allow access to either side of the worm drive 242.

Figures 27, 28:
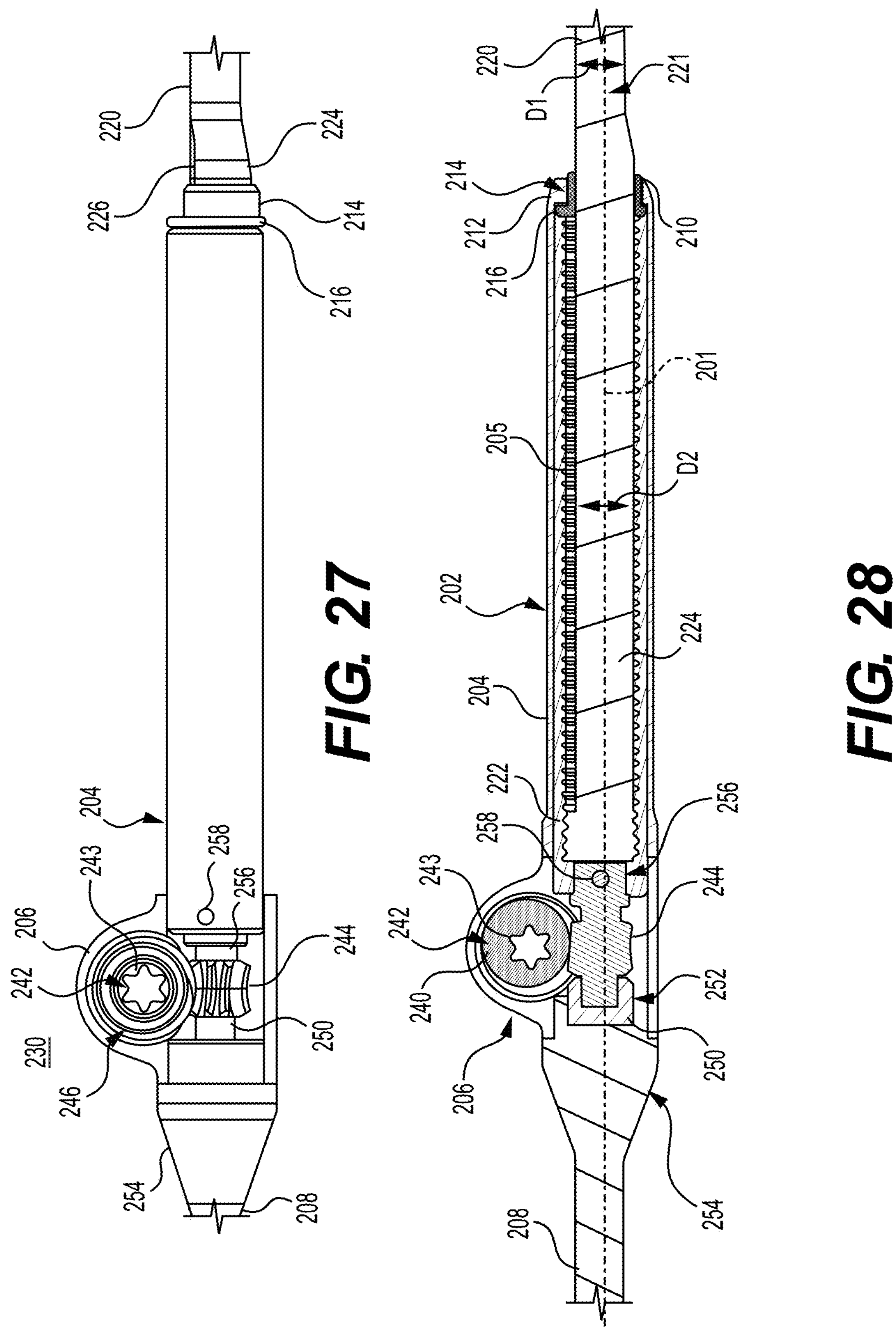
FIG. 27 is an enlarged side elevational view of the rod assembly of FIG. 24, with the housing omitted.
FIG. 28 is a side elevational view, in section, of the rod assembly of FIG. 24, with the extendible rod in a contracted position.

Referring to FIG. 28, a keyed bushing 210 is located in the housing 202 at a distal end 212 of the housing 202. The bushing 210 includes a central body portion 214 that is surrounded by a peripheral flange 216. A keyway 218 (shown in FIG. 26), for example, in the form of a flat surface is formed through the length of the bushing 210. In an exemplary embodiment, the bushing 210 can be constructed from biocompatible PEEK or other suitable materials and also functions to reduce friction and prevent wear between an expansion rod 220 and the housing 202.

The expansion rod 220 is extendible through and from the housing 202 along a longitudinal axis 201. A distal end portion 221 of the expansion rod 220 is adapted to extend outwardly from the distal end 212 of the housing 202. As shown in FIG. 28, the distal end portion 221 has a cylindrical cross-section diameter D1. In an exemplary embodiment, D1 is about 4.75 mm in order to accommodate commercially available pedicle screws that accept 4.75 mm diameter rods (see FIG. 32). Although it is contemplated that D1 may be of any suitable diameter to mate with a corresponding pedicle screw system. The distal end portion 221 is located outside the housing 202 and has a pointed tip 223 (shown in FIG. 25) that allows the tip 223 to tunnel through tissue when the expansion rod 220 is being passed through the patient during implantation.

Figures 29, 30, 31:
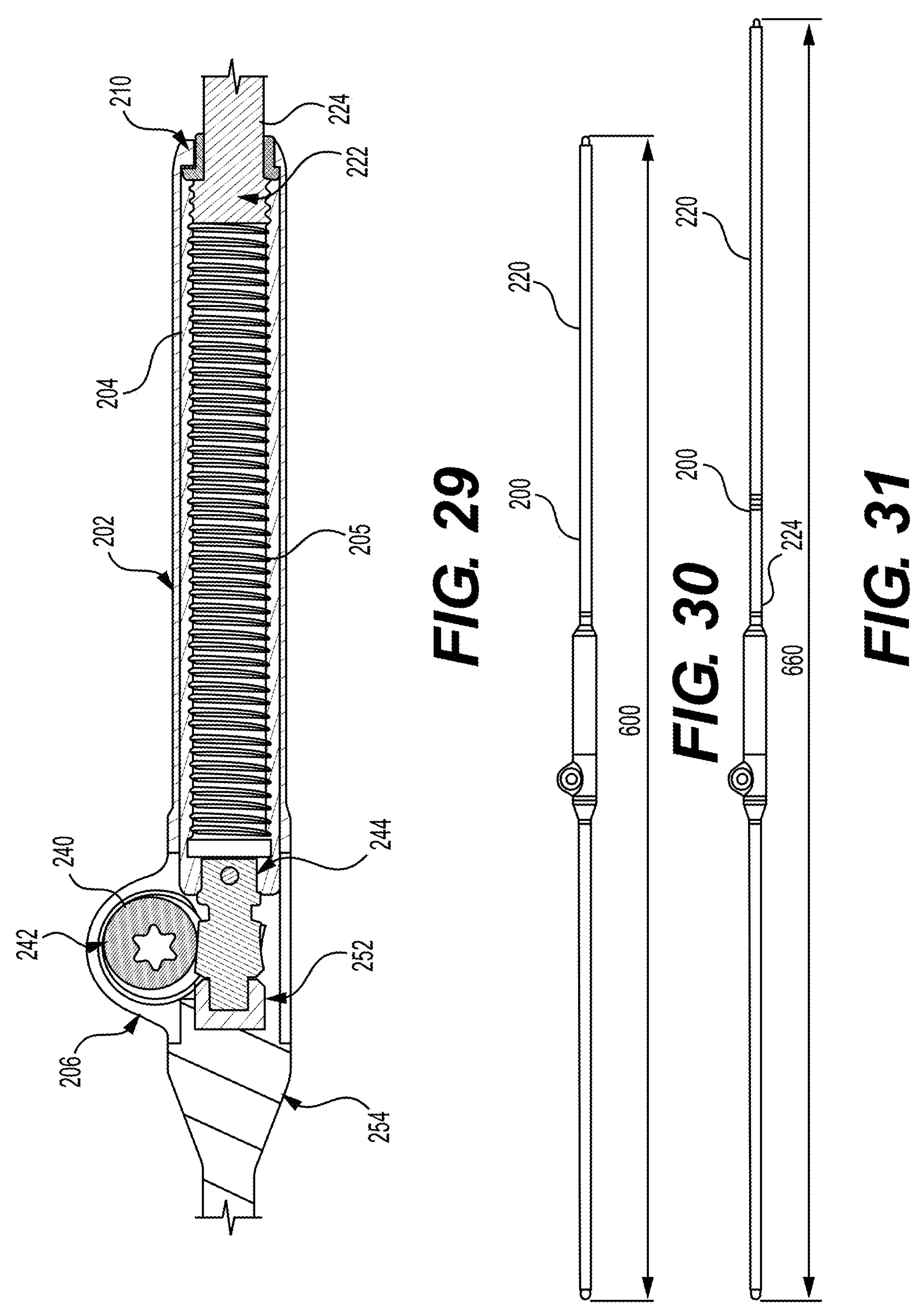
FIG. 29 is a side elevational view, in section, of the rod assembly of FIG. 24, with the extendible rod in an extended position.
FIG. 30 is a side elevational view of the rod assembly of FIG. 24, showing an exemplary contracted length of the rod assembly.
FIG. 31 is a side elevational view of the rod assembly of FIG. 24, showing an exemplary extended length of the rod assembly.

The expansion rod 220 has a threaded proximal end portion 222 that is threadingly engaged with the threads 205 of the internally threaded expansion tube 204. The proximal end portion 222 has a larger diameter than the opening in the bushing 214 so that, when the expansion rod 220 is fully extended, as shown in FIG. 29, the bushing 214 retains the proximal end portion 222 in the housing 202.

A central body portion 224 extends between the proximal end portion 222 and the distal end portion 221. In a fully contracted position, as shown in FIG. 28, at least a portion of the central body portion 224 extends distally of the housing 202. The central body portion 224 has a diameter D2, larger than D1. The larger diameter D2 accommodates a mating key 226, for example, in the form of a flat surface (see FIG. 26) that engages the keyway 218 in the bushing 210 to prevent rotation of the expansion rod 220 as the expansion rod 220 extends out of or contracts into the housing 202. Therefore, as the internally threaded expansion tube 204 rotates, the threaded connection between the internally threaded expansion tube 204 and the threaded proximal end portion 222 of the expansion rod 220 causes the expansion rod 220 to translate longitudinally along the longitudinal axis 201.

Referring to FIG. 28, a driver assembly is disposed in the housing 202 and the housing cap 206 and is adapted to translate, or extend, the expansion rod 220 along the longitudinal axis 201 in a distal direction from the hollow housing 202.

In an exemplary embodiment, the driver assembly comprises a gear mechanism. Further, in an exemplary embodiment, the gear mechanism comprises a right-angle drive gear assembly. In an exemplary embodiment, the right-angle drive assembly comprises a worm gear assembly 240 having a worm drive 242 and a worm gear output 244 rotatable about the longitudinal axis 201. As shown in FIG. 28, the worm gear assembly 240 is located in the housing cap 206 between the housing 202 and the fixed rod 208.

The worm drive 242 is mounted in the housing cap 206 and is supported by worm bushings 246, 248 (shown in FIG. 26), such that one of the worm bushings 246, 248 is mounted on either side of the worm drive 242. In an exemplary embodiment, the worm bushings 246, 248 are constructed from biocompatible PEEK or other suitable material and are used to reduce friction and prevent wear when rotating the worm drive 242. In an exemplary embodiment, the worm drive 242 has a hexalobular drive interface 243 such that a corresponding Torx® wrench driver 70 (shown in FIG. 32) can be used to rotate the worm drive 242. It is contemplated that other suitable drive interfaces 243 and drivers 70 may be selected.

The worm gear output 244 has a proximal end 250 that is rotatably supported by an output gear bushing 252. The output gear bushing 252 is mounted in the distal end 254 of the fixed rod 208, as shown in FIG. 28. The output gear bushing 252 can be constructed from biocompatible PEEK or other suitable material. The gear bushing 252 serves to align the worm gear output 244 with the worm drive 242, reduce friction, and prevent wear between the gear output 244 and the fixed rod 208.

The worm gear output 244 has a distal end 256 that extends into and is fixedly connected to the internally threaded expansion tube 204, such as via a connecting pin 258. In an exemplary embodiment, the connecting pin 258 is constructed from a biocompatible titanium alloy or other suitable material. The expansion tube 204 is connected to the worm gear output 244 such that the expansion tube 204 rotates with the worm gear output 244, thereby translating the expansion rod 220 along the longitudinal axis 201 as the worm gear output 244 rotates, to extend or contract the expansion rod 220 from or into the housing 204 such that the assembly 200 expands or contracts in length, depending on the direction of rotation of the worm drive 242.

The worm gear assembly 240 allows a surgeon to turn the worm drive 242, which causes the expandable rod 220 to extend distally from the housing 202. In an exemplary embodiment, the worm drive 242 and the worm gear output 244 are both made of biocompatible cobalt chrome molybdenum alloy, and are designed with a pitch angle such that the worm drive 242 is able to drive the worm gear output 244, but not the reverse. Friction, as well as the pitch angle, between the worm drive 242 and the worm gear output 244 prevents the worm gear output 244 from rotating the worm drive 242. This feature is known as a self-locking feature and is useful to prevent the expansion rod 220 from expanding or contracting while under forces from the patient's spine without directly engaging the worm drive 242.

Figure 32:
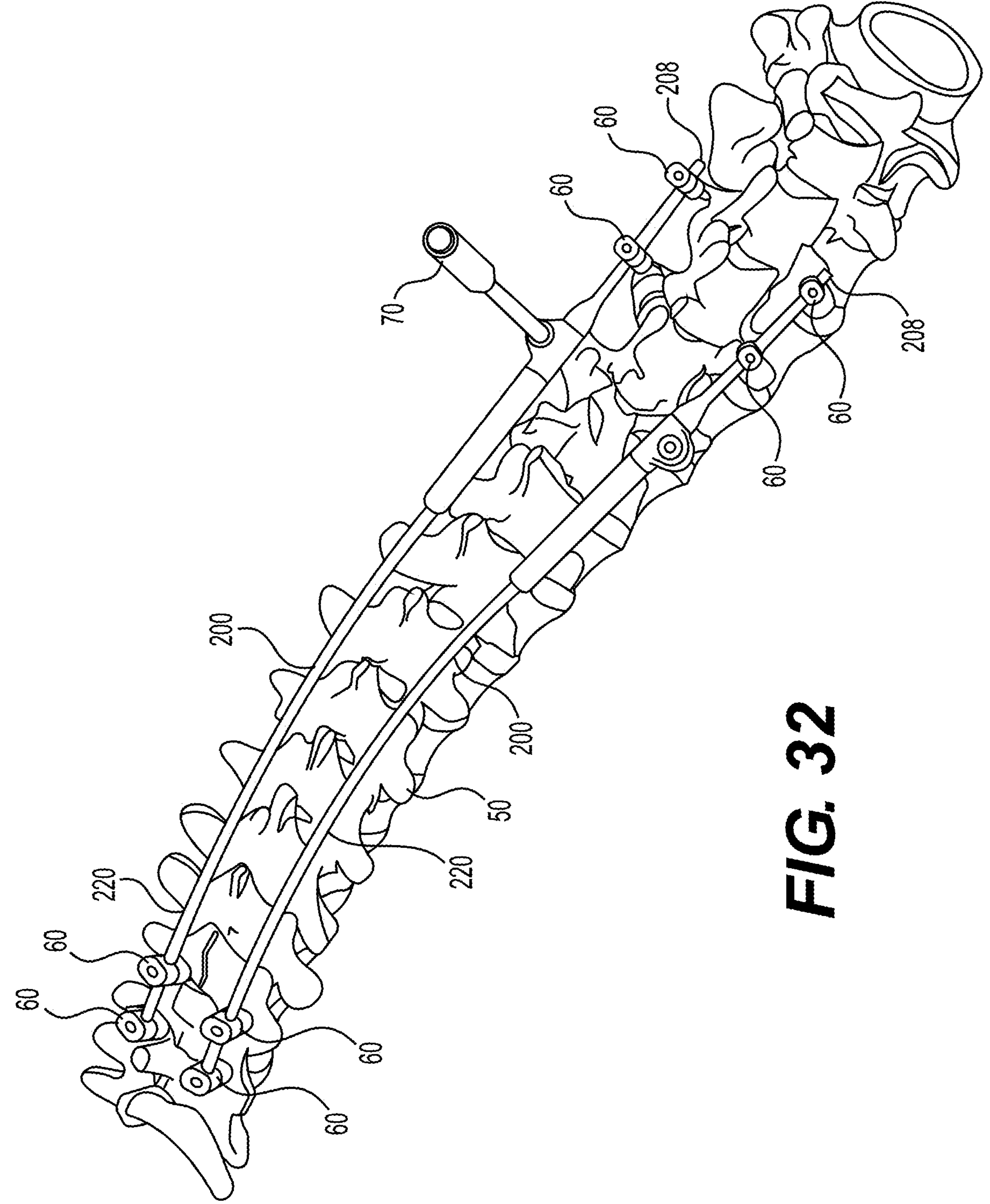
FIG. 32 is a lower perspective view of two rod assemblies of FIG. 24 implanted onto a patient's spinal column.
Figures 33, 34:
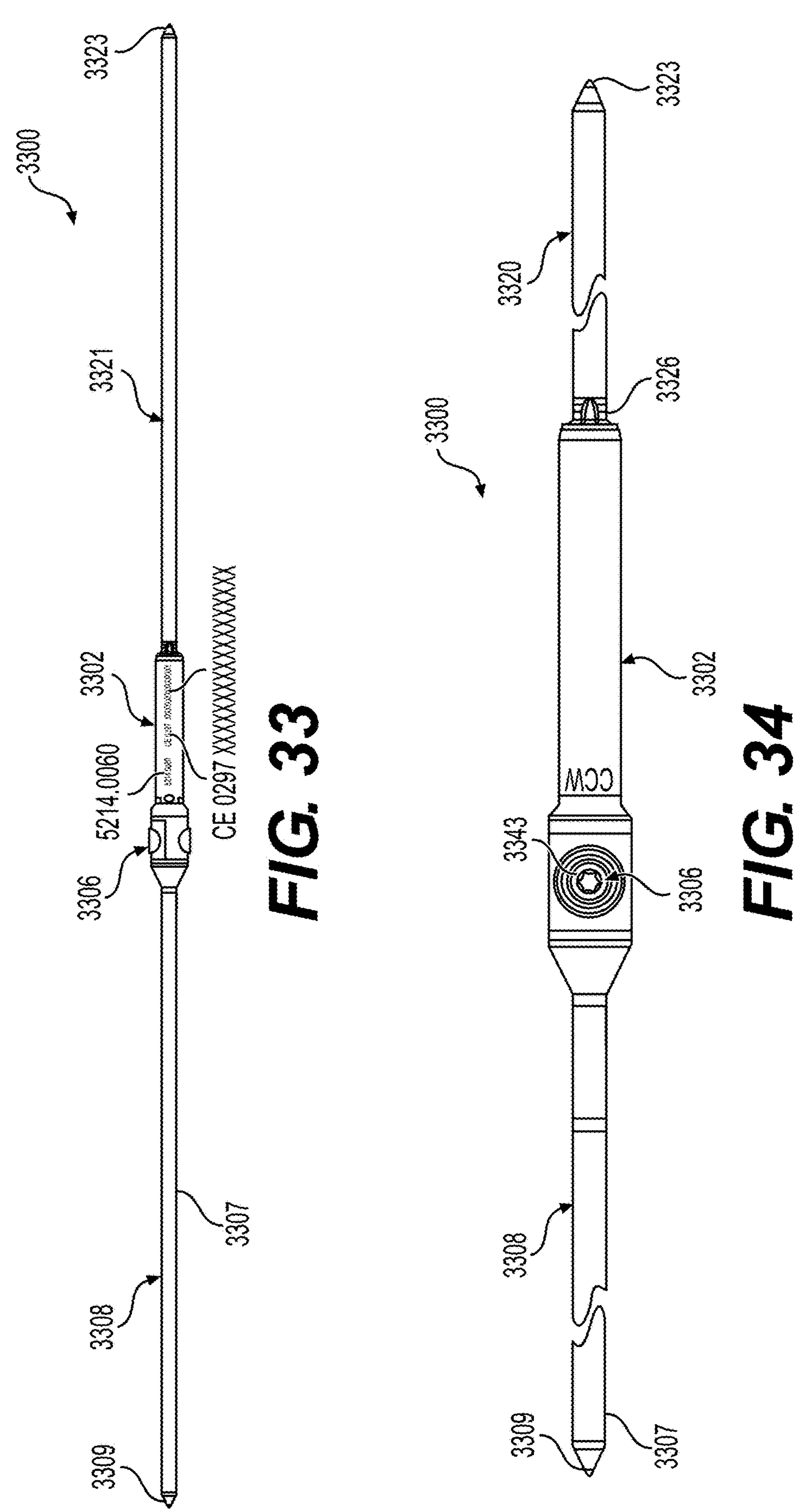
FIG. 33 is a side elevational view of an implantable rod assembly according to an alternative embodiment.
FIG. 34 is an enlarged broken side elevational view of the rod assembly of FIG. 33.

In some embodiments, as shown in FIG. 32, the assembly 200 can be affixed to a spine 50 via one or more pedicle screws 60. The pedicle screws 60 may be in the form of fasteners having a tulip or coupling body such as those described in U.S. Pat. No. 9,750,542, which is incorporated by reference herein. The assembly 200 can be implanted in either up or down position and can be used singularly or in pairs. In some embodiments, the assembly 200 can be engaged through a small incision with the drive interface 243 (e.g., hexalobular drive interface 243). In some embodiments, the worm gear assembly 240 provides a reduction ration of 6:1, 8:1, 10:1 or more. In some embodiments, the worm gear assembly 240 provides a reduction ratio of 10:1 such that for every 10 revolutions of the worm drive 242, the worm gear output 244 rotates one complete revolution. In an exemplary embodiment, the worm drive 242 is rotated about six (6) complete revolutions to achieve between about 1 mm and 1.25 mm of expansion or contraction of the expansion rod 220 from the housing 202, with the amount of growth based upon a goal measure of 1.8 cm to 2.4 cm per year. Advantageously, a surgeon can fine tune the amount of expansion by either increasing or decreasing the amount of rotations. This allows the surgeon to expand the expansion rod 220 against large forces caused by the deformity. If a surgeon feels too much distraction has been incorporated, the assembly 200 can be reduced by simply reversing the direction of the worm drive 242.

Advantageously, the assembly 200 can be implanted via use of existing pedicle screws 60. As shown in FIG. 32, two pedicle screws 60 are used at either end of the assembly 200 on the fixed rod 208 and the expansion rod 220 to secure the assembly 200 to a patient's spinal column 50. After implantation, the assembly 200 is engaged through a small incision via the drive interface 243 of the worm drive 242 with the specified driver 70.

The assembly 200 can be implanted at any position along the spinal column 50 with the expansion rod 220 either caudal or cephalad and can be used singularly or in pairs (as shown in FIG. 32) depending on surgeon discretion. The length of the expansion rods 220 are oversized to allow the surgeon to cut, bend, and customize the expansion rod 220 depending on patient anatomy. The assembly 200 is designed to allow for an estimated minimum of 5 years of growth before replacement or removal is required. As shown in FIG. 30, in an exemplary embodiment, the assembly 200 is 600 mm long with the expansion rod 220 in a fully retracted position, and as shown in FIG. 31, in an exemplary embodiment, the assembly 200 is 660 mm long with the expansion rod 220 in a fully extended position, allowing for up to 60 mm of growth of the patient.

In some embodiments, the assembly 200 will have the strength of a conventional rod, and can be adjusted via minimal incision. By using the worm gear assembly 240, a controlled adjustment can be accomplished and distraction forces can be easily met. In some embodiments, the assembly 200 can be manufactured using a metal, such as steel, cobalt chrome, or titanium or other suitable biocompatible materials.

Referring now to FIGS. 33-39, a growing rod assembly 3300 ("assembly 3300") and its implantation into a spinal assembly will now be discussed. The assembly 3300 provides a means for spinal lengthening for pediatric patients with early-onset idiopathic & neuromuscular scoliosis. The assembly 3300 can provide precise distraction or contraction of the rod for multiple procedures over an extended period of years and can provide greater overall lengthening of rod than other systems. The assembly 3300 can accommodate increments and forces to match the growth pattern in scoliosis patients, as well as provide a means of growth through either minimally invasive or external manipulation.

As used with assembly 3300, the term "proximal" is defined as a direction toward the free end of the fixed rod 3308 and the term "distal" is defined as a direction toward the free end of the expandable rod 3320.

Referring to FIGS. 33-35 and 37A, the assembly 3300 includes a housing 3302 in the form of a hollow sleeve. An expansion tube 3304 with internal threads 305 is mounted within the housing 3302 and extends the length thereof. In an exemplary embodiment, the threaded expansion tube 3304 is constructed from a biocompatible titanium alloy.

A housing cap 4406 is attached to and is part of the housing 4402. A fixed rod 4408 extends along a longitudinal axis 301 (shown in FIG. 37A) proximally away from the housing 3302, such that the housing cap 3306 is located between the housing 3302 and the fixed rod 3308.

In an exemplary embodiment, the fixed rod 3308 is constructed from a biocompatible titanium alloy or any other suitable biocompatible material. The fixed rod 3308 has a distal end 3354 (e.g., a conical distal end 3354) that is fixedly connected to the housing cap 3306, an elongate body 3307 (e.g., a long 4.75 mm diameter cylindrical body 3307), and a proximal end 3309 (e.g., a pointed proximal tip 3309). In an exemplary embodiment, the fixed rod 3308 can be laser welded to the housing cap 3306 or may be otherwise suitably connected or attached. The body 3307 locks into any standard pedicle screw 60. For example, the body 3307 may be combined with a pedicle screw 60 that accepts 4.75 mm diameter rods (see FIG. 39). The pointed proximal tip 3309 allows the fixed rod 3308 to tunnel through tissue when the rod 3308 is being passed through the patient during implantation.

Figure 35:
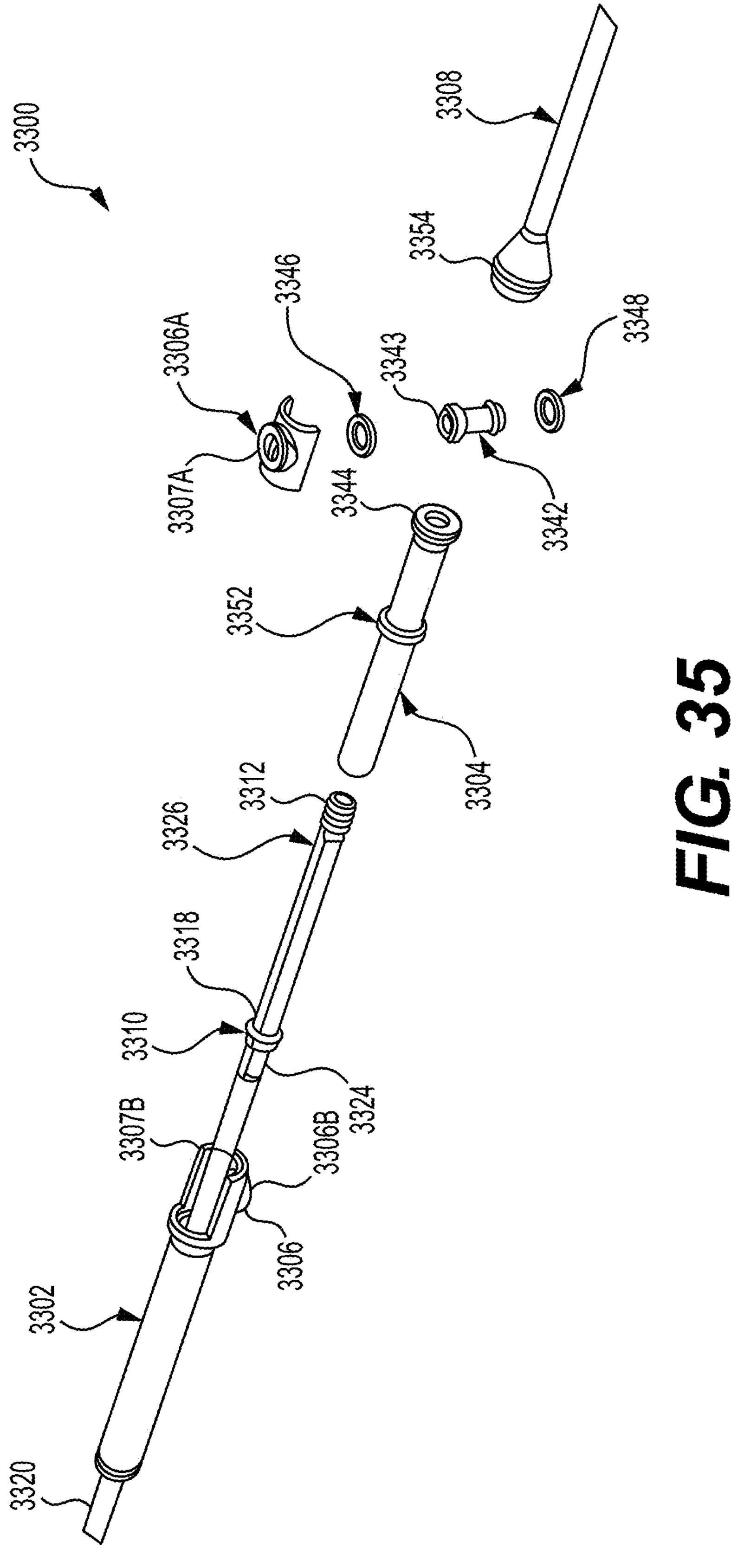
FIG. 35 is an exploded perspective view of the rod assembly of FIG. 33.

As shown in FIG. 35, the housing cap 3306 includes first and second portions 3306A, 3306B that fit together with a bevel pinion gear 3342 rotatably mounted between the portions 3306A, 3306B. In an exemplary embodiment, the housing 3302 and the housing cap 3306 are both made of biocompatible titanium alloy that are laser welded together to align and protect the internal components. It is contemplated, however, that suitable materials and modes of connection or attachment may be used. Each of the housing cap portions 3306A, 3306B has a through opening 3307A, 3307B, respectively, formed therein to allow access to either side of the bevel pinion gear 3342.

Figures 36, 37A:
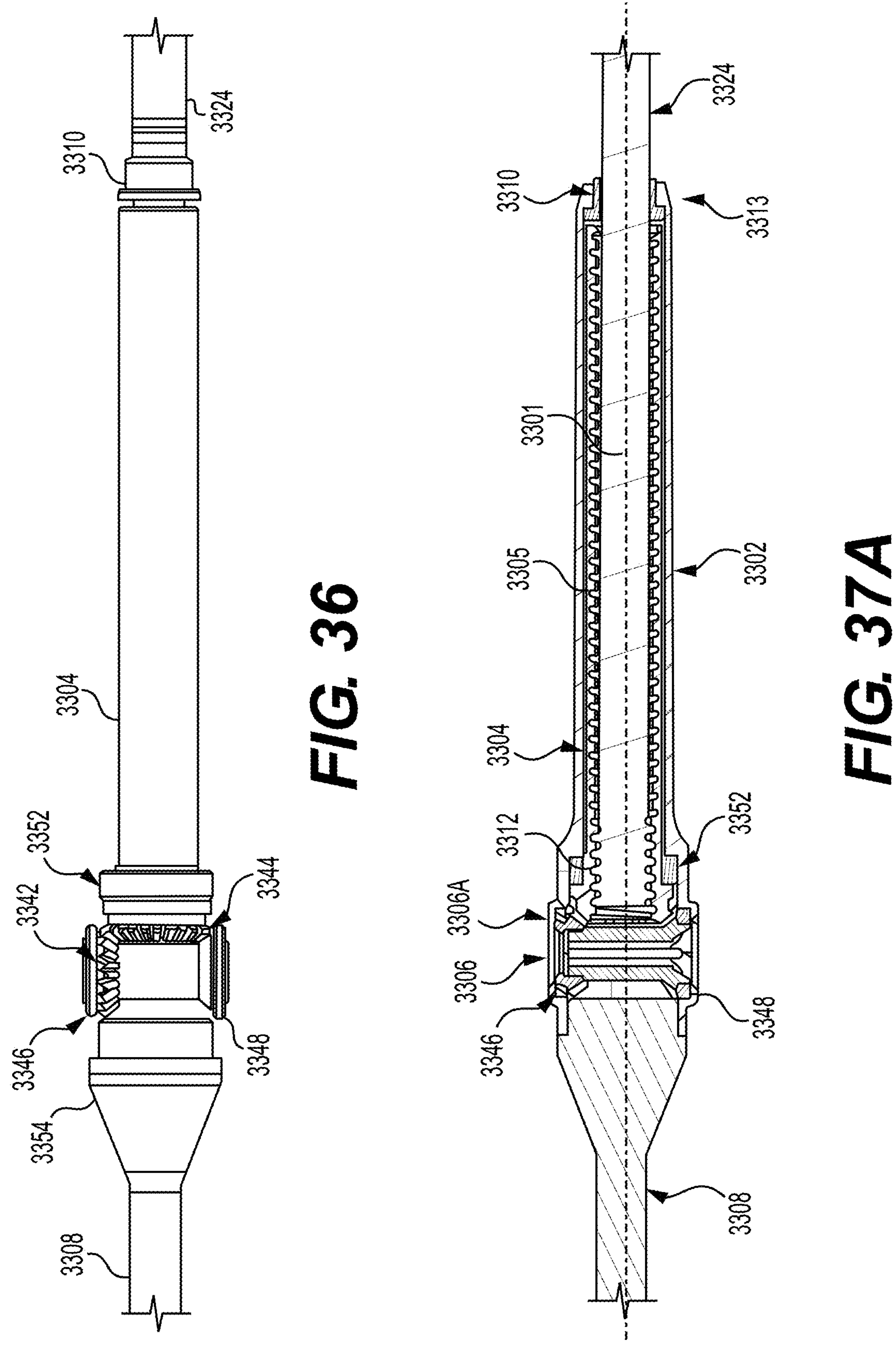
FIG. 36 is an enlarged side elevational view of the rod assembly of FIG. 33, with the housing omitted.
FIG. 37A is a side elevational view, in section, of the rod assembly of FIG. 33, with the extendible rod in a contracted position.

Referring to FIG. 37A, a keyed bushing 3310 is located in the housing 3302 at a distal end 3313 of the housing 3302. The bushing 3310 is substantially similar to the bushing 210 described above. A keyway 3318 (shown in FIG. 35), for example, in the form of a flat surface is formed through the length of the bushing 3310. In an exemplary embodiment, the bushing 3310 can be constructed from biocompatible PEEK or other suitable materials and also functions to reduce friction and prevent wear between an expansion rod 3320 and the housing 3302.

The expansion rod 3320 is extendible through and from the housing 3302 along a longitudinal axis 301. A distal end portion 3321 of the expansion rod 3320 is adapted to extend outwardly from the distal end 3313 of the housing 3302. As shown in FIG. 37A, the distal end portion 3321 has a cylindrical cross-section diameter of about 4.75 mm in order to accommodate commercially available pedicle screws that accept 4.75 mm diameter rods (see FIG. 39). However, it is contemplated that the diameter of the distal end portion 3321 may be any suitable diameter to mate with a corresponding pedicle screw system. The distal end portion 3321 is located outside the housing 3302 and has a pointed tip 3323 (shown in FIGS. 33 and 34) that allows the tip 3323 to tunnel through tissue when the expansion rod 3320 is being passed through the patient during implantation.

Figures 37B, 38A, 38B:
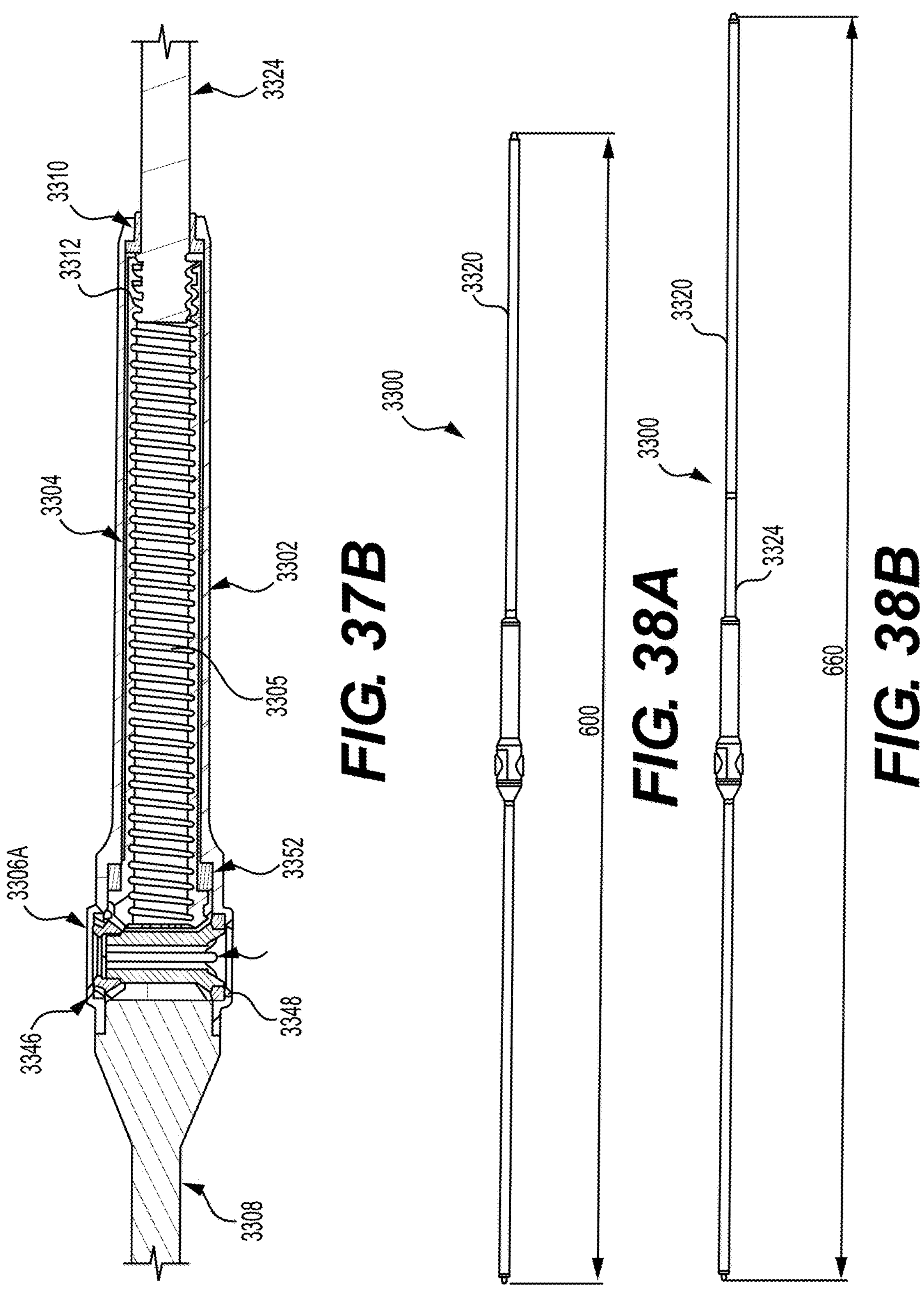
FIG. 37B is a side elevational view, in section, of the rod assembly of FIG. 33, with the extendible rod in an extended position.
FIG. 38A is a side elevational view of the rod assembly of FIG. 33, showing an exemplary contracted length of the rod assembly.
FIG. 38B is a side elevation view of the rod assembly of FIG. 33, showing an exemplary extended length of the rod assembly.

The expansion rod 3320 has a threaded proximal end portion 3312 that is threadingly engaged with the internal threads 305 of the expansion tube 3304. The proximal end portion 3312 has a larger diameter than the opening in the bushing 3310 so that, when the expansion rod 3320 is fully extended, as shown in FIG. 37B, the bushing 3310 retains the proximal end portion 3312 in the housing 3302.

A central body portion 3324 extends between the proximal end portion 3312 and the distal end portion 3321. In a fully contracted position, as shown in FIG. 37A, at least a portion of the central body portion 3324 extends distally of the housing 3302. In some embodiments, the central body portion 3324 may have a diameter larger than the diameter of the distal end portion 3321. The larger diameter is configured to accommodate a mating key 3326, for example, in the form of a flat surface (see FIG. 35) that engages the keyway 3318 in the bushing 3310 to prevent rotation of the expansion rod 3320 as the expansion rod 3320 extends out of or contracts into the housing 3302. Therefore, as the internally threaded expansion tube 3304 rotates, the threaded connection between the internally threaded expansion tube 3304 and the threaded proximal end portion 3312 of the expansion rod 3320 causes the expansion rod 3320 to translate longitudinally along the longitudinal axis 301.

Referring to FIG. 37A, a driver assembly is disposed in the housing 3302 and the housing cap 3306 and is adapted to translate, or extend, the expansion rod 3320 along the longitudinal axis 301 in a distal direction from the hollow housing 3302.

In an exemplary embodiment, the driver assembly comprises a gear mechanism. Further, in an exemplary embodiment, the gear mechanism comprises a right-angle drive gear assembly. In an exemplary embodiment, the right-angle drive assembly comprises a bevel pinion gear 3342 and a bevel output gear 3344 rotatable about the longitudinal axis 301. As shown in FIG. 37A, the gear assembly is located in the housing cap 3306 between the housing 3302 and the fixed rod 3308. The pinion gear 3342 is disposed perpendicularly to the output gear 3344.

The bevel pinion gear 3342 is mounted in the housing cap 3306 and is supported by pinion bushings 3346, 3348 (shown in FIG. 35), such that one of the pinion bushings 3346, 3348 is mounted on either side of the bevel pinion gear 3342. In an exemplary embodiment, the pinion bushings 3346, 3348 are constructed from biocompatible PEEK or other suitable material and are used to reduce friction and prevent wear when rotating the pinion gear 3342. In an exemplary embodiment, the pinion gear 3342 has a hexalobular drive interface 3343 such that a corresponding Torx® wrench driver 70 (shown in FIG. 39) can be used to rotate the pinion gear 3342. It is contemplated that other suitable drive interfaces 3343 and drivers 70 may be selected.

A bevel gear bushing 3352 is disposed between the output gear 3344 and the housing 3302. The bevel gear bushing 3352 can be constructed from biocompatible PEEK or other suitable material. The bevel gear bushing 3352 serves to align the gear output 3344 with the pinion gear 3342, reduce friction, and prevent wear between the output gear 3344 and the housing 3302.

The bevel output gear 3344 forms an end (i.e., is integral with) the internally threaded expansion tube 3304. As a result, the expansion tube 3304 rotates with the bevel output gear 3344, thereby translating the expansion rod 3320 along the longitudinal axis 301 as the bevel output gear 3344 rotates, to extend or contract the expansion rod 3320 from or into the housing 3304 such that the assembly 3300 expands or contracts in length, depending on the direction of rotation of the pinion gear 3342.

The bevel gear assembly allows a surgeon to turn the pinion gear 3342, which causes the expandable rod 3320 to extend distally from the housing 3302. In an exemplary embodiment, the pinion gear 3342 and the bevel output gear 3344 are both made of biocompatible titanium alloy (e.g. TAV), and are designed with a pitch angle such that the pinion gear 3342 is able to drive the bevel output gear 3344.

Figure 39:
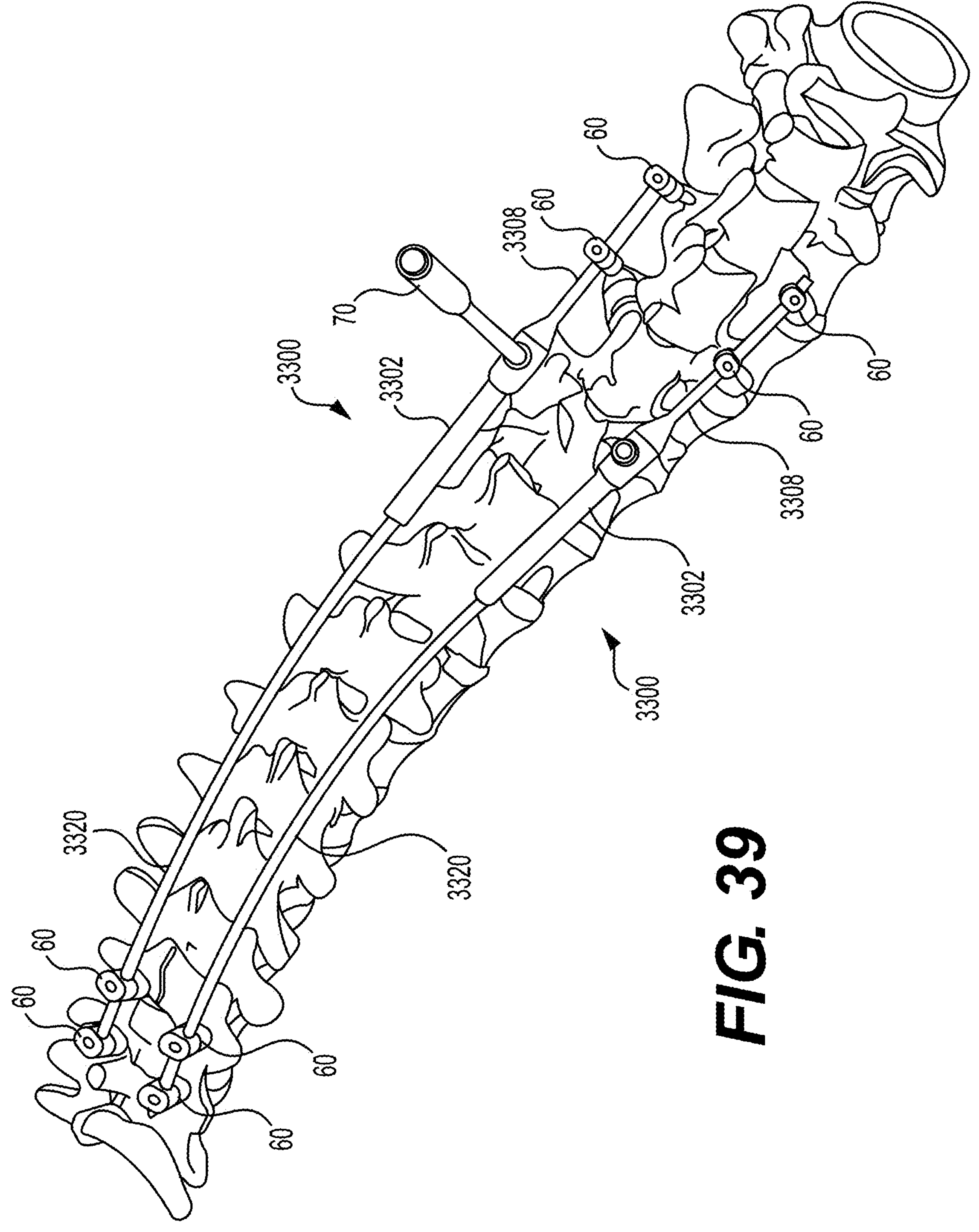
FIG. 39 is a lower perspective view of two rod assemblies of FIG. 33 implanted onto a patient's spinal column.

In some embodiments, as shown in FIG. 39, the assembly 3300 can be affixed to a spine 50 via one or more pedicle screws 60. The pedicle screws 60 may be in the form of fasteners having a tulip or coupling body such as those described in U.S. Pat. No. 9,750,542, which is incorporated by reference herein. The assembly 3300 can be implanted in either up or down position and can be used singularly or in pairs. In some embodiments, the assembly 3300 can be engaged through a small incision with the drive interface 3343 (e.g., hexalobular drive interface 3343). In some embodiments, the bevel gear assembly provides a reduction ration of 1:0.75 or more. In some embodiments, the bevel gear assembly provides a reduction ratio of 1:0.75 such that for every full revolution of the pinion gear 3342, the bevel output gear 3344 rotates 0.75 revolutions. In an exemplary embodiment, the ratio of the pinion teeth to the bevel gear teeth is 15:20. In an exemplary embodiment, the pinion gear 3342 is rotated about one (1) complete revolution to achieve between about 1 mm and 1.25 mm of expansion or contraction of the expansion rod 3320 from the housing 3302, with the amount of growth based upon a goal measure of 1.8 cm to 2.4 cm per year. Advantageously, a surgeon can fine tune the amount of expansion by either increasing or decreasing the amount of rotations. This allows the surgeon to expand the expansion rod 3320 against large forces caused by the deformity. If a surgeon feels too much distraction has been incorporated, the assembly 3300 can be reduced by simply reversing the direction the pinion gear 3342 is turned.

Advantageously, the assembly 3300 can be implanted via use of existing pedicle screws 60. As shown in FIG. 39, two pedicle screws 60 are used at either end of the assembly 3300 on the fixed rod 3308 and the expansion rod 3320 to secure the assembly 3300 to a patient's spinal column 50. After implantation, the assembly 3300 is engaged through a small incision via the drive interface 3343 of the pinion gear 3342 with the specified driver 70.

The assembly 3300 can be implanted at any position along the spinal column 50 with the expansion rod 3320 either caudal or cephalad and can be used singularly or in pairs (as shown in FIG. 39) depending on surgeon discretion. The length of the expansion rods 3320 are oversized to allow the surgeon to cut, bend, and customize the expansion rod 3320 depending on patient anatomy. The assembly 3300 is designed to allow for an estimated minimum of 5 years of growth before replacement or removal is required. As shown in FIG. 38A, in an exemplary embodiment, the assembly 3300 is 600 mm long with the expansion rod 3320 in a fully retracted position, and as shown in FIG. 38B, in an exemplary embodiment, the assembly 3300 is 660 mm long with the expansion rod 3320 in a fully extended position, allowing for up to 60 mm of growth of the patient.

In some embodiments, the assembly 3300 will have the strength of a conventional rod, and can be adjusted via minimal incision. By using the bevel gear assembly, a controlled adjustment can be accomplished and distraction forces can be easily met. In some embodiments, the assembly 3300 can be manufactured using a metal, such as steel, cobalt chrome, or titanium or other suitable biocompatible materials. The use of a bevel gear assembly as described also advantageously provides more low profile assembly compared with other assemblies. For example, if the surgeon desires to implant an assembly with as low a profile as possible, the assembly 3300 provides a lower profile than the assembly 200 due to the utilization of a bevel gear assembly as opposed to a worm gear assembly because the housing required for the bevel gear assembly (See FIG. 34) is smaller than the housing required for the worm gear assembly (See FIG. 25).

Referring now to FIGS. 40-42B, a growing rod assembly 4400 ("assembly 4400") in accordance with embodiments of the present disclosure and its implantation into a spinal assembly will now be discussed. The assembly 4400 is substantially similar to the assembly 3300 discussed above. As such, a discussion of many of the similar aspects will be limited here for brevity.

Referring to FIGS. 40-42B, the assembly 4400 includes a housing 4402 in the form of a hollow sleeve. An expansion tube 4404 with internal threads 4405 is mounted within the housing 4402 and extends the length thereof. In an exemplary embodiment, the threaded expansion tube 4404 is constructed from biocompatible polyether ether ketone (PEEK) to advantageously reduce metallic wear debris resulting from metal on metal contact and improve the imaging capability of the assembly 4400.

A housing cap 4406 is attached to and is part of the housing 4402. A fixed rod 4408 extends along a longitudinal axis 4401 (shown in FIG. 42A) proximally away from the housing 4402, such that the housing cap 4406 is located between the housing 4402 and the fixed rod 4408.

In an exemplary embodiment, the fixed rod 4408 is constructed from a biocompatible titanium alloy or any other suitable biocompatible material. The fixed rod 4408 has a distal end 4454 (e.g., a conical distal end 4454) that is fixedly connected to the housing cap 4406, an elongate body 4407 (e.g., a long 4.75 mm diameter cylindrical body 4407), and a proximal end 4409 (e.g., a pointed proximal tip 4409).

Figure 40:
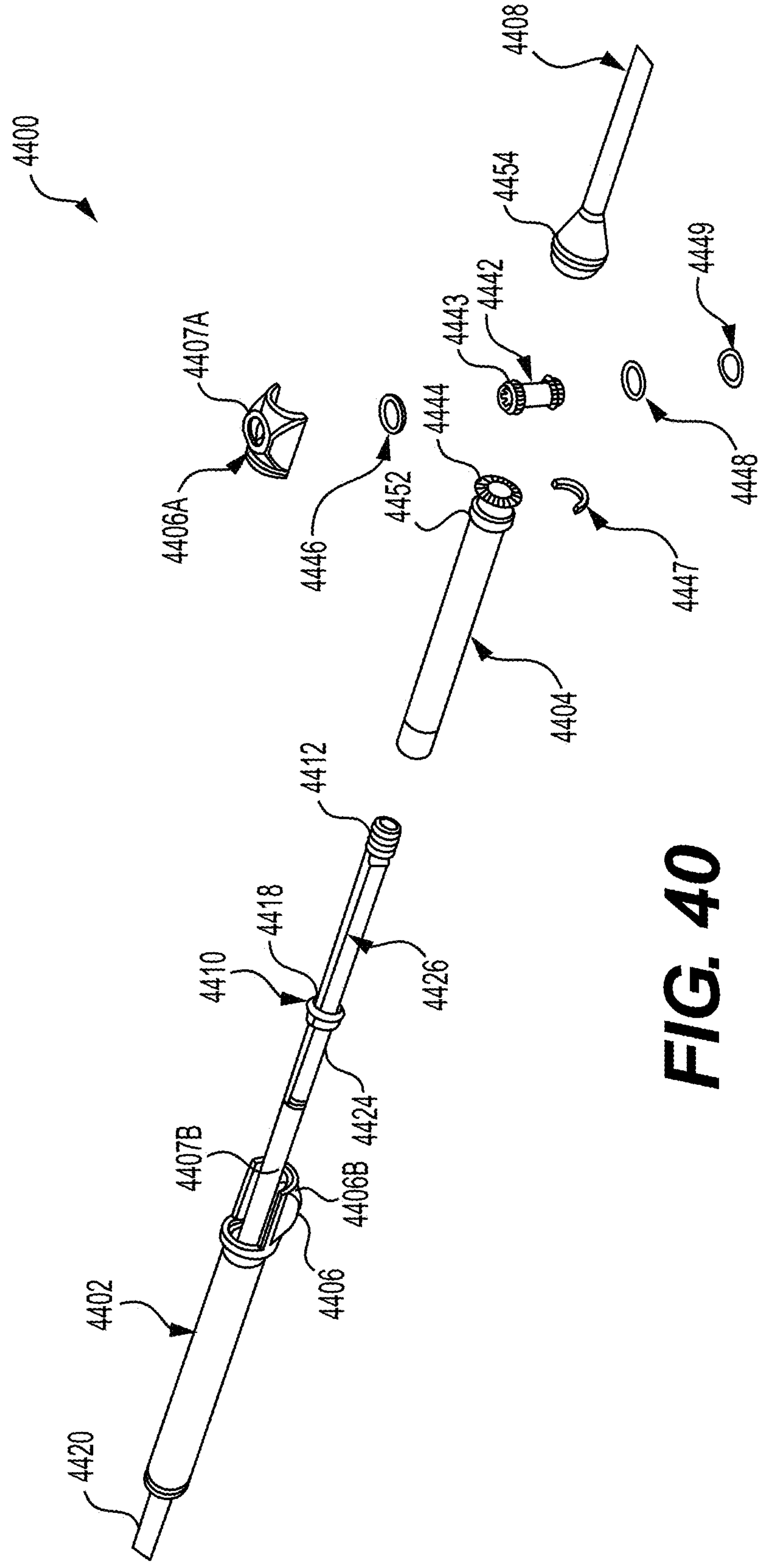
FIG. 40 is an exploded perspective view of an implantable rod assembly according to an alternative embodiment.

As shown in FIG. 40, the housing cap 4406 includes first and second portions 4406A, 4406B that fit together with a bevel pinion gear 4442 rotatably mounted between the portions 4406A, 4406B. In an exemplary embodiment, the housing 4402 and the housing cap 4406 are both made of biocompatible titanium alloy that are laser welded together to align and protect the internal components. It is contemplated, however, that suitable materials and modes of connection or attachment may be used. Each of the housing cap portions 4406A, 4406B has a through opening 4407A, 4407B, respectively, formed therein to allow access to either side of the bevel pinion gear 4442.

Figures 41, 42A:
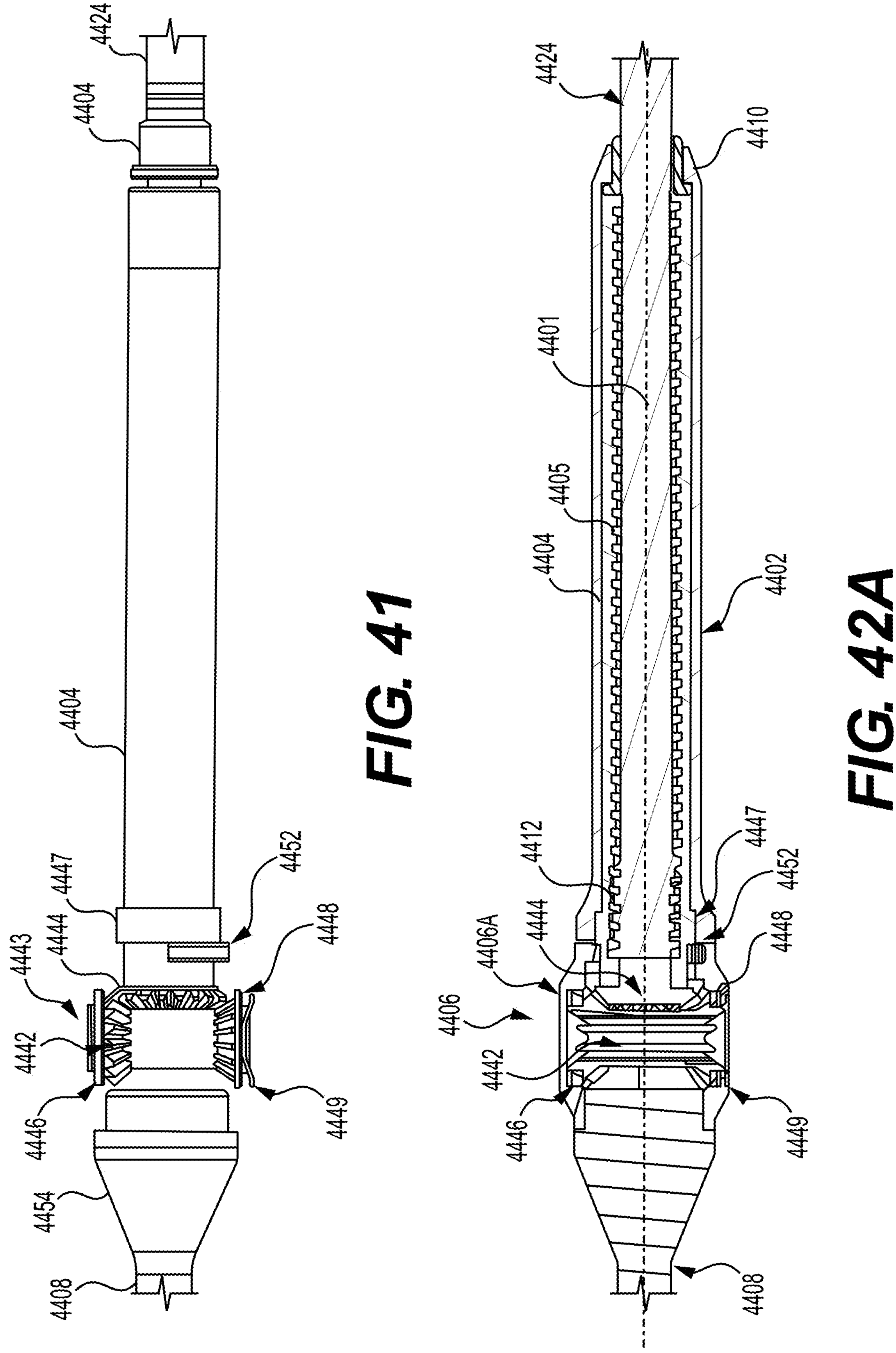
FIG. 41 is an enlarged side elevation view of the rod assembly of FIG. 40, with the housing omitted.
FIG. 42A is a side elevation view, in section, of the rod assembly of FIG. 40, with the extendible rod in a contracted position.

Referring to FIG. 42A, a keyed bushing 4410 is located in the housing 4402 at a distal end 4413 of the housing 4402. The bushing 4410 is substantially similar to the bushing 3310 described above. A keyway 4418 (shown in FIG. 40), for example, in the form of a flat surface is formed through the length of the bushing 4410. In an exemplary embodiment, the bushing 4410 can be constructed from biocompatible PEEK or other suitable materials and also functions to reduce friction and prevent wear between an expansion rod 4420 and the housing 4402.

The expansion rod 4420 is extendible through and from the housing 4402 along a longitudinal axis 4401. A distal end portion 4421 of the expansion rod 4420 is adapted to extend outwardly from the distal end 4413 of the housing 4402. As shown in FIG. 42A, the distal end portion 4421 has a cylindrical cross-section diameter of about 4.75 mm in order to accommodate commercially available pedicle screws that accept 4.75 mm diameter rods. However, it is contemplated that the diameter of the distal end portion 4421 may be any suitable diameter to mate with a corresponding pedicle screw system. The distal end portion 4421 is located outside the housing 4402 and has a pointed tip similar to the pointed tip 3323 shown in FIGS. 33 and 34 that allows the tip to tunnel through tissue when the expansion rod 4420 is being passed through the patient during implantation.

Figure 42B:
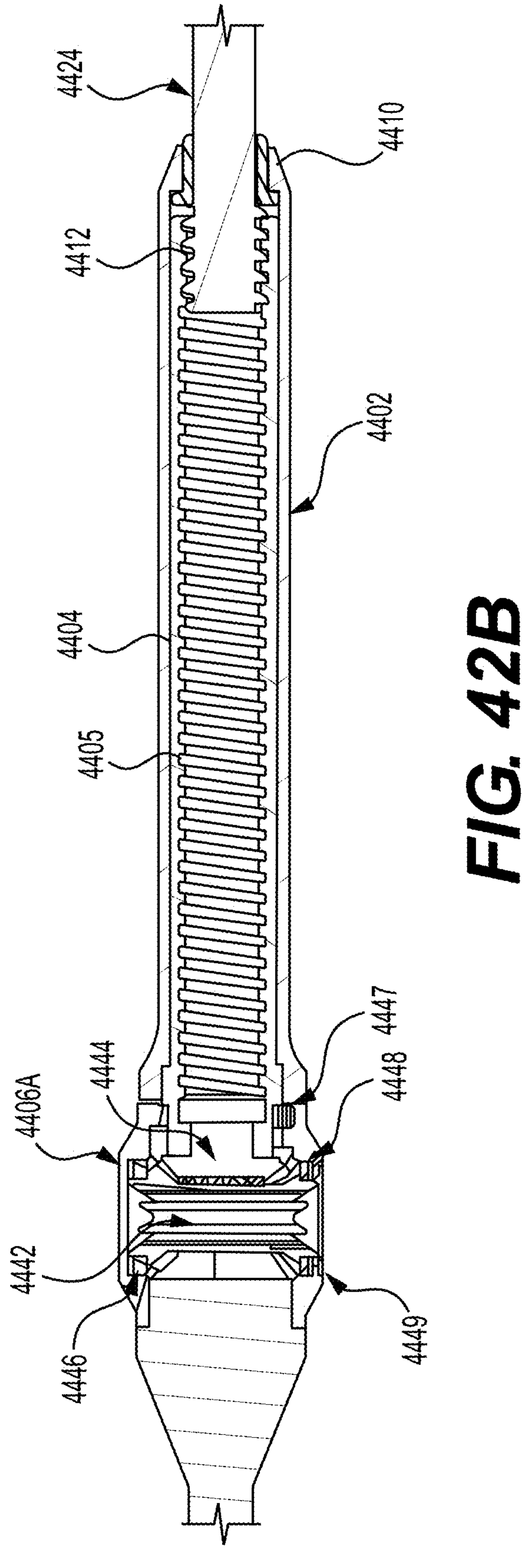
FIG. 42B is a side elevation view, in section, of the rod assembly of FIG. 40, with the extendible rod in an extended position.

The expansion rod 4420 has a threaded proximal end portion 4412 that is threadingly engaged with the internal threads 4405 of the expansion tube 4404. The proximal end portion 4412 has a larger diameter than the opening in the bushing 4410 so that, when the expansion rod 4420 is fully extended, as shown in FIG. 42B, the bushing 4410 retains the proximal end portion 4412 in the housing 4402.

A central body portion 4424 extends between the proximal end portion 4412 and the distal end portion of the expansion rod 4420. In a fully contracted position, as shown in FIG. 42A, at least a portion of the central body portion 4424 extends distally of the housing 4402. In some embodiments, the central body portion 4424 may have a diameter larger than the diameter of the distal end portion 4421. The larger diameter is configured to accommodate a mating key 4426, for example, in the form of a flat surface (see FIG. 40) that engages the keyway 4418 in the bushing 4410 to prevent rotation of the expansion rod 4420 as the expansion rod 4420 extends out of or contracts into the housing 4402. Therefore, as the internally threaded expansion tube 4404 rotates, the threaded connection between the internally threaded expansion tube 4404 and the threaded proximal end portion 4412 of the expansion rod 4420 causes the expansion rod 4420 to translate longitudinally along the longitudinal axis 4401.

Referring to FIG. 42A, a driver assembly is disposed in the housing 4402 and the housing cap 4406 and is adapted to translate, or extend, the expansion rod 4420 along the longitudinal axis 4401 in a distal direction from the hollow housing 4402.

In an exemplary embodiment, the driver assembly comprises a gear mechanism. Further, in an exemplary embodiment, the gear mechanism comprises a right-angle drive gear assembly. In an exemplary embodiment, the right-angle drive assembly comprises a bevel pinion gear 4442 and a bevel output gear 4444 rotatable about the longitudinal axis 4401. In some embodiments, the bevel output gear 4444 is press fit into the expansion tube 4404 such that the output gear 4444 and the expansion tube 4404 turn together. In some embodiments, the output gear 4444 and the expansion tube 4404 may alternatively be formed as one piece. As shown in FIG. 42A, the gear assembly is located in the housing cap 4406 between the housing 4402 and the fixed rod 4408. The pinion gear 4442 is disposed perpendicularly to the output gear 4444.

The bevel pinion gear 4442 is mounted in the housing cap 4406 and is supported by pinion bushings 4446, 4448 (shown in FIG. 35), such that one of the pinion bushings 4446, 4448 is mounted on either side of the bevel pinion gear 4442. In an exemplary embodiment, the pinion bushings 4446, 4448 are constructed from biocompatible PEEK or other suitable material and are used to reduce friction and prevent wear when rotating the pinion gear 4442. In an exemplary embodiment, the pinion gear 4442 has a hexalobular drive interface 4443 (similar to pinion gear 3342 described above). It is contemplated that other suitable drive interfaces 4443 and drivers may be selected. In some embodiments, the pinion gear 4442 may have teeth on both the upper and lower ends of the pinion gear, as depicted in FIGS. 40-42B. Utilizing teeth disposed at both ends of the pinion gear 4442 advantageously divides the load on the assembly 4400 between both sets of teeth when the assembly is implanted in a patient.

In some embodiments, a wave washer 4449 may be disposed between one of the pinion bushings 4446, 4448 and the housing 4402 to exert an upward force on the pinion gear 4442. The wave washer 4449 advantageously acts as a locking mechanism to undesired back drive when the assembly 4400 is implanted in a patient. The pinion gear 4442 has enough room within the housing 4402 and housing cap 4406 to translate along its own axis. In a neutral/locked state, the wave washer 4449 pushes the pinion gear 4442 upward such that the lower set of teeth of the pinion gear 4442 mesh with the teeth of the output gear 4444 while the upper set of teeth simultaneously remain engaged with the teeth of the output gear 4444 as well. As a result, the pinion and output gears 4442, 4444 are prevented from turning (i.e., are locked). As noted above, the patient's load is now distributed between both sets of teeth. To unlock the gear assembly, a surgeon inserts a driver into the drive interface 4443 and applies a light downward force, thus flattening the wave washer 4449, moving the pinon gear 4442 downward, and disengaging the lower set of teeth of the pinion gear 4442 from the teeth of the output gear 4444. As a result, the gear assembly is allowed to turn freely. When the surgeon removes the driver, the wave washer 4449 pushes the pinion gear 4442 upward again to reengage the lower set of teeth with the teeth of the output gear 4444, thus locking the gear assembly again. As a result, an automatic locking mechanism is advantageously provided to ensure the assembly maintains its desired length after being implanted in a patient and expanded to the desired length.

A bevel gear 4452 is disposed between the output gear 4444 and a collar 4447 formed at a proximal portion of the expansion tube 4404. In some embodiments, and as shown in FIGS. 40-42B, the bevel gear bushing 4452 can be a half ring constructed from a biocompatible titanium alloy or other suitable material. The bevel gear bushing 4452 serves to align the gear output 4444 with the pinion gear 4442, reduce friction, ensure that the gear output 4444 is held in place within the housing 4402, and prevent wear between the output gear 4444 and the housing 4402.

The bevel output gear 4444 forms an end (i.e., is integral with) the internally threaded expansion tube 4404. As a result, the expansion tube 4404 rotates with the bevel output gear 4444, thereby translating the expansion rod 4420 along the longitudinal axis 4401 as the bevel output gear 4444 rotates, to extend or contract the expansion rod 4420 from or into the housing 4404 such that the assembly 4400 expands or contracts in length, depending on the direction of rotation of the pinion gear 4442.

The bevel gear assembly allows a surgeon to turn the pinion gear 4442, which causes the expandable rod 4420 to extend distally from the housing 4402. In an exemplary embodiment, the pinion gear 4442 and the bevel output gear 4444 are both made of biocompatible titanium alloy (e.g., TAV), and are designed with a pitch angle such that the pinion gear 4442 is able to drive the bevel output gear 4444.

In some embodiments, the bevel gear assembly provides a reduction ration of 0.8:1 or more. In some embodiments, the bevel gear assembly provides a reduction ratio of 1:0.75 such that for every full revolution of the pinion gear 4442, the bevel output gear 4444 rotates 0.75 revolutions. In an exemplary embodiment, the ratio of the pinion teeth to the bevel gear teeth is 15:20. In an exemplary embodiment, the pinion gear 4442 is rotated about one (1) complete revolution to achieve between about 1 mm and 1.25 mm of expansion or contraction of the expansion rod 4420 from the housing 4402, with the amount of growth based upon a goal measure of 1.8 cm to 2.4 cm per year. Advantageously, a surgeon can fine tune the amount of expansion by either increasing or decreasing the amount of rotations. This allows the surgeon to expand the expansion rod 4420 against large forces caused by the deformity. If a surgeon feels too much distraction has been incorporated, the assembly 4400 can be reduced by simply reversing the direction the pinion gear 4442 is turned.

Similar to the assembly 3300 described above, in an exemplary embodiment, the assembly 4400 is 600 mm long with the expansion rod 4420 in a fully retracted position, and 660 mm long with the expansion rod 4420 in a fully extended position, allowing for up to 60 mm of growth of the patient.

Referring now to FIGS. 43A-43D, a growing rod assembly 5500 ("assembly 5500") in accordance with embodiments of the present disclosure and its implantation into a spinal assembly will now be discussed. The assembly 5500 advantageously non-invasively increases in length passively with the use of a ratchet mechanism. Instead of forcing the assembly 5500 to length (such as required with other growing rods), the assembly 5500 will react to tension forces by increasing in length. As such, after the initial lengthening by the surgeon implanting the assembly 5500 in a patient, the assembly 5500 as the patient stretches. The assembly 5500 includes a safety release mechanism in case of overstretching. In some embodiments, the assembly 5500 may be formed of titanium, stainless steel, cobalt chrome, or some other biocompatible material that is visible via MRI.

As depicted in FIGS. 43A-43D, in some embodiments, the assembly 5500 includes a fixed rod 5508 and an expansion rod 5520. As used with assembly 5500, the term "proximal" is defined as a direction toward the free end of the fixed rod 5508 and the term "distal" is defined as a direction toward the free end of the expandable rod 5520. The assembly 5500 includes a housing 5502 in the form of a hollow sleeve. A proximal portion 5520A of the expansion rod 5520 includes a plurality of teeth 5512 disposed on one side of the expansion rod 5520. In some embodiments, the proximal portion 5520A extends the entire length of the housing 5502.

In some embodiments, the safety release mechanism discussed above includes a pawl 5510 coupled to the housing 5502. The pawl 5510 is fixedly coupled to the housing 5502 at a proximal end 5510A and has a free end 5510B opposite the proximal end 5510A. As shown more clearly in FIGS. 43B and 43C, the free end 5510B extends into an opening 5507 formed in the housing 5502 to engage the teeth 5512 of the expansion rod 5520.

Figures 43A, 43B:
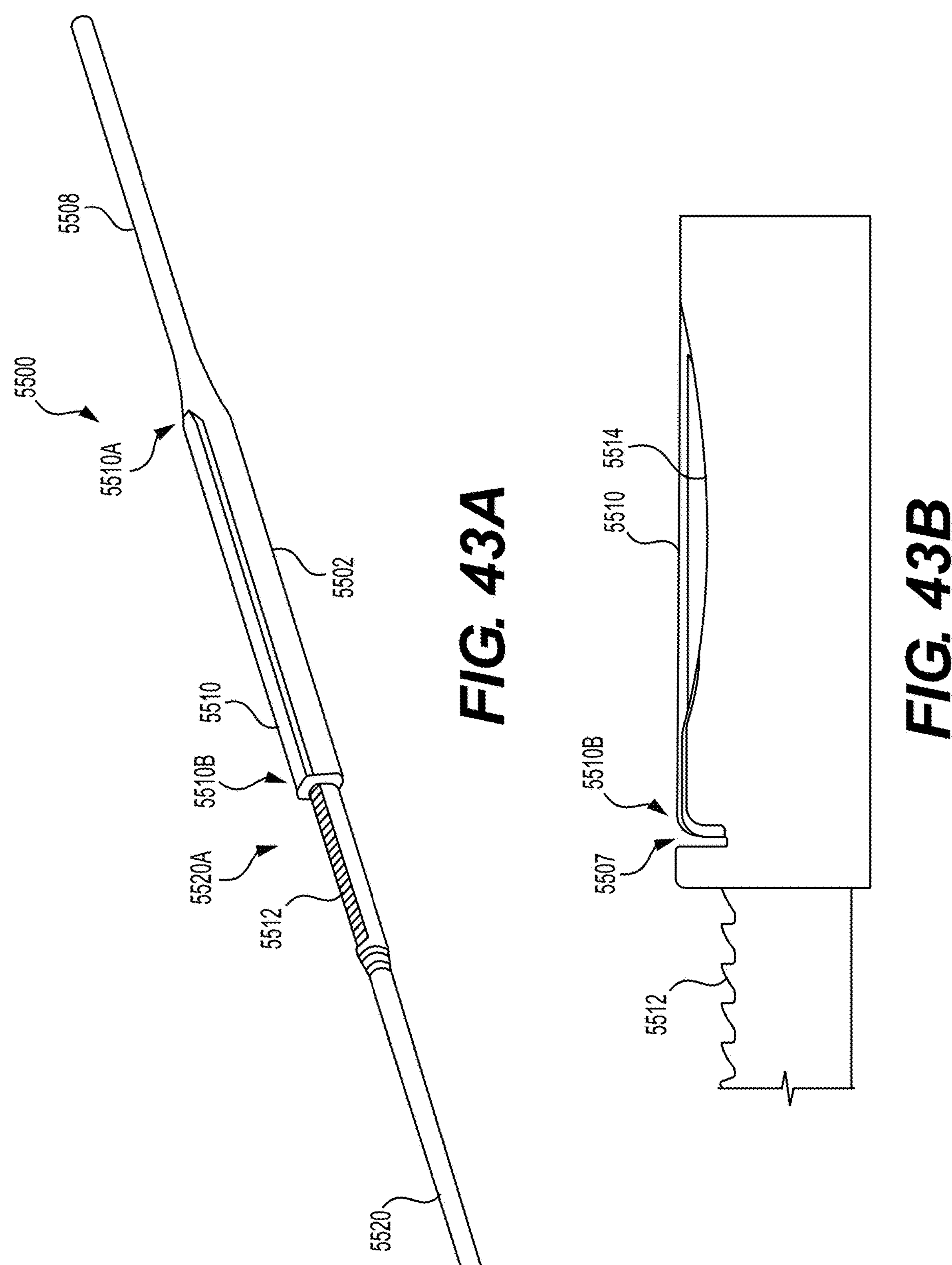
FIG. 43A is a perspective view of an implantable rod assembly according to an alternative embodiment.
FIG. 43B is a side close-up view of a ratchet mechanism of the rod assembly of FIG. 43A.
Figures 43C, 43D:
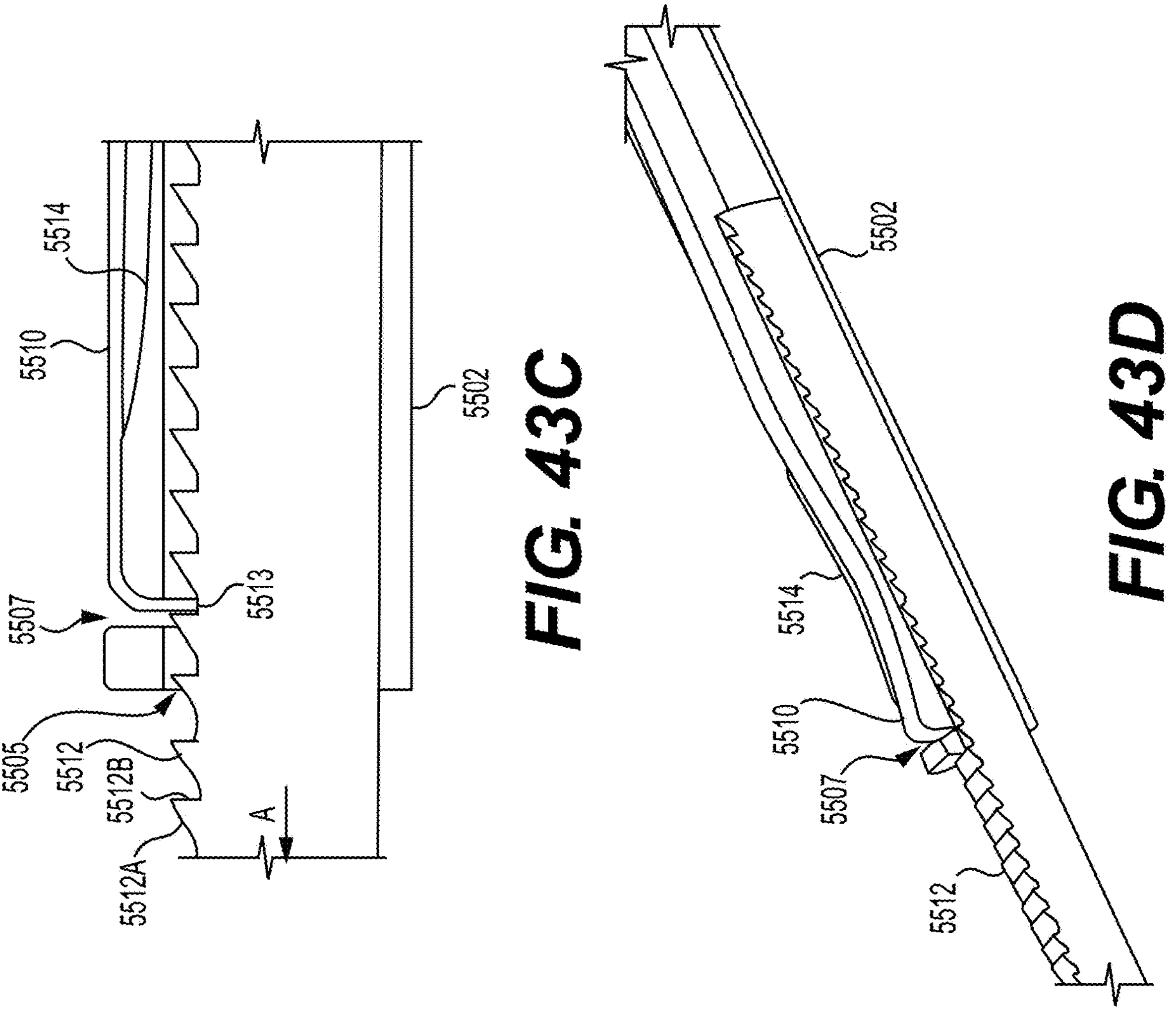
FIG. 43C is a side close-up view, in section, of the ratchet mechanism of FIG. 43B.
FIG. 43D is a perspective view, in section, of the rod assembly of FIG. 43A.

As shown more clearly in FIG. 43C, each of the teeth 5512 includes a ramped portion 5512A and a vertical portion 5512B. The assembly 5500 is configured such that the pawl 5510 allows the expansion rod 5520 to move in the direction indicated by arrow A because the free end 5510B of the pawl 5510 moves along the ramp. However, movement opposite the direction indicated by arrow A is prevented by the abutment of the free end 5510B of the pawl 5510 and the vertical portion 5512B of the teeth. As a result, when a patient stretches, the assembly 5500 expands (i.e., the expansion rod 5520 moves in the direction indicated by arrow A). However, the pawl 5510 prevents collapse of the assembly.

In the event of overexpansion, the safety release mechanism allows a desired amount of collapse of the assembly 5500. To achieve this, a depression 5514 is formed in the housing 5502 beneath the pawl 5510 near the free end 5510B, as shown in FIGS. 43B-43D. When the pawl 5510 is pushed into the depression (as depicted in FIG. 43D), the free end 5510B is moved out of engagement with the teeth 5512, thus allowing for the assembly 5500 to be collapsed a desired amount. The safety mechanism advantageously allows for the collapsing of the assembly 5500 non-invasively by simply pushing down on the patient's skin directly above the pawl 5510 until the pawl is pushed into the depression 5514.

In some embodiments, the pawl 5510 may alternative be formed of a material having a transition shape so that the pawl is in a released configuration when heated. As such, if the patient over-lengthens the assembly, heat can be applied to the area above the pawl to release it. The temperature at which such a transition would occur is above body temperature but less than a temperature that would cause harm to the patient.

Referring now to FIGS. 44-46B, a growing rod assembly 4800 ("assembly 4800") in accordance with embodiments of the present disclosure and its implantation into a spinal assembly will now be discussed. The assembly 4800 is substantially similar to the assemblies 3300, 4400 discussed above. As such, a discussion of many of the similar aspects will be limited here for brevity.

In some embodiments, the assembly 4800 includes a housing 4802 in the form of a hollow sleeve. An expansion tube 4804 with internal threads 4805 is mounted within the housing 4802 and extends the length thereof. In an exemplary embodiment, the threaded expansion tube 4804 is constructed from biocompatible polyether ether ketone (PEEK) to advantageously reduce metallic wear debris resulting from metal on metal contact and improve the imaging capability of the assembly 4800.

A housing cap 4806 is attached to and is part of the housing 4802. A fixed rod 4808 extends along a longitudinal axis 4801 (shown in FIG. 46A) proximally away from the housing 4802, such that the housing cap 4806 is located between the housing 4802 and the fixed rod 4808.

In an exemplary embodiment, the fixed rod 4808 is constructed from a biocompatible titanium alloy or any other suitable biocompatible material. The fixed rod 4808 has a distal end 4854 (e.g., a conical distal end 4854) that is fixedly connected to the housing cap 4806, an elongate body 4807 (e.g., a long 4.75 mm diameter cylindrical body 4407), and a proximal end 4809 (e.g., a pointed proximal tip 4809).

Figure 44:
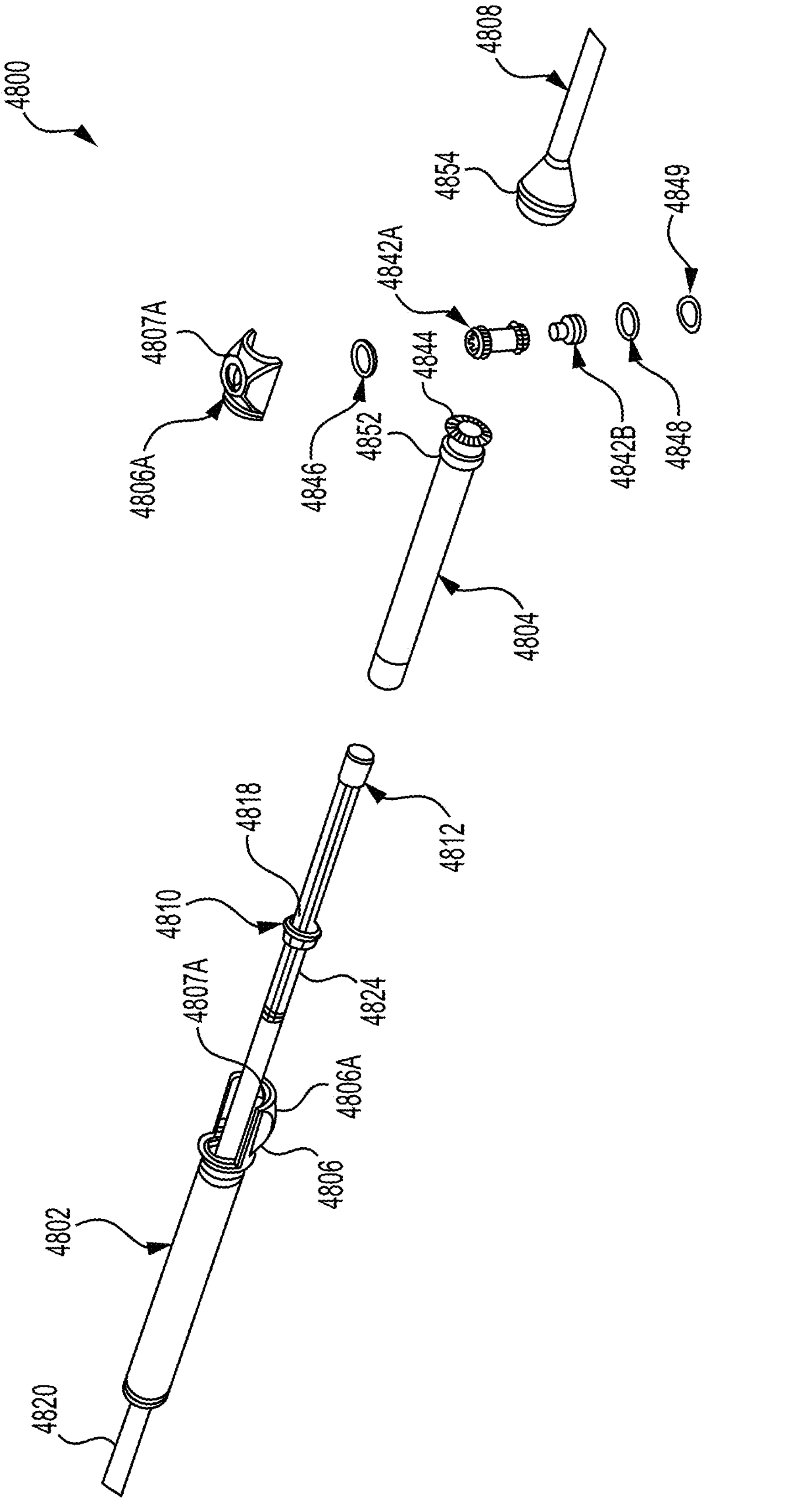
FIG. 44 is an exploded perspective view of an implantable rod assembly according to an alternative embodiment.

As shown in FIG. 44, the housing cap 4806 includes first and second portions 4806A, 4806B that fit together with a bevel pinion gear 4842A and a lock gear 4842B, both of which are rotatably mounted between the portions 4806A, 4806B. In an exemplary embodiment, the housing 4802 and the housing cap 4806 are both made of biocompatible titanium alloy that are laser welded together to align and protect the internal components. It is contemplated, however, that suitable materials and modes of connection or attachment may be used. The housing cap portion 4806A has a through opening 4807A formed therein to allow access to the bevel pinion gear 4442.

Figures 46A, 46B:
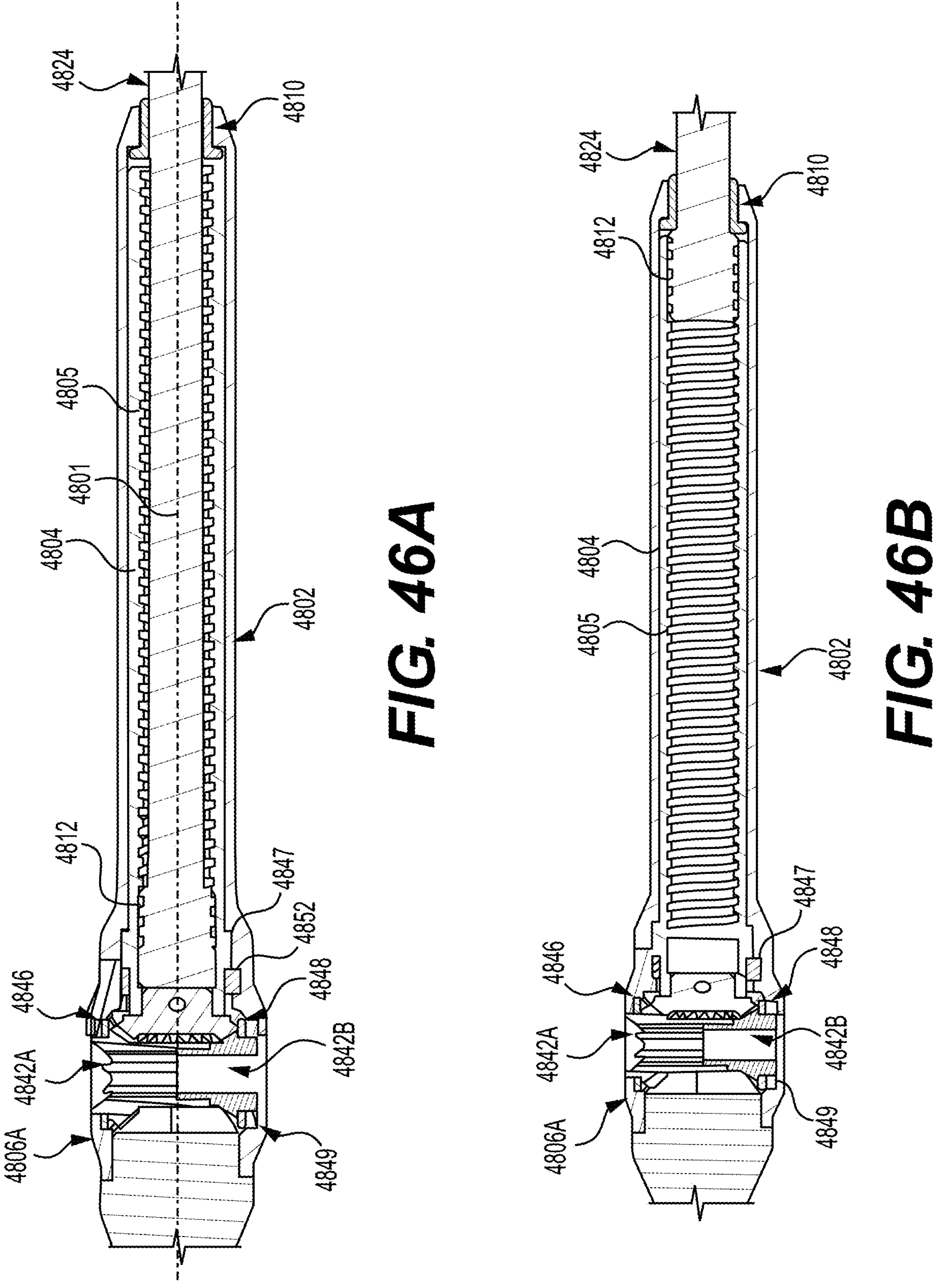
FIG. 46A is a side elevation view, in section, of the rod assembly of FIG. 44, with the extendible rod in a contracted position.
FIG. 46B is a side elevation view, in section, of the rod assembly of FIG. 44, with the extendible rod in an extended position.

Referring to FIG. 46A, a keyed bushing 4810 is located in the housing 4802 at a distal end 4813 of the housing 4802. The bushing 4810 is substantially similar to the bushings 3310 and 4410 described above. A keyway 4818 (shown in FIG. 44), for example, in the form of a flat surface is formed through the length of the bushing 4810. In an exemplary embodiment, the bushing 4810 can be constructed from biocompatible PEEK or other suitable materials and also functions to reduce friction and prevent wear between an expansion rod 4820 and the housing 4402.

The expansion rod 4820 is extendible through and from the housing 4802 along a longitudinal axis 4801. A distal end portion 4821 of the expansion rod 4820 is adapted to extend outwardly from the distal end 4813 of the housing 4802. As shown in FIG. 46A, the distal end portion 4821 has a cylindrical cross-section diameter of about 4.75 mm in order to accommodate commercially available pedicle screws that accept 4.75 mm diameter rods. However, it is contemplated that the diameter of the distal end portion 4821 may be any suitable diameter to mate with a corresponding pedicle screw system. The distal end portion 4821 is located outside the housing 4802 and has a pointed tip similar to the pointed tip 3323 shown in FIGS. 33 and 34 that allows the tip to tunnel through tissue when the expansion rod 4820 is being passed through the patient during implantation.

The expansion rod 4820 has a threaded proximal end portion 4812 that is threadingly engaged with the internal threads 4805 of the expansion tube 4804. The proximal end portion 4812 has a larger diameter than the opening in the bushing 4810 so that, when the expansion rod 4820 is fully extended, as shown in FIG. 46B, the bushing 4810 retains the proximal end portion 4812 in the housing 4802.

A central body portion 4824 extends between the proximal end portion 4812 and the distal end portion of the expansion rod 4820. In a fully contracted position, as shown in FIG. 46A, at least a portion of the central body portion 4824 extends distally of the housing 4802. In some embodiments, the central body portion 4824 may have a diameter larger than the diameter of the distal end portion 4821. The larger diameter is configured to accommodate a mating key 4826, for example, in the form of a flat surface (see FIG. 44) that engages the keyway 4818 in the bushing 4810 to prevent rotation of the expansion rod 4820 as the expansion rod 4820 extends out of or contracts into the housing 4802. Therefore, as the internally threaded expansion tube 4804 rotates, the threaded connection between the internally threaded expansion tube 4804 and the threaded proximal end portion 4812 of the expansion rod 4820 causes the expansion rod 4820 to translate longitudinally along the longitudinal axis 4801.

Referring to FIG. 46A, a driver assembly is disposed in the housing 4802 and the housing cap 4806 and is adapted to translate, or extend, the expansion rod 4820 along the longitudinal axis 4801 in a distal direction from the hollow housing 4802.

In an exemplary embodiment, the driver assembly comprises a gear mechanism. Further, in an exemplary embodiment, the gear mechanism comprises a right-angle drive gear assembly. In an exemplary embodiment, the right-angle drive assembly comprises a bevel pinion gear 4842A, a lock gear 4842B, and a bevel output gear 4844 rotatable about the longitudinal axis 4801. In some embodiments, the bevel output gear 4844 is press fit into the expansion tube 4804 such that the output gear 4844 and the expansion tube 4804 turn together. In some embodiments, the output gear 4844 and the expansion tube 4804 may alternatively be formed as one piece. As shown in FIG. 46A, the gear assembly is located in the housing cap 4806 between the housing 4802 and the fixed rod 4808. The pinion gear 4842A and the lock gear 4842B are both disposed perpendicularly to the output gear 4844.

The bevel pinion gear 4842A and the lock gear 4842B are mounted in the housing cap 4806 and supported by bushings 4846, 4848 (shown in FIG. 44), such that one of the bushings 4846 is mounted adjacent to the bevel pinion gear 4842A and the other of the bushings 4848 is mounted adjacent to the lock gear 4842B. In an exemplary embodiment, the bushings 4846, 4848 are constructed from biocompatible PEEK or other suitable material and are used to reduce friction and prevent wear when rotating the pinion gear 4842A and/or the lock gear 4842B. In an exemplary embodiment, the pinion gear 4842A has a hexalobular drive interface 4843 (similar to pinion gears 3342, 4443 described above). It is contemplated that other suitable drive interfaces 4843 and drivers may be selected. The pinion gear 4842A includes teeth 4882 on its upper end configured to mesh with teeth on the output gear 4844 and ratcheting teeth 4884 on its lower end configured to mesh with corresponding ratcheting teeth 4886 on an upper end of the lock gear 4842B, as depicted in FIGS. 44-46B.

In some embodiments, a wave washer 4849 may be disposed between the pinion bushing 4848 and the housing 4802 to exert an upward force on the lock gear 4442B. The wave washer 4849 acts as a locking mechanism for the gears and is configured to prevent undesired back drive when the assembly 4800 is implanted inside the patient. The pinion gear 4842A and the lock gear 4842B share the same axis 4880. Although axial movement of the pinion gear 4842A is prevented, axial movement of the lock gear 4852B between a first position (shown in FIG. 45B) and a second position (shown in FIG. 45C) along the axis 4880 is allowed. In the first position (i.e., a neutral/locked state), the wave washer 4889 forces the lock gear 4852B upward such that teeth 4888 at the bottom of the lock gear 4842B are forced into engagement with the teeth of the output gear 4844 while simultaneously maintaining engagement of the ratcheting teeth 4886 of the lock gear 4842B with the ratcheting teeth 4884 of the pinion gear 4842A.

Figures 45A, 45B, 45C:
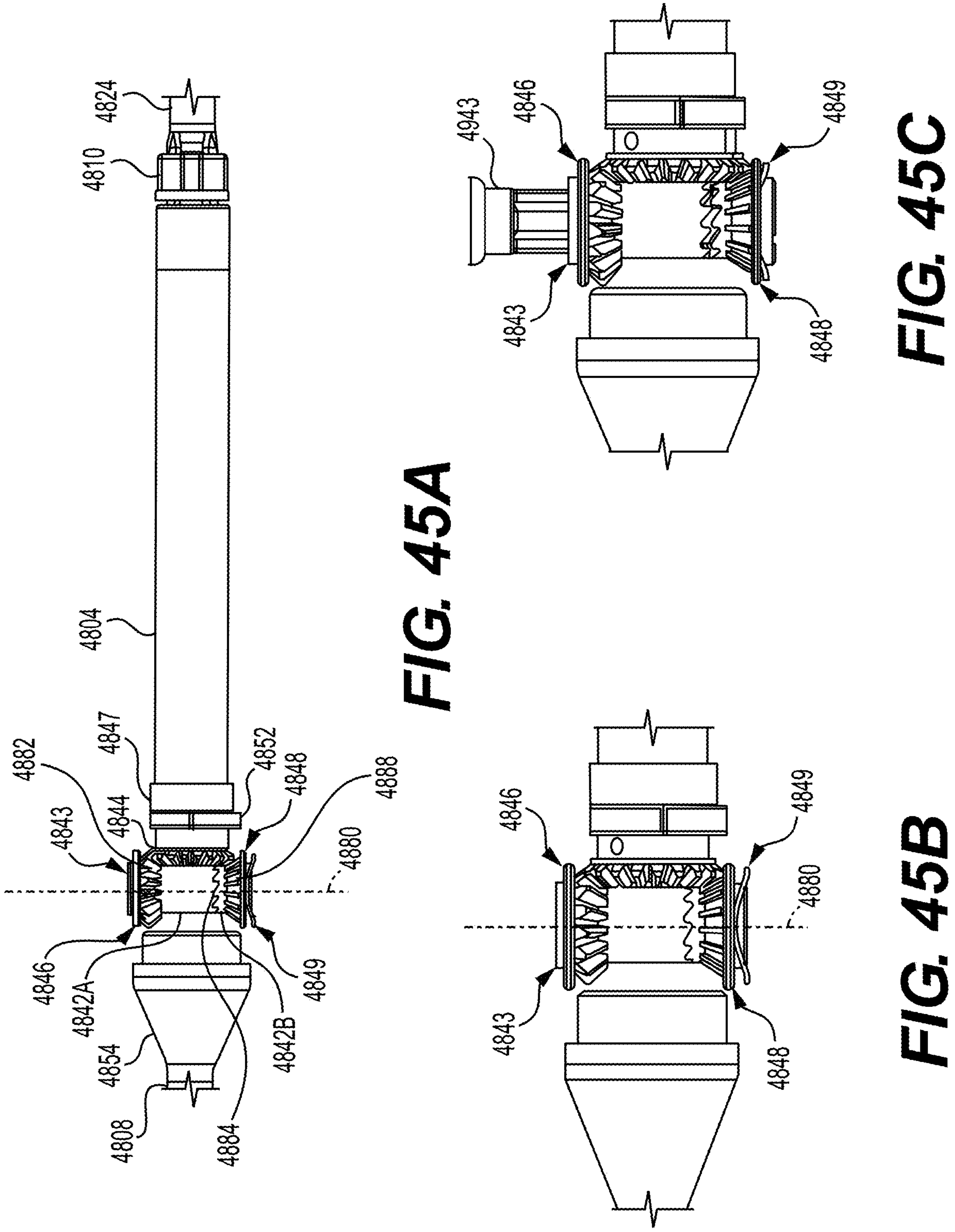
FIG. 45A is an enlarged side elevation view of the rod assembly of FIG. 44, with the housing omitted.
FIGS. 45B-45C are enlarged side elevation views of the gear assembly of the rod assembly illustrated in FIG. 45A.

As a result, rotation of the pinion gear 4842A and the output gear 4844 is prevented. To unlock the gear, a surgeon inserts a driver 4943 into the drive interface 4843 and applies a light downward force, which moves the lock gear 4842B downward and flattens the wave washer 4849. As a result, the teeth 4888 of the lock gear 4842B are pushed out of engagement with the teeth of the output gear 4844, thus allowing the pinion gear 4842A to turn freely, as shown in FIG. 45C. When the surgeon removes the driver 4943, the wave washer 4849 pushes the lock gear 4842B back up into engagement with the output gear 4844, thereby automatically locking the rotation of the gears. The ratcheting interface between the lock gear 4842B and the pinion gear 4842A (i.e., the interface between the ratcheting teeth 4884, 4886) allows the surgeon to expand the expansion rod 4820 without requiring a downward force. However, collapsing the expansion rod 4820 requires the disengagement of ratcheting teeth 4884, 4886 by pushing the lock gear 4842B downward, as explained above.

In some embodiments, a bevel gear bushing 4852 is disposed between the output gear 4844 and a collar 4847 formed at a proximal portion of the expansion tube 4804. In some embodiments, and as shown in FIGS. 44-46B, the bevel gear bushing 4852 can be a two-piece ring constructed from a biocompatible titanium alloy or other suitable material. The bevel gear bushing 4852 serves to align the gear output 4844 with the pinion gear 4842, reduce friction, ensure that the gear output 4844 is held in place within the housing 4802, and prevent wear between the output gear 4844 and the housing 4802.

The bevel output gear 4844 forms an end (i.e., is integral with) of the internally threaded expansion tube 4804. As a result, the expansion tube 4804 rotates with the bevel output gear 4844, thereby translating the expansion rod 4820 along the longitudinal axis 4801 as the bevel output gear 4844 rotates, to extend or contract the expansion rod 4820 from or into the housing 4804 such that the assembly 4800 expands or contracts in length, depending on the direction of rotation of the pinion gear 4842.

The bevel gear assembly allows a surgeon to turn the pinion gear 4842, which causes the expandable rod 4820 to extend distally from the housing 4802. In an exemplary embodiment, the pinion gear 4842 and the bevel output gear 4844 are both made of biocompatible titanium alloy (e.g., TAV), and are designed with a pitch angle such that the pinion gear 4842 is able to drive the bevel output gear 4844.

In some embodiments, the bevel gear assembly provides a reduction ration of 0.8:1 or more. In some embodiments, the bevel gear assembly provides a reduction ratio of 1:0.75 such that for every full revolution of the pinion gear 4842, the bevel output gear 4844 rotates 0.75 revolutions. In an exemplary embodiment, the ratio of the pinion teeth to the bevel gear teeth is 15:20. In an exemplary embodiment, the pinion gear 4842 is rotated about one (1) complete revolution to achieve between about 1 mm and 1.25 mm of expansion or contraction of the expansion rod 4820 from the housing 4802, with the amount of growth based upon a goal measure of 1.8 cm to 2.4 cm per year. Advantageously, a surgeon can fine tune the amount of expansion by either increasing or decreasing the amount of rotations. This allows the surgeon to expand the expansion rod 4820 against large forces caused by the deformity. If a surgeon feels too much distraction has been incorporated, the assembly 4800 can be reduced by simply reversing the direction the pinion gear 4842 is turned.

Similar to the assembly 4400 described above, in an exemplary embodiment, the assembly 4800 is 600 mm long with the expansion rod 4820 in a fully retracted position, and 660 mm long with the expansion rod 4820 in a fully extended position, allowing for up to 60 mm of growth of the patient.

Figures 47, 48:
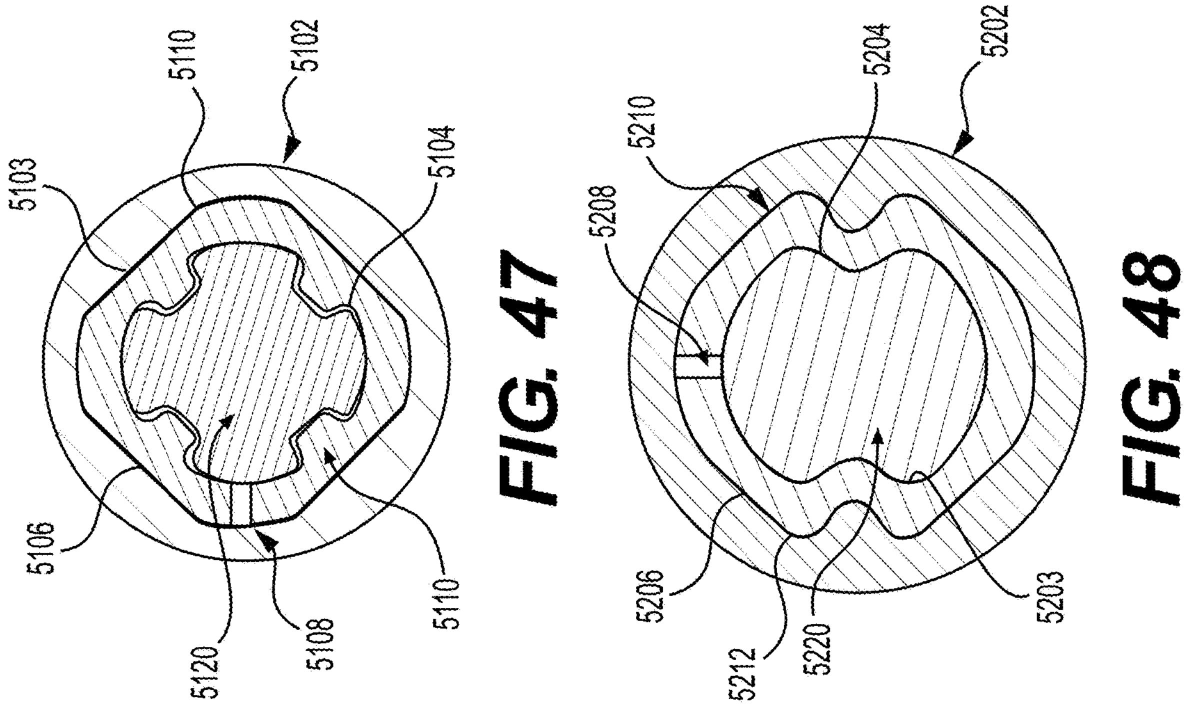
FIG. 47 is a cross-sectional view of an implantable rod assembly according to embodiments of the present disclosure.
FIG. 48 is a cross-sectional view of an implantable rod assembly according to embodiments of the present disclosure.

FIG. 47 is a cross-sectional view of an implantable rod assembly according to embodiments of the present disclosure. This cross-section is taken through a housing 5102 of the rod assembly (e.g., similar to housing 4802 described above), a bushing 5110 (e.g., similar to bushing 4810 described above), and an expansion rod 5120 (e.g., similar to expansion rod 4820 described above). In some embodiments, the bushing 5110 has a shape including four recesses 5103 configured to receive four corresponding lobes 5104 of the expansion rod 5120 to lock the expansion rod 5120 rotationally, but allow the rod to slide axially. In some embodiments, an outer surface 5106 of the bushing 5110 may have a square interface with the housing 5102 to prevent rotation of the bushing 5110 relative to the housing 5102. In some embodiments, the bushing 5110 may include a slit 5108 configured to allow for expansion of the bushing 5110 over an end (not shown in FIG. 47) of the expansion rod 5120 and sliding of the bushing 5110 into a grooved portion (not shown in FIG. 47) of the expansion rod 5120 during assembly. A pointed tip (not shown in FIG. 47) of the expansion rod 5120 forces the bushing 5110 open without harming the bushing 5110 during assembly. Although four lobes 5104 and recesses 5103 are depicted, it should be noted that the number of lobes and corresponding recesses may be fewer or greater as long as the desired relative rotational locking function is achieved.

FIG. 48 is a cross-sectional view of an implantable rod assembly according to embodiments of the present disclosure. This cross-section is taken through a housing 5202 of the rod assembly (e.g., similar to housing 4802 described above), a bushing 5210 (e.g., similar to bushing 4810 described above), and an expansion rod 5220 (e.g., similar to expansion rod 4820 described above). In some embodiments, the bushing 5210 has a central opening 5203 having dual-lobe shape which receives two lobes 5204 of the expansion rod 5220 to lock the expansion rod 5220 rotationally, but allow the rod to slide axially. In some embodiments, an outer surface 5206 of the bushing 5210 may two lobes 5212 which interface with the housing 5202 to prevent rotation of the bushing 5210 relative to the housing 5202. In some embodiments, the bushing 5210 may include a slit 5208 configured to allow for expansion of the bushing 5210 over an end (not shown in FIG. 48) of the expansion rod 5220 and sliding of the bushing 5210 into a grooved portion (not shown in FIG. 48) of the expansion rod 5220 during assembly. A pointed tip (not shown in FIG. 48) of the expansion rod 5220 forces the bushing 5210 open without harming the bushing 5210 during assembly. In some embodiments, the bushing 5210 may include two pieces (i.e., halves) (not shown) that are placed onto the expansion rod 5210 such that two slits 5208 are formed between the two pieces.

It is to be understood that the disclosure describes a few embodiments and that many variations of the invention can easily be devised by those skilled in the art. Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. An implantable growing rod assembly comprising:
- a housing;
- an internally threaded expansion tube mounted inside of the housing;
- a fixed rod extending along a longitudinal axis away from the housing;
- an expansion rod extendible from the housing along the longitudinal axis;
- a bevel gear assembly disposed in the housing and adapted to translate the expansion rod along the longitudinal axis, the bevel gear assembly including a bevel output gear having a plurality of gear teeth arranged circumferentially about the longitudinal axis and rotatable about the longitudinal axis; and
- a biased lock disposed in the housing and coupled to the bevel gear assembly, the biased lock including a locking bevel gear having a plurality of teeth arranged circumferentially around an axis which is lateral to the longitudinal axis and adapted to be coupled to the bevel output gear, the biased lock having a biased first position that prevents the bevel gear assembly from rotation and an unlocked second position configured to allow the bevel gear assembly to rotate to expand and collapse the expansion rod,
- wherein the bevel gear assembly includes a bevel pinion gear having teeth at one end and arranged to rotate simultaneously with the locking bevel gear.

2. The implantable growing rod assembly according to claim 1, wherein the expansion rod comprises a threaded proximal end threadingly engaged with the internally threaded expansion tube.

3. The implantable growing rod assembly according to claim 2, wherein the expansion rod comprises a distal end adapted to extend outwardly from the housing.

4. The implantable growing rod assembly according to claim 1, wherein the bevel gear assembly is located in a housing cap between the housing and the fixed rod.

5. The implantable growing rod assembly according to claim 4, further comprising:
- a first pinion bushing disposed between a bevel pinion gear and the housing; and
- a second pinion bushing disposed between a lock gear and the housing.

6. The implantable growing rod assembly of claim 5, wherein the internally threaded expansion tube is formed of PEEK.

7. The implantable growing rod assembly of claim 1, further comprising:
- a wave washer disposed between the housing and the lock and configured to exert an upward force on the lock to bias the lock towards the normally biased first position.

8. The implantable growing rod assembly according to claim 1, further comprising:
- a keyed bushing disposed in the housing and wherein the expansion rod comprises a mating key located in the keyed bushing such that, as the expansion rod extends from the housing, the keyed bushing prevents the expansion rod from rotating.

9. The implantable growing rod assembly according to claim 8, wherein the keyed bushing includes four recesses, wherein the expansion rod includes four lobes configured to be disposed in corresponding ones of the four recesses to prevent rotation of the expansion rod relative to the keyed bushing, and wherein an outer surface of the keyed bushing includes a square shape to prevent rotation of the keyed bushing with respect to the housing.

10. The implantable growing rod assembly according to claim 8, wherein the keyed bushing includes an opening having a first dual-lobe shape, wherein the expansion rod includes two lobes corresponding to the first dual-lobe shape of the opening to prevent rotation of the expansion rod relative to the keyed bushing, and wherein an outer surface of the keyed bushing includes a second dual-lobe shape to prevent rotation of the keyed bushing with respect to the housing.

11. An implantable growing rod assembly comprising:
- a housing;
- an internally threaded expansion tube mounted inside of the housing, wherein the internally threaded expansion tube is formed of PEEK;
- a fixed rod extending along a longitudinal axis away from the housing;
- an expansion rod extendible from the housing along the longitudinal axis;
- a bevel gear assembly disposed in the housing and adapted to translate the expansion rod along the longitudinal axis, the bevel gear assembly including a bevel output gear having a plurality of gear teeth arranged circumferentially about the longitudinal axis and rotatable about the longitudinal axis; and a biased lock disposed in the housing and coupled to the bevel gear assembly, the biased lock including a locking bevel gear having a plurality of teeth arranged circumferentially around an axis which is lateral to the longitudinal axis and adapted to be coupled to the bevel output gear, the biased lock having a biased first position that prevents the bevel gear assembly from rotation and an unlocked second position configured to allow the bevel gear assembly to rotate to expand and collapse the expansion rod, wherein the bevel gear assembly includes a bevel pinion gear having teeth at one end and arranged to rotate simultaneously with the locking bevel gear.

12. The implantable growing rod assembly according to claim 11, wherein the expansion rod comprises a threaded proximal end threadingly engaged with the internally threaded expansion tube.

13. The implantable growing rod assembly according to claim 12, wherein the expansion rod comprises a distal end adapted to extend outwardly from the housing.

14. The implantable growing rod assembly according to claim 11, wherein the bevel gear assembly is located in a housing cap between the housing and the fixed rod.

15. The implantable growing rod assembly according to claim 11, further comprising:

a keyed bushing located in the housing and wherein the expansion rod comprises a mating key located in the keyed bushing such that, as the expansion rod extends from the housing, the keyed bushing prevents the expansion rod from rotating.

16. The implantable growing rod assembly according to claim 15, wherein the keyed bushing includes four recesses, wherein the expansion rod includes four lobes configured to be disposed in corresponding ones of the four recesses to prevent rotation of the expansion rod relative to the keyed bushing, and wherein an outer surface of the keyed bushing includes a square shape to prevent rotation of the keyed bushing with respect to the housing.

17. The implantable growing rod assembly according to claim 15, wherein the keyed bushing includes an opening having a first dual-lobe shape, wherein the expansion rod includes two lobes corresponding to the first dual-lobe shape of the opening to prevent rotation of the expansion rod relative to the keyed bushing, and wherein an outer surface of the keyed bushing includes a second dual-lobe shape to prevent rotation of the keyed bushing with respect to the housing.

* * * * *